United States Patent
Levin et al.

(10) Patent No.: US 9,999,424 B2
(45) Date of Patent: Jun. 19, 2018

(54) MEANS AND METHOD FOR REVERSIBLY CONNECTING AN IMPLANT TO A DEPLOYMENT DEVICE

(75) Inventors: Ofek Levin, Moshav Amirim (IL); Arie Levy, Ramat-Gan (IL)

(73) Assignee: Covidien LP, Mansfield, MA (US)

( * ) Notice: Subject to any disclaimer, the term of this patent is extended or adjusted under 35 U.S.C. 154(b) by 880 days.

(21) Appl. No.: 12/831,570

(22) Filed: Jul. 7, 2010

(65) Prior Publication Data
US 2011/0040310 A1   Feb. 17, 2011

Related U.S. Application Data

(60) Provisional application No. 61/234,407, filed on Aug. 17, 2009.

(51) Int. Cl.
| | |
|---|---|
| A61B 17/08 | (2006.01) |
| A61B 17/068 | (2006.01) |
| A61B 17/076 | (2006.01) |
| A61B 17/00 | (2006.01) |
| A61F 2/00 | (2006.01) |

(52) U.S. Cl.
CPC ........ *A61B 17/0686* (2013.01); *A61B 17/076* (2013.01); *A61B 2017/0053* (2013.01); *A61F 2002/0072* (2013.01)

(58) Field of Classification Search
CPC ........... A61F 2002/0072; A61F 2/0063; A61B 17/064; A61B 17/00234
USPC ........................................ 606/151, 213, 215
See application file for complete search history.

(56) References Cited

U.S. PATENT DOCUMENTS

| | | |
|---|---|---|
| 4,347,847 A | 9/1982 | Usher |
| 4,400,833 A | 8/1983 | Kurland |
| 4,452,245 A | 6/1984 | Usher |
| 4,485,816 A | 12/1984 | Krumme |
| 4,585,458 A | 4/1986 | Kurland |
| 4,633,873 A | 1/1987 | Dumican et al. |
| 4,838,884 A | 6/1989 | Dumican et al. |
| 4,854,316 A | 8/1989 | Davis |
| 5,019,096 A | 5/1991 | Fox, Jr. et al. |
| 5,116,357 A | 5/1992 | Eberbach |
| 5,122,155 A | 6/1992 | Eberbach |
| 5,125,553 A | 6/1992 | Oddsen et al. |
| 5,141,515 A | 8/1992 | Eberbach |
| 5,147,374 A | 9/1992 | Fernandez |
| 5,176,692 A | 1/1993 | Wilk et al. |
| 5,203,864 A | 4/1993 | Phillips |
| 5,219,077 A | 6/1993 | Transue |
| 5,249,682 A | 10/1993 | Transue |
| 5,254,133 A | 10/1993 | Seid |
| 5,258,000 A | 11/1993 | Gianturco |

(Continued)

FOREIGN PATENT DOCUMENTS

| | | |
|---|---|---|
| CA | 2413904 A1 | 10/2003 |
| EP | 0328421 A2 | 8/1989 |

(Continued)

OTHER PUBLICATIONS

US 6,503,260, 01/2003, Schaller et al. (withdrawn)

(Continued)

*Primary Examiner* — Todd J Scherbel

(57) ABSTRACT

The present invention generally relates to devices and methods for reversibly coupling an implant to a deployment device.

26 Claims, 29 Drawing Sheets

(56) References Cited

U.S. PATENT DOCUMENTS

| | | |
|---|---|---|
| 5,263,969 A | 11/1993 | Phillips |
| 5,289,963 A | 3/1994 | McGarry et al. |
| 5,290,217 A | 3/1994 | Campos |
| 5,304,187 A * | 4/1994 | Green et al. ............... 606/151 |
| 5,292,328 A | 8/1994 | Hain et al. |
| 5,333,624 A | 8/1994 | Tovey |
| 5,354,292 A | 10/1994 | Braeuer et al. |
| 5,356,064 A | 10/1994 | Green et al. |
| 5,356,432 A | 10/1994 | Rutkow et al. |
| 5,364,002 A | 11/1994 | Green et al. |
| 5,364,004 A | 11/1994 | Davidson |
| 5,366,460 A | 11/1994 | Eberbach |
| 5,368,602 A | 11/1994 | de la Torre |
| 5,370,650 A | 12/1994 | Tovey et al. |
| 5,376,097 A | 12/1994 | Phillips |
| 5,383,477 A * | 1/1995 | DeMatteis ............... 128/898 |
| 5,392,978 A | 2/1995 | Velez et al. |
| 5,397,331 A | 3/1995 | Himpens et al. |
| 5,397,332 A * | 3/1995 | Kammerer et al. ........ 606/151 |
| 5,405,360 A * | 4/1995 | Tovey ....................... 606/151 |
| 5,425,357 A | 6/1995 | Moll et al. |
| 5,425,740 A | 6/1995 | Hutchinson |
| 5,433,996 A | 7/1995 | Kranzler et al. |
| 5,464,403 A | 11/1995 | Kieturakis et al. |
| 5,497,933 A | 3/1996 | DeFonzo et al. |
| 5,531,759 A | 7/1996 | Kensey et al. |
| 5,542,594 A | 8/1996 | McKean |
| 5,560,224 A | 10/1996 | Tessler |
| 5,560,532 A | 10/1996 | DeFonzo et al. |
| 5,564,615 A | 10/1996 | Bishop et al. |
| 5,569,273 A | 10/1996 | Titone et al. |
| 5,577,654 A | 11/1996 | Bishop |
| 5,588,580 A | 12/1996 | Paul et al. |
| 5,588,581 A | 12/1996 | Conlon et al. |
| 5,601,224 A | 2/1997 | Bishop et al. |
| 5,614,284 A | 3/1997 | Kranzler et al. |
| 5,618,290 A | 4/1997 | Toy et al. |
| 5,626,587 A | 5/1997 | Bishop et al. |
| 5,634,584 A | 6/1997 | Okorocha et al. |
| 5,634,931 A | 6/1997 | Kugel |
| 5,662,662 A | 9/1997 | Bishop et al. |
| 5,695,525 A | 12/1997 | Mulhauser et al. |
| 5,716,409 A | 2/1998 | Debbas |
| 5,725,577 A | 3/1998 | Saxon |
| 5,728,119 A | 3/1998 | Smith et al. |
| 5,749,895 A | 5/1998 | Sawyer et al. |
| 5,766,246 A | 6/1998 | Mulhauser et al. |
| 5,769,864 A | 6/1998 | Kugel |
| 5,779,728 A | 7/1998 | Lunsford et al. |
| 5,810,851 A | 9/1998 | Yoon |
| 5,814,058 A | 9/1998 | Carlson et al. |
| 5,817,109 A | 10/1998 | McGarry et al. |
| 5,824,082 A | 10/1998 | Brown |
| 5,836,961 A | 11/1998 | Kieturakis et al. |
| 5,854,383 A | 12/1998 | Erneta et al. |
| 5,863,531 A | 1/1999 | Naughton et al. |
| 5,865,728 A | 2/1999 | Moll et al. |
| 5,911,726 A | 6/1999 | Belknap |
| 5,916,225 A | 6/1999 | Kugel |
| 5,925,058 A | 7/1999 | Smith et al. |
| 5,951,997 A | 9/1999 | Bezwada et al. |
| 5,954,767 A | 9/1999 | Pajotin et al. |
| 5,972,007 A | 10/1999 | Sheffield et al. |
| 5,972,008 A | 10/1999 | Kalinski et al. |
| 5,990,378 A | 11/1999 | Ellis |
| 6,004,333 A | 12/1999 | Sheffield et al. |
| 6,042,592 A | 3/2000 | Schmitt |
| 6,066,776 A | 5/2000 | Goodwin et al. |
| 6,066,777 A | 5/2000 | Benchetrit |
| 6,090,116 A | 7/2000 | D'Aversa et al. |
| 6,113,609 A | 9/2000 | Adams |
| 6,113,611 A | 9/2000 | Allen et al. |
| 6,113,624 A | 9/2000 | Bezwada et al. |
| 6,166,286 A | 12/2000 | Trabucco |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,197,036 B1 | 3/2001 | Tripp et al. |
| 6,214,020 B1 | 4/2001 | Mulhauser et al. |
| 6,224,616 B1 | 5/2001 | Kugel |
| 6,241,768 B1 | 6/2001 | Agarwal et al. |
| 6,258,113 B1 | 7/2001 | Adams et al. |
| 6,258,124 B1 | 7/2001 | Darois et al. |
| 6,267,772 B1 | 7/2001 | Mulhauser et al. |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,312,442 B1 | 11/2001 | Kieturakis et al. |
| 6,319,264 B1 | 11/2001 | Tormala et al. |
| 6,368,541 B1 | 4/2002 | Pajotin et al. |
| 6,375,662 B1 | 4/2002 | Schmitt |
| 6,383,201 B1 | 5/2002 | Dong |
| 6,391,060 B1 | 5/2002 | Ory et al. |
| 6,408,656 B1 | 6/2002 | Ory et al. |
| 6,416,486 B1 | 7/2002 | Wampler |
| 6,425,900 B1 | 7/2002 | Knodel et al. |
| 6,425,924 B1 | 7/2002 | Rousseau |
| 6,436,030 B2 | 8/2002 | Rehil |
| 6,447,524 B1 | 9/2002 | Knodel et al. |
| 6,478,803 B1 | 11/2002 | Kapec et al. |
| 6,485,503 B2 | 11/2002 | Jacobs et al. |
| 6,497,650 B1 | 12/2002 | Nicolo |
| 6,517,584 B1 | 2/2003 | Lecalve |
| 6,527,785 B2 | 3/2003 | Sancoff et al. |
| 6,551,241 B1 | 4/2003 | Schultz |
| 6,551,333 B2 | 4/2003 | Kuhns et al. |
| 6,558,400 B2 | 5/2003 | Deem et al. |
| 6,565,590 B2 | 5/2003 | Kieturakis et al. |
| 6,575,988 B2 | 6/2003 | Rousseau |
| 6,607,541 B1 | 8/2003 | Gardiner et al. |
| 6,610,006 B1 | 8/2003 | Amid et al. |
| 6,613,059 B2 | 9/2003 | Schaller et al. |
| 6,616,685 B2 | 9/2003 | Rousseau |
| 6,638,208 B1 | 10/2003 | Natarajan et al. |
| 6,638,284 B1 | 10/2003 | Rousseau et al. |
| 6,638,292 B2 | 10/2003 | Adams |
| 6,638,297 B1 | 10/2003 | Huitema |
| 6,652,595 B1 | 11/2003 | Nicolo |
| 6,666,817 B2 | 12/2003 | Li |
| 6,669,706 B2 | 12/2003 | Schmitt et al. |
| 6,669,735 B1 | 12/2003 | Pelissier |
| 6,676,643 B2 | 1/2004 | Brushey |
| 6,689,047 B2 | 2/2004 | Gellman |
| 6,694,192 B2 | 2/2004 | Policker et al. |
| 6,695,856 B2 | 2/2004 | Kieturakis et al. |
| 6,709,442 B2 | 3/2004 | Miller et al. |
| 6,736,823 B2 | 5/2004 | Darois et al. |
| 6,736,854 B2 | 5/2004 | Vadurro et al. |
| 6,737,371 B1 | 5/2004 | Planck et al. |
| 6,746,458 B1 | 6/2004 | Cloud |
| 6,755,867 B2 | 6/2004 | Rousseau |
| 6,773,438 B1 | 8/2004 | Knodel et al. |
| 6,783,554 B2 | 8/2004 | Amara et al. |
| 6,790,213 B2 | 9/2004 | Cherok et al. |
| 6,800,081 B2 | 10/2004 | Parodi |
| 6,800,082 B2 | 10/2004 | Rousseau |
| 6,805,669 B2 | 10/2004 | Swanbom |
| 6,833,408 B2 | 12/2004 | Sehl et al. |
| 6,837,893 B2 | 1/2005 | Miller |
| 6,893,452 B2 | 5/2005 | Jacobs |
| 6,913,607 B2 | 7/2005 | Ainsworth et al. |
| 6,913,622 B2 | 7/2005 | Gjunter |
| 6,936,052 B2 | 8/2005 | Gellman et al. |
| 6,945,980 B2 | 9/2005 | Nguyen et al. |
| 6,953,428 B2 | 10/2005 | Gellman et al. |
| 6,960,217 B2 | 11/2005 | Bolduc |
| 6,960,233 B1 | 11/2005 | Berg et al. |
| 6,966,916 B2 | 11/2005 | Kumar |
| 6,974,586 B2 | 12/2005 | Greenhalgh et al. |
| 6,991,597 B2 | 1/2006 | Gellman et al. |
| 7,001,405 B2 | 2/2006 | Kieturakis et al. |
| 7,011,688 B2 | 3/2006 | Gryska et al. |
| 7,025,772 B2 | 4/2006 | Gellman et al. |
| 7,049,345 B2 | 5/2006 | Holmes-Farley |

(56) References Cited

U.S. PATENT DOCUMENTS

| | | |
|---|---|---|
| 7,077,850 B2 | 7/2006 | Kortenbach |
| 7,083,629 B2 | 8/2006 | Weller et al. |
| 7,083,630 B2 | 8/2006 | DeVries et al. |
| 7,094,261 B2 | 8/2006 | Zotti et al. |
| 7,101,366 B2 | 9/2006 | Trout, III et al. |
| 7,101,381 B2 | 9/2006 | Ford et al. |
| 7,119,062 B1 | 10/2006 | Alvis et al. |
| 7,148,315 B2 | 12/2006 | Erneta et al. |
| 7,198,046 B1 | 4/2007 | Argenta et al. |
| 7,214,236 B2 | 5/2007 | Kieturakis et al. |
| 7,216,651 B2 | 5/2007 | Argenta et al. |
| 7,220,282 B2 | 5/2007 | Kuslich |
| 7,229,452 B2 | 6/2007 | Kayan |
| 7,235,043 B2 | 6/2007 | Gellman et al. |
| 7,235,295 B2 | 6/2007 | Laurencin et al. |
| 7,255,675 B2 | 8/2007 | Gertner et al. |
| 7,320,325 B2 | 1/2008 | Duchon et al. |
| 7,331,199 B2 | 2/2008 | Ory et al. |
| 7,381,225 B2 | 6/2008 | Croce et al. |
| 7,404,819 B1 | 7/2008 | Darios et al. |
| 7,406,969 B2 | 8/2008 | Duchon et al. |
| 7,407,480 B2 | 8/2008 | Staskin et al. |
| 7,491,232 B2 | 2/2009 | Bolduc et al. |
| 7,500,945 B2 | 3/2009 | Cox et al. |
| 7,500,993 B2 | 3/2009 | De La Torre et al. |
| 7,524,333 B2 | 4/2009 | Lambrecht et al. |
| 7,544,213 B2 | 6/2009 | Adams |
| 7,553,329 B2 | 6/2009 | Lambrecht et al. |
| 7,553,330 B2 | 6/2009 | Lambrecht et al. |
| RE40,833 E | 7/2009 | Wintermantel et al. |
| 7,566,337 B2 | 7/2009 | Sogaard-Andersen et al. |
| 7,594,921 B2 | 9/2009 | Browning |
| 7,601,118 B2 | 10/2009 | Smith et al. |
| 7,601,172 B2 | 10/2009 | Segal et al. |
| 8,097,008 B2 * | 1/2012 | Henderson .................. 606/151 |
| 2001/0016754 A1 | 8/2001 | Adams et al. |
| 2001/0018592 A1 | 8/2001 | Schaller et al. |
| 2001/0018593 A1 | 8/2001 | Nguyen et al. |
| 2001/0027347 A1 | 10/2001 | Rousseau |
| 2001/0044637 A1 | 11/2001 | Jacobs et al. |
| 2001/0049538 A1 | 12/2001 | Trabucco |
| 2001/0049539 A1 | 12/2001 | Rehil |
| 2001/0053919 A1 | 12/2001 | Kieturakis et al. |
| 2001/0056275 A1 | 12/2001 | Brushey |
| 2002/0010457 A1 | 1/2002 | Duchon et al. |
| 2002/0010480 A1 | 1/2002 | Sancoff et al. |
| 2002/0010490 A1 | 1/2002 | Schaller et al. |
| 2002/0010494 A1 | 1/2002 | Policker et al. |
| 2002/0029048 A1 | 3/2002 | Miller |
| 2002/0042658 A1 | 4/2002 | Tyagi |
| 2002/0049503 A1 | 4/2002 | Milbocker |
| 2002/0049504 A1 | 4/2002 | Barault |
| 2002/0052612 A1 | 5/2002 | Schmitt et al. |
| 2002/0052654 A1 | 5/2002 | Darois et al. |
| 2002/0058967 A1 | 5/2002 | Jervis |
| 2002/0065524 A1 | 5/2002 | Miller et al. |
| 2002/0066360 A1 | 6/2002 | Greenhalgh et al. |
| 2002/0077652 A1 | 6/2002 | Kieturakis et al. |
| 2002/0082621 A1 | 6/2002 | Schurr et al. |
| 2002/0087170 A1 | 7/2002 | Kuhns et al. |
| 2002/0091405 A1 | 7/2002 | Kieturakis et al. |
| 2002/0103434 A1 | 8/2002 | Swanbom |
| 2002/0103494 A1 | 8/2002 | Pacey |
| 2002/0107539 A1 | 8/2002 | Kieturakis et al. |
| 2002/0116070 A1 | 8/2002 | Amara et al. |
| 2002/0117534 A1 | 8/2002 | Green et al. |
| 2002/0147457 A1 | 10/2002 | Rousseau |
| 2002/0165561 A1 | 11/2002 | Ainsworth et al. |
| 2002/0169452 A1 | 11/2002 | Tormala et al. |
| 2002/0173803 A1 | 11/2002 | Ainsworth et al. |
| 2002/0173804 A1 | 11/2002 | Rousseau |
| 2002/0183765 A1 | 12/2002 | Adams |
| 2002/0183768 A1 | 12/2002 | Deem et al. |
| 2002/0188317 A1 | 12/2002 | Rousseau |
| 2003/0004581 A1 | 1/2003 | Rousseau |
| 2003/0039626 A1 | 2/2003 | Holmes-Farley |
| 2003/0065359 A1 | 4/2003 | Weller et al. |
| 2003/0073976 A1 | 4/2003 | Brushey |
| 2003/0078602 A1 | 4/2003 | Rousseau |
| 2003/0078603 A1 | 4/2003 | Schaller et al. |
| 2003/0105473 A1 | 6/2003 | Miller |
| 2003/0109892 A1 | 6/2003 | Deem et al. |
| 2003/0119985 A1 | 6/2003 | Sehl et al. |
| 2003/0120265 A1 | 6/2003 | Deem et al. |
| 2003/0120299 A1 | 6/2003 | Kieturakis et al. |
| 2003/0130745 A1 | 7/2003 | Cherok et al. |
| 2003/0166628 A1 | 9/2003 | Doyle et al. |
| 2003/0171761 A1 | 9/2003 | Sancoff et al. |
| 2003/0171812 A1 | 9/2003 | Grunberg et al. |
| 2003/0171823 A1 | 9/2003 | Zotti et al. |
| 2003/0187516 A1 | 10/2003 | Amid et al. |
| 2003/0195531 A1 | 10/2003 | Gardiner et al. |
| 2003/0208211 A1 | 11/2003 | Kortenbach |
| 2003/0212460 A1 | 11/2003 | Darois et al. |
| 2003/0212461 A1 | 11/2003 | Vadurro et al. |
| 2003/0212462 A1 | 11/2003 | Gryska et al. |
| 2003/0220660 A1 | 11/2003 | Kortenbach et al. |
| 2003/0225355 A1 | 12/2003 | Butler |
| 2003/0225420 A1 | 12/2003 | Wardle |
| 2004/0002679 A1 | 1/2004 | Trout et al. |
| 2004/0010317 A1 | 1/2004 | Lambrecht et al. |
| 2004/0019360 A1 | 1/2004 | Farnsworth et al. |
| 2004/0024386 A1 | 2/2004 | Deem et al. |
| 2004/0024465 A1 | 2/2004 | Lambrecht et al. |
| 2004/0030217 A1 | 2/2004 | Yeung et al. |
| 2004/0039453 A1 | 2/2004 | Anderson et al. |
| 2004/0044364 A1 | 3/2004 | DeVries et al. |
| 2004/0044412 A1 | 3/2004 | Lambrecht et al. |
| 2004/0049227 A1 | 3/2004 | Jervis |
| 2004/0049282 A1 | 3/2004 | Gjunter |
| 2004/0054376 A1 | 3/2004 | Ory et al. |
| 2004/0059356 A1 | 3/2004 | Gringas |
| 2004/0064131 A1 | 4/2004 | Brushey |
| 2004/0073237 A1 | 4/2004 | Leinsing |
| 2004/0073257 A1 | 4/2004 | Spitz |
| 2004/0082755 A1 | 4/2004 | Erneta et al. |
| 2004/0087970 A1 | 5/2004 | Chu et al. |
| 2004/0087979 A1 | 5/2004 | Field et al. |
| 2004/0087980 A1 | 5/2004 | Ford et al. |
| 2004/0092937 A1 | 5/2004 | Criscuolo et al. |
| 2004/0092969 A1 | 5/2004 | Kumar |
| 2004/0092970 A1 | 5/2004 | Xavier |
| 2004/0097924 A1 | 5/2004 | Lambrecht et al. |
| 2004/0097986 A1 | 5/2004 | Adams |
| 2004/0122452 A1 | 6/2004 | Deem et al. |
| 2004/0122453 A1 | 6/2004 | Deem et al. |
| 2004/0133214 A1 | 7/2004 | Kayan |
| 2004/0144395 A1 | 7/2004 | Evans et al. |
| 2004/0152977 A1 | 8/2004 | Duchon et al. |
| 2004/0152978 A1 | 8/2004 | Duchon et al. |
| 2004/0172048 A1 | 9/2004 | Browning |
| 2004/0181288 A1 | 9/2004 | Darois et al. |
| 2004/0193043 A1 | 9/2004 | Duchon et al. |
| 2004/0215219 A1 | 10/2004 | Eldridge et al. |
| 2004/0225247 A1 | 11/2004 | Pugsley et al. |
| 2004/0225373 A1 | 11/2004 | Pugsley et al. |
| 2004/0230208 A1 | 11/2004 | Shayani |
| 2004/0234576 A1 | 11/2004 | Martin et al. |
| 2004/0249412 A1 | 12/2004 | Snow et al. |
| 2004/0254592 A1 | 12/2004 | DiCarlo et al. |
| 2005/0004427 A1 | 1/2005 | Cervigni |
| 2005/0010239 A1 | 1/2005 | Chefitz |
| 2005/0010306 A1 | 1/2005 | Priewe et al. |
| 2005/0015102 A1 | 1/2005 | Chefitz |
| 2005/0019436 A1 | 1/2005 | Burch et al. |
| 2005/0021058 A1 | 1/2005 | Negro |
| 2005/0027369 A1 | 2/2005 | Eldridge et al. |
| 2005/0033318 A1 | 2/2005 | Miller et al. |
| 2005/0038452 A1 | 2/2005 | Chu |
| 2005/0054771 A1 | 3/2005 | Sehl et al. |
| 2005/0055097 A1 | 3/2005 | Grunberg et al. |
| 2005/0060038 A1 | 3/2005 | Lambrecht et al. |
| 2005/0065072 A1 | 3/2005 | Keeler et al. |
| 2005/0075667 A1 | 4/2005 | Schaller et al. |

(56) References Cited

U.S. PATENT DOCUMENTS

| | | |
|---|---|---|
| 2005/0080454 A1 | 4/2005 | Drews et al. |
| 2005/0113849 A1 | 5/2005 | Popadiuk et al. |
| 2005/0113858 A1 | 5/2005 | Deutsch |
| 2005/0118239 A1 | 6/2005 | Sabesan |
| 2005/0129733 A1 | 6/2005 | Milbocker et al. |
| 2005/0142315 A1 | 6/2005 | DeSimone et al. |
| 2005/0143817 A1 | 6/2005 | Hunter et al. |
| 2005/0149072 A1 | 7/2005 | DeVries et al. |
| 2005/0149080 A1 | 7/2005 | Hunter et al. |
| 2005/0149158 A1 | 7/2005 | Hunter et al. |
| 2005/0154361 A1 | 7/2005 | Sabesan |
| 2005/0159777 A1 | 7/2005 | Spitz |
| 2005/0165425 A1 | 7/2005 | Croce et al. |
| 2005/0165488 A1 | 7/2005 | Hunter et al. |
| 2005/0169959 A1 | 8/2005 | Hunter et al. |
| 2005/0175663 A1 | 8/2005 | Hunter et al. |
| 2005/0177225 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0183728 A1 | 8/2005 | Hunter et al. |
| 2005/0191331 A1 | 9/2005 | Hunter et al. |
| 2005/0192600 A1 | 9/2005 | Nicolo et al. |
| 2005/0202067 A1 | 9/2005 | Lendlein et al. |
| 2005/0222591 A1 | 10/2005 | Gingras et al. |
| 2005/0228408 A1 | 10/2005 | Fricke et al. |
| 2005/0234557 A1 | 10/2005 | Lambrecht et al. |
| 2005/0240269 A1 | 10/2005 | Lambrecht et al. |
| 2005/0244455 A1 | 11/2005 | Greenawalt |
| 2005/0245787 A1 | 11/2005 | Cox et al. |
| 2005/0249770 A1 | 11/2005 | Hunter |
| 2005/0267325 A1 | 12/2005 | Bouchier et al. |
| 2005/0271794 A1 | 12/2005 | DeSimone et al. |
| 2005/0273146 A1 | 12/2005 | DeSimone et al. |
| 2005/0283189 A1 | 12/2005 | Rosenblatt |
| 2005/0283190 A1 | 12/2005 | Huitema et al. |
| 2005/0283246 A1 | 12/2005 | Cauthen et al. |
| 2005/0283962 A1 | 12/2005 | Boudjemline |
| 2005/0288691 A1 | 12/2005 | Leiboff |
| 2005/0288775 A1 | 12/2005 | Dong |
| 2006/0009802 A1 | 1/2006 | Modesitt |
| 2006/0015142 A1 | 1/2006 | Malazgirt |
| 2006/0015143 A1 | 1/2006 | Alvarado |
| 2006/0024238 A1 | 2/2006 | Barth et al. |
| 2006/0025649 A1 | 2/2006 | Smith et al. |
| 2006/0039896 A1 | 2/2006 | Kleinsek et al. |
| 2006/0047180 A1 | 3/2006 | Hegde et al. |
| 2006/0052816 A1 | 3/2006 | Bates et al. |
| 2006/0064175 A1 | 3/2006 | Pelissier et al. |
| 2006/0079558 A1 | 4/2006 | Aberg et al. |
| 2006/0079559 A1 | 4/2006 | Aberg et al. |
| 2006/0083710 A1 | 4/2006 | Joerger et al. |
| 2006/0105026 A1 | 5/2006 | Fortune et al. |
| 2006/0116696 A1 | 6/2006 | Odermatt et al. |
| 2006/0122637 A1 | 6/2006 | Barker |
| 2006/0127353 A1 | 6/2006 | Holmes-Farley |
| 2006/0129152 A1 | 6/2006 | Shipp |
| 2006/0129154 A1 | 6/2006 | Shipp |
| 2006/0142787 A1 | 6/2006 | Weller et al. |
| 2006/0147488 A1 | 7/2006 | Wohlert |
| 2006/0147492 A1 | 7/2006 | Hunter et al. |
| 2006/0149316 A1 | 7/2006 | DeVries et al. |
| 2006/0155165 A1 | 7/2006 | Vanden Hoek et al. |
| 2006/0155379 A1 | 7/2006 | Heneveld et al. |
| 2006/0177489 A1 | 8/2006 | Massouda et al. |
| 2006/0189918 A1 | 8/2006 | Barker |
| 2006/0200246 A1 | 9/2006 | Lambrecht et al. |
| 2006/0206118 A1 | 9/2006 | Kim et al. |
| 2006/0206178 A1 | 9/2006 | Kim |
| 2006/0210602 A1 | 9/2006 | Sehl et al. |
| 2006/0217812 A1 | 9/2006 | Lambrecht et al. |
| 2006/0228391 A1 | 10/2006 | Seyedin et al. |
| 2006/0233852 A1 | 10/2006 | Milbocker |
| 2006/0240063 A9 | 10/2006 | Hunter et al. |
| 2006/0251702 A1 | 11/2006 | Janis et al. |
| 2006/0253203 A1 | 11/2006 | Alvarado |
| 2006/0264698 A1 | 11/2006 | Kondonis et al. |
| 2006/0282103 A1 | 12/2006 | Fricke et al. |
| 2006/0282105 A1 | 12/2006 | Ford et al. |
| 2006/0287729 A1 | 12/2006 | Segal et al. |
| 2006/0287730 A1 | 12/2006 | Segal et al. |
| 2007/0016300 A1 | 1/2007 | Kuslich |
| 2007/0021756 A1 | 1/2007 | Kortenbach |
| 2007/0026043 A1 | 2/2007 | Guan et al. |
| 2007/0027358 A1 | 2/2007 | Gertner et al. |
| 2007/0032881 A1 | 2/2007 | Browning |
| 2007/0036876 A1 | 2/2007 | Burch et al. |
| 2007/0038220 A1 | 2/2007 | Shipp |
| 2007/0038310 A1 | 2/2007 | Guetty |
| 2007/0100355 A1 | 5/2007 | Bonde et al. |
| 2007/0110786 A1 | 5/2007 | Tenney et al. |
| 2007/0111937 A1 | 5/2007 | Pickar et al. |
| 2007/0118133 A1 | 5/2007 | Lambrecht et al. |
| 2007/0118158 A1 | 5/2007 | Deem et al. |
| 2007/0118159 A1 | 5/2007 | Deem et al. |
| 2007/0122425 A1 | 5/2007 | Keeler et al. |
| 2007/0134292 A1 | 6/2007 | Suokas et al. |
| 2007/0135929 A1 | 6/2007 | Williams et al. |
| 2007/0156245 A1 | 7/2007 | Cauthen et al. |
| 2007/0162030 A1 | 7/2007 | Aranyi et al. |
| 2007/0162135 A1 | 7/2007 | Segal et al. |
| 2007/0167963 A1 | 7/2007 | Deem et al. |
| 2007/0173864 A1 | 7/2007 | Chu |
| 2007/0173888 A1 | 7/2007 | Gertner et al. |
| 2007/0179335 A1 | 8/2007 | Gertner et al. |
| 2007/0184277 A1 | 8/2007 | Schussler et al. |
| 2007/0185506 A1* | 8/2007 | Jackson ................ 606/151 |
| 2007/0185541 A1 | 8/2007 | DiUbaldi et al. |
| 2007/0198040 A1 | 8/2007 | Buevich et al. |
| 2007/0202148 A1 | 8/2007 | Ringeisen et al. |
| 2007/0202173 A1 | 8/2007 | Cueto-Garcia |
| 2007/0203507 A1 | 8/2007 | McLaughlin et al. |
| 2007/0207186 A1 | 9/2007 | Scanlon et al. |
| 2007/0208358 A1 | 9/2007 | Kayan |
| 2007/0219569 A1 | 9/2007 | Shayani |
| 2007/0225791 A1 | 9/2007 | Molitor et al. |
| 2007/0244502 A1 | 10/2007 | Deutsch |
| 2007/0250147 A1 | 10/2007 | Walther et al. |
| 2007/0260179 A1 | 11/2007 | Sholev et al. |
| 2007/0260268 A1 | 11/2007 | Bartee et al. |
| 2007/0265710 A1 | 11/2007 | Brown et al. |
| 2007/0270752 A1 | 11/2007 | LaBombard |
| 2007/0280990 A1 | 12/2007 | Stopek |
| 2007/0293717 A1 | 12/2007 | Kaleta et al. |
| 2007/0293878 A1 | 12/2007 | Butsch |
| 2007/0299300 A1 | 12/2007 | Smith et al. |
| 2007/0299542 A1 | 12/2007 | Mathisen et al. |
| 2008/0015501 A1 | 1/2008 | Gertner |
| 2008/0021545 A1 | 1/2008 | Reneker et al. |
| 2008/0033461 A1 | 2/2008 | Koeckerling et al. |
| 2008/0035243 A1 | 2/2008 | Breitenkamp et al. |
| 2008/0045952 A1 | 2/2008 | Kuslich |
| 2008/0065229 A1 | 3/2008 | Adams |
| 2008/0086216 A1 | 4/2008 | Wilson et al. |
| 2008/0091222 A1 | 4/2008 | Deusch et al. |
| 2008/0091276 A1 | 4/2008 | Deusch et al. |
| 2008/0103351 A1 | 5/2008 | Montpetit et al. |
| 2008/0113035 A1 | 5/2008 | Hunter |
| 2008/0125869 A1 | 5/2008 | Paz et al. |
| 2008/0131509 A1 | 6/2008 | Hossainy et al. |
| 2008/0132602 A1 | 6/2008 | Rizk et al. |
| 2008/0147198 A1 | 6/2008 | Cherok et al. |
| 2008/0147200 A1 | 6/2008 | Rousseau et al. |
| 2008/0167519 A1 | 7/2008 | St-Germain |
| 2008/0167667 A1 | 7/2008 | Criscuolo et al. |
| 2008/0167668 A1 | 7/2008 | Criscuolo et al. |
| 2008/0188874 A1* | 8/2008 | Henderson ................ 606/151 |
| 2008/0193494 A1 | 8/2008 | Sabesan |
| 2008/0195121 A1 | 8/2008 | Eldar et al. |
| 2008/0200979 A1 | 8/2008 | Dieck et al. |
| 2008/0215154 A1 | 9/2008 | Lambrecht et al. |
| 2008/0243149 A1 | 10/2008 | Kockerling et al. |
| 2008/0255593 A1 | 10/2008 | St-Germain |
| 2008/0260794 A1 | 10/2008 | Lauritzen et al. |

(56) References Cited

U.S. PATENT DOCUMENTS

| | | | |
|---|---|---|---|
| 2008/0269896 A1 | 10/2008 | Cherok et al. | |
| 2008/0281433 A1 | 11/2008 | Chang et al. | |
| 2008/0287970 A1 | 11/2008 | Amato et al. | |
| 2008/0306497 A1 | 12/2008 | Brown et al. | |
| 2008/0312751 A1 | 12/2008 | Pugsley et al. | |
| 2009/0004239 A1 | 1/2009 | Ladet et al. | |
| 2009/0005867 A1 | 1/2009 | Lefranc et al. | |
| 2009/0012350 A1 | 1/2009 | Tihon | |
| 2009/0012546 A1 | 1/2009 | N'diaye et al. | |
| 2009/0018559 A1 | 1/2009 | Buevich et al. | |
| 2009/0030434 A1 | 1/2009 | Paz et al. | |
| 2009/0030522 A1 | 1/2009 | Cauthen, III et al. | |
| 2009/0030527 A1 | 1/2009 | Richter | |
| 2009/0036937 A1 | 2/2009 | Cauthen, III et al. | |
| 2009/0036989 A1 | 2/2009 | Cauthen, III et al. | |
| 2009/0036990 A1 | 2/2009 | Cauthen, III et al. | |
| 2009/0036996 A1 | 2/2009 | Roeber | |
| 2009/0062823 A1 | 3/2009 | Richter | |
| 2009/0069826 A1 | 3/2009 | Walther et al. | |
| 2009/0105526 A1 | 4/2009 | Pirolli Torelli et al. | |
| 2009/0125041 A1 | 5/2009 | Dudai | |
| 2009/0137864 A1 | 5/2009 | Cox et al. | |
| 2009/0149875 A1 | 6/2009 | Abele et al. | |
| 2009/0155332 A1 | 6/2009 | Sherry et al. | |
| 2009/0157184 A1 | 6/2009 | Cauthen, III et al. | |
| 2009/0157195 A1 | 6/2009 | Siedle | |
| 2009/0162273 A1 | 6/2009 | Lawrynowicz et al. | |
| 2009/0182190 A1 | 7/2009 | Dann | |
| 2009/0182352 A1 | 7/2009 | Paz et al. | |
| 2009/0187258 A1 | 7/2009 | Ip et al. | |
| 2009/0192346 A1 | 7/2009 | Rosenblatt | |
| 2009/0192528 A1 | 7/2009 | Higgins et al. | |
| 2009/0198260 A1 | 8/2009 | Ford et al. | |
| 2009/0204130 A1 | 8/2009 | Kantsevoy et al. | |
| 2009/0204227 A1 | 8/2009 | Derwin et al. | |
| 2009/0216075 A1 | 8/2009 | Bell et al. | |
| 2009/0216104 A1 | 8/2009 | DeSimone et al. | |
| 2009/0216264 A1* | 8/2009 | Friedman et al. | 606/213 |
| 2009/0216338 A1 | 8/2009 | Gringas et al. | |
| 2009/0234379 A1 | 9/2009 | Rehnke | |
| 2009/0234461 A1 | 9/2009 | Rehnke | |
| 2009/0240342 A1 | 9/2009 | Lindh et al. | |
| 2009/0240343 A1 | 9/2009 | Adams | |
| 2009/0248048 A1 | 10/2009 | Milbocker | |
| 2009/0254103 A1 | 10/2009 | Deutsch | |
| 2009/0259094 A1 | 10/2009 | Bouchier et al. | |
| 2009/0281563 A1 | 11/2009 | Newell et al. | |
| 2010/0069930 A1 | 3/2010 | Roslin et al. | |
| 2010/0292718 A1* | 11/2010 | Sholev et al. | 606/151 |
| 2010/0312357 A1* | 12/2010 | Levin et al. | 623/23.72 |
| 2011/0112560 A1* | 5/2011 | Sholev | 606/151 |

FOREIGN PATENT DOCUMENTS

| | | |
|---|---|---|
| EP | 0525791 A1 | 2/1993 |
| EP | 0537769 A1 | 4/1993 |
| EP | 0544485 A1 | 6/1993 |
| EP | 0556018 A1 | 8/1993 |
| EP | 0557963 A1 | 9/1993 |
| EP | 0557964 A1 | 9/1993 |
| EP | 0573273 A2 | 12/1993 |
| EP | 0579377 A2 | 1/1994 |
| EP | 0581036 | 2/1994 |
| EP | 0581036 A1 | 2/1994 |
| EP | 0614650 A2 | 9/1994 |
| EP | 0702934 A1 | 3/1996 |
| EP | 0744162 A2 | 11/1996 |
| EP | 0519022 B1 | 12/1997 |
| EP | 0827724 A2 | 3/1998 |
| EP | 0553344 B1 | 9/1998 |
| EP | 0746258 B1 | 9/1998 |
| EP | 0898944 A2 | 3/1999 |
| EP | 0908482 A1 | 4/1999 |
| EP | 0986993 A1 | 3/2000 |
| EP | 0837660 B1 | 5/2000 |
| EP | 1060714 A2 | 12/2000 |
| EP | 1145693 A2 | 10/2001 |
| EP | 1181899 A2 | 2/2002 |
| EP | 1199037 A2 | 4/2002 |
| EP | 1199038 A2 | 4/2002 |
| EP | 1219265 A2 | 7/2002 |
| EP | 0746267 B1 | 11/2002 |
| EP | 1018980 B1 | 1/2003 |
| EP | 1306061 A2 | 5/2003 |
| EP | 1317904 A1 | 6/2003 |
| EP | 1366717 A1 | 12/2003 |
| EP | 0783270 B1 | 6/2004 |
| EP | 1200010 B1 | 3/2005 |
| EP | 1164967 B1 | 5/2005 |
| EP | 1541183 A1 | 6/2005 |
| EP | WO2005082273 A1 | 9/2005 |
| EP | 0828453 B1 | 11/2005 |
| EP | 1001717 B1 | 11/2005 |
| EP | 1303230 B1 | 11/2005 |
| EP | 1607048 A1 | 12/2005 |
| EP | 1404250 B1 | 2/2006 |
| EP | 1671604 A2 | 6/2006 |
| EP | 1674048 A1 | 6/2006 |
| EP | 1274473 B1 | 7/2006 |
| EP | 0934024 B1 | 8/2006 |
| EP | 1503683 B1 | 8/2006 |
| EP | 1700579 A1 | 9/2006 |
| EP | 1704832 A2 | 9/2006 |
| EP | 200614650 A2 | 10/2006 |
| EP | 1079741 B1 | 11/2006 |
| EP | 0964645 B1 | 7/2007 |
| EP | 1163019 B1 | 10/2007 |
| EP | 1849440 A1 | 10/2007 |
| EP | 1867348 A2 | 12/2007 |
| EP | 1870056 A1 | 12/2007 |
| EP | 1531739 B1 | 2/2008 |
| EP | 1406557 B1 | 11/2008 |
| EP | 1990014 A2 | 11/2008 |
| EP | 2002800 A1 | 12/2008 |
| EP | 1505927 B1 | 1/2009 |
| EP | 1372525 B1 | 3/2009 |
| EP | 1653880 B1 | 4/2009 |
| EP | 2050474 A2 | 4/2009 |
| EP | 1940312 B1 | 7/2009 |
| FR | 2789888 | 8/2000 |
| FR | 2789888 A1 | 8/2000 |
| WO | WO1982004390 A1 | 12/1982 |
| WO | WO92/06639 | 4/1992 |
| WO | WO1992006639 A2 | 4/1992 |
| WO | WO199211824 A1 | 7/1992 |
| WO | WO1992019162 A2 | 11/1992 |
| WO | WO1992021293 A1 | 12/1992 |
| WO | WO1993003685 A1 | 3/1993 |
| WO | WO199309722 A1 | 5/1993 |
| WO | WO1993017635 A1 | 9/1993 |
| WO | WO1994017747 A1 | 8/1994 |
| WO | WO1994019029 A1 | 9/1994 |
| WO | WO94/27535 | 12/1994 |
| WO | WO199427535 A1 | 12/1994 |
| WO | WO199531140 A1 | 11/1995 |
| WO | WO1995030374 A1 | 11/1995 |
| WO | WO1996003091 A1 | 2/1996 |
| WO | WO1996003165 A1 | 2/1996 |
| WO | WO1996006634 A1 | 3/1996 |
| WO | WO1996009795 A1 | 4/1996 |
| WO | WO199640307 A1 | 12/1996 |
| WO | WO1997002789 A1 | 1/1997 |
| WO | WO1997022371 A1 | 6/1997 |
| WO | WO1997032526 A1 | 9/1997 |
| WO | WO1997035533 A1 | 10/1997 |
| WO | WO1998003713 A1 | 1/1998 |
| WO | WO1998011814 | 3/1998 |
| WO | WO199814134 A2 | 4/1998 |
| WO | WO1998016153 A1 | 4/1998 |
| WO | WO1999003422 A1 | 1/1999 |
| WO | WO1999005992 A1 | 2/1999 |
| WO | WO1999016381 A1 | 4/1999 |
| WO | WO1999051163 A1 | 10/1999 |
| WO | WO199963051 A2 | 12/1999 |

(56) References Cited

FOREIGN PATENT DOCUMENTS

| | | |
|---|---|---|
| WO | WO1999060931 A1 | 12/1999 |
| WO | WO1999062406 A2 | 12/1999 |
| WO | WO2000007520 A1 | 2/2000 |
| WO | WO2000016822 A2 | 3/2000 |
| WO | WO2000056376 A1 | 9/2000 |
| WO | WO2000057796 A1 | 10/2000 |
| WO | WO2000057812 A1 | 10/2000 |
| WO | WO2000061033 | 10/2000 |
| WO | WO2000067663 A1 | 11/2000 |
| WO | WO2000071548 A1 | 11/2000 |
| WO | WO2000071549 A1 | 11/2000 |
| WO | WO200108594 A1 | 2/2001 |
| WO | WO2001026588 A2 | 4/2001 |
| WO | WO200154589 A1 | 8/2001 |
| WO | WO2001068653 A1 | 9/2001 |
| WO | WO2001070322 A1 | 9/2001 |
| WO | WO200189390 A1 | 11/2001 |
| WO | WO2001080788 A2 | 11/2001 |
| WO | WO2001085058 A2 | 11/2001 |
| WO | WO2001085060 | 11/2001 |
| WO | WO2001089392 A2 | 11/2001 |
| WO | WO2002007648 A1 | 1/2002 |
| WO | WO200217797 A1 | 3/2002 |
| WO | WO2002017771 A2 | 3/2002 |
| WO | WO2002017796 A1 | 3/2002 |
| WO | WO2002019916 A1 | 3/2002 |
| WO | WO2002019923 A1 | 3/2002 |
| WO | WO2002022047 A1 | 3/2002 |
| WO | WO2002024080 A2 | 3/2002 |
| WO | WO200232346 A1 | 4/2002 |
| WO | WO2002026747 A1 | 4/2002 |
| WO | WO2002030336 A2 | 4/2002 |
| WO | WO200234140 A2 | 5/2002 |
| WO | WO2002035990 A2 | 5/2002 |
| WO | WO2002058543 A2 | 8/2002 |
| WO | WO2002078568 A1 | 10/2002 |
| WO | WO2002080779 A1 | 10/2002 |
| WO | WO2002080780 A1 | 10/2002 |
| WO | WO02/091953 | 11/2002 |
| WO | WO2002087425 A2 | 11/2002 |
| WO | WO2002091928 A1 | 11/2002 |
| WO | WO2002091953 A1 | 11/2002 |
| WO | WO2002096327 A2 | 12/2002 |
| WO | WO2003002029 A1 | 1/2003 |
| WO | WO2003002130 A1 | 1/2003 |
| WO | WO2003032867 A1 | 4/2003 |
| WO | WO2003059180 A2 | 7/2003 |
| WO | WO2003059201 A1 | 7/2003 |
| WO | WO2003059217 A1 | 7/2003 |
| WO | WO2003077730 A2 | 9/2003 |
| WO | WO2003082125 A1 | 10/2003 |
| WO | WO2003084410 A1 | 10/2003 |
| WO | WO2003088846 A1 | 10/2003 |
| WO | WO2003090633 A2 | 11/2003 |
| WO | WO2003092509 A1 | 11/2003 |
| WO | WO2003094781 A1 | 11/2003 |
| WO | WO2003094783 A1 | 11/2003 |
| WO | WO2003094786 A1 | 11/2003 |
| WO | WO2003094787 A1 | 11/2003 |
| WO | WO2003096909 A1 | 11/2003 |
| WO | WO2003096929 A1 | 11/2003 |
| WO | WO2003097011 A1 | 11/2003 |
| WO | WO2003099160 A1 | 12/2003 |
| WO | WO2003103473 A2 | 12/2003 |
| WO | WO2004004600 A1 | 1/2004 |
| WO | WO2004006808 A2 | 1/2004 |
| WO | WO2004/012579 | 2/2004 |
| WO | WO200412579 A2 | 2/2004 |
| WO | WO2004012627 A1 | 2/2004 |
| WO | WO2004019787 A2 | 3/2004 |
| WO | WO2004024030 A1 | 3/2004 |
| WO | WO2004034924 A2 | 4/2004 |
| WO | WO2004037123 A1 | 5/2004 |
| WO | WO2004/062529 | 7/2004 |
| WO | WO2004058286 A1 | 7/2004 |
| WO | WO2004060425 A2 | 7/2004 |
| WO | WO2004062529 A2 | 7/2004 |
| WO | WO2004062530 A1 | 7/2004 |
| WO | WO2004028547 A1 | 8/2004 |
| WO | WO2004069866 A1 | 8/2004 |
| WO | WO2004/080348 | 9/2004 |
| WO | WO2004080348 A1 | 9/2004 |
| WO | WO2004087227 A1 | 10/2004 |
| WO | WO2004093737 A1 | 11/2004 |
| WO | WO2004098461 A2 | 11/2004 |
| WO | WO2004098665 A1 | 11/2004 |
| WO | WO2004100841 A1 | 11/2004 |
| WO | WO2004101002 A2 | 11/2004 |
| WO | WO2004103166 A2 | 12/2004 |
| WO | WO2004103414 A2 | 12/2004 |
| WO | WO2005003351 A1 | 1/2005 |
| WO | WO2005004727 A1 | 1/2005 |
| WO | WO2005007209 A1 | 1/2005 |
| WO | WO2005014634 A1 | 2/2005 |
| WO | WO2005018494 A1 | 3/2005 |
| WO | WO2005019241 A2 | 3/2005 |
| WO | WO2005019315 A1 | 3/2005 |
| WO | WO2005035548 A1 | 4/2005 |
| WO | WO2005041784 A2 | 5/2005 |
| WO | WO2005044143 A1 | 5/2005 |
| WO | WO2005051172 A2 | 6/2005 |
| WO | WO2005055958 A2 | 6/2005 |
| WO | WO2005065324 A2 | 7/2005 |
| WO | WO2005065552 A2 | 7/2005 |
| WO | WO2005079335 A2 | 9/2005 |
| WO | WO2005082274 A1 | 9/2005 |
| WO | WO2005094721 A1 | 10/2005 |
| WO | WO2005099628 A2 | 10/2005 |
| WO | WO2005102209 A1 | 11/2005 |
| WO | WO2005105172 A1 | 11/2005 |
| WO | WO2005110243 A2 | 11/2005 |
| WO | WO2005110273 A1 | 11/2005 |
| WO | WO2006002439 A1 | 1/2006 |
| WO | WO2006008429 A1 | 1/2006 |
| WO | WO2006012353 A2 | 2/2006 |
| WO | WO2006013337 A2 | 2/2006 |
| WO | WO2006015031 A2 | 2/2006 |
| WO | WO2006026509 A2 | 3/2006 |
| WO | WO2006034117 A1 | 3/2006 |
| WO | WO2006036936 A2 | 4/2006 |
| WO | WO2006037047 A2 | 4/2006 |
| WO | WO2006040760 A2 | 4/2006 |
| WO | WO2006044785 A1 | 4/2006 |
| WO | WO2006047645 A2 | 5/2006 |
| WO | WO2006048885 A1 | 5/2006 |
| WO | WO2006082587 A2 | 8/2006 |
| WO | WO2006086339 A2 | 8/2006 |
| WO | WO2006092159 A1 | 9/2006 |
| WO | WO2006092236 A1 | 9/2006 |
| WO | WO2006102457 A2 | 9/2006 |
| WO | WO2006116000 A2 | 11/2006 |
| WO | WO2006119034 A2 | 11/2006 |
| WO | WO2007/004228 | 1/2007 |
| WO | WO2007004228 A1 | 1/2007 |
| WO | WO2007011689 A2 | 1/2007 |
| WO | WO2007017872 A2 | 2/2007 |
| WO | WO2007021620 A2 | 2/2007 |
| WO | WO2007021759 A2 | 2/2007 |
| WO | WO2007021834 A1 | 2/2007 |
| WO | WO2007/025302 | 3/2007 |
| WO | WO2007/030676 | 3/2007 |
| WO | WO2007025293 A2 | 3/2007 |
| WO | WO2007025296 A2 | 3/2007 |
| WO | WO2007025302 A2 | 3/2007 |
| WO | WO2007030676 A2 | 3/2007 |
| WO | WO2007034145 A2 | 3/2007 |
| WO | WO2007050382 A2 | 5/2007 |
| WO | WO2007051221 A1 | 5/2007 |
| WO | WO2007055755 A1 | 5/2007 |
| WO | WO2007070141 A1 | 6/2007 |
| WO | WO2007072469 A2 | 6/2007 |
| WO | WO2007081955 A1 | 7/2007 |
| WO | WO2007087132 A1 | 8/2007 |
| WO | WO2007087146 A2 | 8/2007 |

(56) References Cited

FOREIGN PATENT DOCUMENTS

| | | |
|---|---|---|
| WO | WO2007115110 A2 | 10/2007 |
| WO | WO2007129220 A2 | 11/2007 |
| WO | WO2007133311 A2 | 11/2007 |
| WO | WO2007136820 A2 | 11/2007 |
| WO | WO2007137211 A2 | 11/2007 |
| WO | WO2007143726 A2 | 12/2007 |
| WO | WO2007144782 A2 | 12/2007 |
| WO | WO2007146784 A2 | 12/2007 |
| WO | WO2008006097 A2 | 1/2008 |
| WO | WO2008016802 A1 | 2/2008 |
| WO | WO2008026905 A2 | 3/2008 |
| WO | WO2008030873 A2 | 3/2008 |
| WO | WO2008030939 A2 | 3/2008 |
| WO | WO2008/045635 | 4/2008 |
| WO | WO2008045635 A2 | 4/2008 |
| WO | WO2008055028 A1 | 5/2008 |
| WO | WO2008/065653 | 6/2008 |
| WO | WO2008065653 A1 | 6/2008 |
| WO | WO2008069919 A2 | 6/2008 |
| WO | WO2008083484 A1 | 7/2008 |
| WO | WO2008085825 A1 | 7/2008 |
| WO | WO2008/099382 | 8/2008 |
| WO | WO2008094217 A1 | 8/2008 |
| WO | WO2008094842 A1 | 8/2008 |
| WO | WO2008099382 A1 | 8/2008 |
| WO | WO2008112437 A2 | 9/2008 |
| WO | WO2008124056 A1 | 10/2008 |
| WO | WO2008140989 A2 | 11/2008 |
| WO | WO2008157497 A2 | 12/2008 |
| WO | WO2008157777 A1 | 12/2008 |
| WO | WO2009005625 A1 | 1/2009 |
| WO | WO2009005634 A1 | 1/2009 |
| WO | WO2009011824 A1 | 1/2009 |
| WO | WO2009012001 A1 | 1/2009 |
| WO | WO2009022348 A1 | 2/2009 |
| WO | WO2009036094 A2 | 3/2009 |
| WO | WO2009039371 A1 | 3/2009 |
| WO | WO2009/050717 | 4/2009 |
| WO | WO2009042442 A1 | 4/2009 |
| WO | WO2009048314 A1 | 4/2009 |
| WO | WO2009050717 A2 | 4/2009 |
| WO | WO2009059005 A1 | 5/2009 |
| WO | WO2009064845 A2 | 5/2009 |
| WO | WO2009069119 A1 | 6/2009 |
| WO | WO2009075786 A1 | 6/2009 |
| WO | WO2009075932 A1 | 6/2009 |
| WO | WO2009075933 A1 | 6/2009 |
| WO | WO2009086446 A1 | 7/2009 |
| WO | WO2009092294 A1 | 7/2009 |
| WO | WO2009094015 A1 | 7/2009 |
| WO | WO2009/104182 | 8/2009 |
| WO | WO2009097380 A1 | 8/2009 |
| WO | WO2009102792 A2 | 8/2009 |
| WO | WO2009104182 A2 | 8/2009 |
| WO | WO2009113972 A2 | 9/2009 |
| WO | WO2009126781 A1 | 10/2009 |
| WO | 2011/021082 A1 | 2/2011 |

OTHER PUBLICATIONS

Merriam-Webster Dictionary, http://www.merriam-webster.com/dictionary/fixed as accessed on Jul. 30, 2015.*

Canadian Office Action dated May 4, 2016 in corresponding Canadian Application No. 2,769,666.

Extended European Search Report from Application No. EP 10809595.1-1506 dated Aug. 25, 2015.

* cited by examiner

MEANS AND METHOD FOR REVERSIBLY CONNECTING AN IMPLANT TO A DEPLOYMENT DEVICE

RELATED APPLICATION

The present application claims the benefit of and priority to U.S. provisional patent application Ser. No. 61/234,407, filed Aug. 17, 2009, the content of which is incorporated by reference herein in its entirety.

FIELD OF THE INVENTION

This invention generally relates to devices and methods for reversibly coupling an implant to a deployment device.

BACKGROUND

An object of the present invention is to provide apparatus and a method for performing corrective surgery on internal wounds such as hernia where invasion of the patient's body tissues is minimized and resultant trauma is reduced.

A hernia is a protrusion of a tissue, structure, or part of an organ through the muscular tissue or the membrane by which it is normally contained. In other words a hernia is a defect in the abdominal wall through which a portion of the intra-abdominal contents can protrude. This often causes discomfort and an unsightly, visible bulge in the abdomen. When such a hernia defect occurs in the abdominal region, conventional corrective surgery has required opening the abdominal cavity by surgical incision through the major abdominal muscles. While this technique provides for effective corrective surgery of the hernia defect, it has the disadvantage of requiring a hospital stay of as much as a week, during which pain is frequently intense, and it requires an extended period of recuperation. After the conventional surgery patients frequently cannot return to a full range of activity and work schedule for a month or more. Accordingly, medical science has sought alternative techniques that are less traumatic to the patient and provide for more rapid recovery.

Laparoscopy is the science of introducing a viewing instrument through a port into a patient's body, typically the abdominal cavity, to view its contents. This technique has been used for diagnostic purposes for more than 75 years. Operative laparoscopy is performed through tiny openings in the abdominal wall called ports. In most surgical techniques several ports, frequently three to six, are used. Through one port is inserted the viewing device, which conventionally comprises a fiber optic rod or bundle having a video camera affixed to the outer end to receive and display images from inside the body. The various surgical instruments are inserted through other ports to do the surgery that normally would be performed through an open incision through the abdominal wall. Because the laparoscopic surgical techniques require only very small holes through the abdominal wall or other portions of the body, a patient undergoing such surgery may frequently leave the hospital within one day after the surgery and resume a full range of normal activities within a few days thereafter.

In repairing hernia the physician needs to first deploy the patch and then to attach the patch to the tissue.

There are many patents and patent applications relating to attaching a prosthesis implant to a tissue via tacks. Each patent and patent application describes a different attachment mechanism via different anchoring means (see for example U.S. Pat. No. 6,447,524). Traditional anchors used in surgery include clips, staples, or sutures, and may also be referred to as tissue anchors. These devices are usually made of a biocompatible material (or are coated with a biocompatible material), so that they can be safely implanted into the body.

Most tissue anchors secure the tissue by impaling it with one or more posts or legs that are bent or crimped to lock the tissue into position. Thus, most traditional anchors are rigid or are inflexibly attached to the tissue. For example PCT no. WO07/021834 describes an anchor having two curved legs that cross in a single turning direction to form a loop. Those two curved legs are adapted to penetrate tissue in a curved pathway. U.S. Pat. No. 4,485,816 (refers hereinafter as 816') describes surgical staple made of shape memory alloy. The staple is placed in contact of the tissue and then heated. The heating causes the staple to change its shape thus, penetrating the tissue.

U.S. Pat. No. 6,893,452 describes a tissue attachment device that facilitates wound healing by holding soft tissue together under improved distribution of tension and with minimal disruption of the wound interface and its nutrient supplies.

U.S. Pat. No. 6,517,584 describes a hernia patch which includes at least one anchoring device made of shape memory material. The anchoring devices are initially secured to the prosthesis by being interlaced through a web mesh constituting the prosthesis. The attachment is obtained by altering the attachment element's shape from rectilinear to a loop shape due to heat induced shape memory effect.

Yet other patent literature relates to devices for endoscopic application of surgical staples adapted to attach surgical mesh to a body tissue.

An example of such a teaching is to be found in U.S. Pat. No. 5,364,004, U.S. Pat. No. 5,662,662, U.S. Pat. No. 5,634,584, U.S. Pat. No. 5,560,224, U.S. Pat. No. 5,588,581 and in U.S. Pat. No. 5,626,587.

There are a few patent and patent applications teaching the deployment of patches. For example U.S. Pat. No. 5,836,961 which relates to an apparatus used for developing an anatomic space for laparoscopic hernia repair and a patch for use therewith. The apparatus of U.S. Pat. No. 5,836,961 comprises a tubular introducer member having a bore extending therethrough. A tunneling shaft is slidably mounted in the bore and has proximal and distal extremities including a bullet-shaped tip. A rounded tunneling member is mounted on the distal extremity of the tunneling shaft. The apparatus comprises an inflatable balloon. Means is provided on the balloon for removably securing the balloon to the tunneling shaft. Means is also provided for forming a balloon inflation lumen for inflating the balloon. The balloon is wrapped on the tunneling shaft. A sleeve substantially encloses the balloon and is carried by the tunneling shaft. The sleeve is provided with a weakened region extending longitudinally thereof, permitting the sleeve to be removed whereby the balloon can be unwrapped and inflated so that it lies generally in a plane. The balloon as it is being inflated creates forces generally perpendicular to the plane of the balloon to cause pulling apart of the tissue along a natural plane to provide the anatomic space.

More patent literature can be found in PCT no. WO08065653 which relates to a device especially adapted to deploy a patch within a body cavity. The device is an elongate open-bored applicator (EOBP) and comprises (a) at least one inflatable contour-balloon, (b) at least one inflatable dissection balloon. The inflatable contour-balloon and the inflatable dissection balloon are adjustable and located at the distal portion. The EOBP additionally comprises (c) at least one actuating means located at the proximal portion. The actuating means is in communication with the inflatable contour-balloon and the inflatable dissection balloon. The actuating means is adapted to provide the inflatable contour-balloon and the inflatable dissection balloon with independent activation and/or de-activation.

Although all the above described patents and patent applications demonstrate attachment means or deployment means, none of the literature found relates to a reversible connection device which enable a reversible coupling between the patch and the patch deployment device.

Thus, there is still a long felt need for a device that will enable a reversible connection between the patch and the patch deployment device.

SUMMARY OF THE INVENTION

It is one object of the present invention to provide a detachment mechanism adapted to detach a patch coupled to a patch deployment device (PDD); wherein said detachment mechanism comprises at least one crescent shaped connection clip (CC) comprising:
  a. an elastic crescent shaped body 222 coupled to said PDD;
  b. at least one protruding portion 201 coupled to said body, adapted to protrude out of said PDD; said protruding portion 201 comprising at least one sharp end adapted to penetrate said patch; said protruding portion 201 is characterized by at least two configurations: (i) an attached configuration in which said protruding portion 201 penetrates said patch and positioned substantially parallel to said patch such that an attachment between said PDD and said patch is provided; and (ii) a detached configuration in which said protruding portion 201 emerges out of said patch and positioned substantially perpendicular to said patch such that said detachment between said PDD and said patch is provided.

It is another object of the present invention to provide the detachment mechanism as defined above, wherein application of vertical forces on said CC reconfigure said protruding portion 201 from said attached configuration to said detached configuration.

It is another object of the present invention to provide a detachment mechanism adapted to detach a patch from a patch deployment device (PDD), wherein said mechanism comprising at least one crescent shaped connection clip (CC); each of which comprises:
  a. an elastic crescent shaped body 222 coupled to the distal portion said PDD;
  b. at least one protruding portion 201 coupled to said body, adapted to protrude out of said PDD; said protruding portion 201 comprising at least one sharp end adapted to be penetrate said patch;
    said distal portion of said PDD is characterized by at least two configurations: (i) an attached configuration in which said distal portion is un-deformed such that said protruding portion 201 penetrates said patch and positioned substantially parallel to said patch and an attachment between said PDD and said patch is provided; and (ii) a detached configuration in which said distal portion is deformed such that said protruding portion 201 emerges out of said patch and said detachment between said PDD and said patch is provided.
is another object of the present invention to provide the detachment mechanism as defined above, wherein application of vertical forces on said distal portion reconfigure said distal portion of said PDD from said attached configuration to said detached configuration.

It is another object of the present invention to provide the detachment mechanism as defined above, wherein said detached configuration of said distal portion of said PDD is characterized by bending said distal portion of said PDD.

It is another object of the present invention to provide the detachment mechanism as defined above, wherein said detachment mechanism comprising at least one pair of application of said crescent shaped connection clip (CC); further wherein said vertical forces applied on said distal portion approximates at least two protruding portions of said pair of CC such that said protruding portion 201 emerges out of said patch and said detachment between said PDD and said patch is provided.

It is another object of the present invention to provide the detachment mechanism as defined above, comprising at least one pair of said crescent shaped connection clip (CC); each of which comprises:
  a. a crescent shaped body 222 coupled to said PDD;
  b. at least one protruding portion 201 coupled to said body, adapted to protrude out of said PDD; said protruding portion 201 is characterized by at least sharp end adapted to be penetrate said patch;
    wherein said pair of said protruding portion 201 are aligned, such that application of opposite linear forces provides said detachment between said patch and said PDD.

It is another object of the present invention to provide the detachment mechanism as defined above, wherein the shaped of said portion 201 of said CC is bended such that said portion 201 is adapted to face said PDD.

It is another object of the present invention to provide the detachment mechanism as defined above, wherein said CC additionally comprising a slide prevention section (SPS) 203 adapted to prevent early detachment of said patch from said PDD.

It is another object of the present invention to provide a clip for reversibly attaching a patch to a patch deployment device (PDD), said clip is characterized by a predetermined U-shaped body; said body is characterized by a main longitudinal axis, and comprising a distal end and a proximal end, said distal end comprising a pre-shaped protruding portion 201 in which said portion 201 is substantially parallel to said main longitudinal axis;
  said proximal end comprising a securing portion 301 coupled to said body; said securing portion 301 is adapted to secure said clip to said PDD;
  said protruding portion 201 comprising at least sharp end adapted to be penetrate said patch;
  said protruding portion 201 is characterized by at least two configurations: (i) said pre-shaped configuration in which said attachment between said patch and said PDD is provided; and, (ii) a deformed configuration in which said protruding portion 201 are deformed from said pre-shaped configuration such that detachment between said patch and said PDD is provided.

It is another object of the present invention to provide the clip as defined above, wherein application of vertical forces on said protruding portion 201 reconfigure said protruding portion 201 from said pre-shaped configuration to said deformed configuration; further wherein releasing said applied force reconfigure said protruding portion 201 from said deformed configuration to said protruding portion 201 from said pre-shaped configuration to said deformed configuration.

It is another object of the present invention to provide the clip as defined above, wherein said clip is made of material selected from supper elastic material, mainly Nitinol.

It is another object of the present invention to provide the clip as defined above, wherein said clip is in communication with a support section 305, wherein application of vertical forces upon said U-shaped body of said clip enables portion 201 to penetrate through the patch and through said support section 305.

It is another object of the present invention to provide the clip as defined above, wherein said support section 305 is composed of a soft material selected from a group consisting of polymeric foam, RTV silicon, rubber or any combination thereof.

It is another object of the present invention to provide the clip as defined above, wherein said support section 305 is composed of a rigid material.

It is another object of the present invention to provide the clip as defined above, wherein said support section 305 comprising a groove into which said portion 201 of said CC is adapted to penetrate.

It is another object of the present invention to provide the clip as defined above, additionally comprising a coupling adding mechanism (CM, 306) comprising:
 (a) a socket section 307 adapted to at least partially encapsulate at least a portion of the proximal portion of said PDD;
 (b) a connection platform 308 upon which the distal portion of said PDD is placed, said connection platform 308 comprising at least one support section 305 into which said protruding portion 201 of said CC is inserted.

It is another object of the present invention to provide a clip stapler apparatus (CSA) adapted for reversibly attaching a patch to a patch deployment device (PDD), wherein said CSA comprising:
 a. a holding frame body is adapted to be reversibly coupled to said PDD; said PDD comprising at least one connection clip (CC) for reversibly coupling said patch to said PDD; and,
 b. at least one stapler comprising a top section and a bottom section; each of said staplers is coupled to one edge of said holding frame body such that said CC is located in between said top section and said bottom section;
 each of said staplers is characterized by at least two configurations: a closed configuration, in which said two section are approximated to one another such that said CC penetrates said patch and provides said reversible attachment; and an open configuration in which said two sections are apart from each other.

It is another object of the present invention to provide the clip stapler apparatus (CSA) as defined above, wherein the shape of said holding frame body of said CSA is selected from a group consisting of H-shaped, O-shaped, X shaped, double cross shaped or any combination thereof.

It is another object of the present invention to provide the clip stapler apparatus (CSA) as defined above, additionally comprising means adapted to verify a complete attachment between said patch and said PDD.

It is another object of the present invention to provide the clip stapler apparatus (CSA) as defined above, additionally comprising a groove 407 located in said bottom section 405, adapted to prevent lateral motion of the CC 107 during insertion of said clip into said patch and said top section.

It is another object of the present invention to provide the clip stapler apparatus (CSA) as defined above, wherein said top section 502 and said bottom section 503 are coupled together via a hinge.

It is another object of the present invention to provide the clip stapler apparatus (CSA) as defined above, wherein said CC is characterized by a predetermined U-shaped body; said body is characterized by a main longitudinal axis, and comprising a distal end and a proximal end, said distal end comprising a pre-shaped protruding portion 201 in which said portion 201 is substantially parallel to said main longitudinal axis;
 said proximal end comprising a securing portion 301 coupled to said body; said securing portion 301 is adapted to secure said clip to said PDD;
 said protruding portion 201 comprising at least sharp end adapted to be penetrate said patch;
 said protruding portion 201 is characterized by at least two configurations: (i) said pre-shaped configuration in which said attachment between said patch and said PDD is provided; and, (ii) a deformed configuration in which said protruding portion 201 are deformed from said pre-shaped configuration such that detachment between said patch and said PDD is provided.

It is another object of the present invention to provide the clip stapler apparatus (CSA) as defined above, wherein said CC is made of rigid deformable material selected from stainless steel T304, stainless steel T316.

It is another object of the present invention to provide the clip stapler apparatus (CSA) as defined above, wherein each of said staplers additionally comprises a slide adapted to reciprocally slide towards and away said top section.

It is another object of the present invention to provide the clip stapler apparatus (CSA) as defined above, wherein said top section comprises at least one shaping grooves 605 such that said top section is characterized by a predetermined shape.

It is another object of the present invention to provide the clip stapler apparatus (CSA) as defined above, wherein said slide is adapted to apply pressure on said CC against said top section such that said CC is shaped into said predetermined shape of said top section.

It is another object of the present invention to provide the clip stapler apparatus (CSA) as defined above, wherein said bottom section is adapted to prevent said CC from any unwanted displacement.

It is another object of the present invention to provide a hernia kit adapted for reversibly coupling a patch to a patch deployment device (PDD), comprising:
 a. at least one patch;
 b. at least one PDD; said PDD is characterized by having a distal portion 101, adapted to be inserted into a body and a proximal portion 102, located adjacent to a user; said distal portion and said proximal portion are interconnected along a main longitudinal axis via a tube (103); said tube having a proximal end (TP) connected to said proximal portion, and a distal end (TD); said tube accommodates at least a portion of a central shaft (105);
 said central shaft (105) has a proximal end (CSP) accommodated within said tube (103) and a distal end (CSD) protruding from said TD end of said tube;
 said central shaft (105) is adapted to reciprocally move within said tube (103);
 said movement is parallel to said main longitudinal axis;

a said distal portion comprises:
   (i) at least two frame arms (FA) (104) adapted to be reversibly coupled to said patch;
   (ii) at least two proximal deployment arms (pDA) (108a, 108b) hinge-like connected to said TD and to the proximal end of said two FA;
   (iii) at least two distal deployment arms (dDA) (108c, 108d) hinge-like connected to said CSD and to the distal end of said two FA; each of said pDA and dDA (108a, 108b, 108c, 108d) is characterized by a plurality of configurations, at least one of said configurations is a parallel configuration in which each of said pDA and dDA is substantially parallel to said central shaft (105); and, at least one of said configurations is a substantially perpendicular configuration in which each of said pDA and dDA is substantially perpendicular to said central shaft (105); said FA (104) are characterized by a closed configuration; and, an open configuration at which said patch is deployed; said FA are adapted to reversibly transform from said closed configuration to said open configuration by (i) said reciprocal movement of said central shaft (105) towards and away from said proximal portion; and, (ii) said transformation of each of said DAs from said parallel configuration to said perpendicular configuration, such that said deployment of said patch is at least partially reversible;
   said proximal portion comprising at least one handle (102) located outside said body; said handle is adapted to reversibly transform said FA from said closed configuration to said open configuration;
   c. at least one clip in mechanical communication with said FA, adapted to provide said reversible coupling between said FA and said patch.

It is another object of the present invention to provide the hernia kit as defined above, wherein said clip is characterized by a predetermined U-shaped body; said body is characterized by a main longitudinal axis, and comprising a distal end and a proximal end, said distal end comprising a pre-shaped protruding portion 201 in which said portion 201 is substantially parallel to said main longitudinal axis;
   said proximal end comprising a securing portion 301 coupled to said body; said securing portion 301 is adapted to secure said clip to said PDD;
   said protruding portion 201 comprising at least sharp end adapted to be penetrate said patch; said protruding portion 201 is characterized by at least two configurations: (i) said pre-shaped configuration in which said attachment between said patch and said PDD is provided; and, (ii) a deformed configuration in which said protruding portion 201 are deformed from said pre-shaped configuration such that detachment between said patch and said PDD is provided.

It is another object of the present invention to provide the hernia kit as defined above, wherein application of vertical forces on said protruding portion 201 reconfigure said protruding portion 201 from said pre-shaped configuration to said deformed configuration; further wherein releasing said applied force reconfigure said protruding portion 201 from said deformed configuration to said protruding portion 201 from said pre-shaped configuration to said deformed configuration.

It is another object of the present invention to provide the hernia kit as defined above, wherein said clip is made of material selected from supper elastic material, mainly Nitinol.

It is another object of the present invention to provide the hernia kit as defined above, wherein said clip is in communication with a support section 305, wherein application of vertical forces upon said U-shaped body of said clip enables portion 201 to penetrate through the patch and through said support section 305.

It is another object of the present invention to provide the hernia kit as defined above, wherein said support section 305 is composed of a soft material selected from a group consisting of polymeric foam, RTV silicon, rubber or any combination thereof.

It is another object of the present invention to provide the hernia kit as defined above, wherein said support section 305 is composed of a rigid material.

It is another object of the present invention to provide the hernia kit as defined above, wherein said support section 305 comprising a groove into which said portion 201 of said CC is adapted to penetrate.

It is another object of the present invention to provide the hernia kit as defined above, additionally comprising a coupling adding mechanism (CM, 306) comprising:
   (a) a socket section 307 adapted to at least partially encapsulate at least a portion of the proximal portion of said PDD;
   (b) a connection platform 308 upon which the distal portion of said PDD is placed, said connection platform 308 comprising at least one support section 305 into which said protruding portion 201 of said CC is inserted.

It is another object of the present invention to provide the hernia kit as defined above, wherein said PDD additionally comprising lateral articulating mechanism for providing lateral articulation to said PDD; and vertical articulating mechanism for providing vertical articulation to said PDD.

It is another object of the present invention to provide the hernia kit as defined above, wherein said PDD additionally comprising lateral articulating mechanism for providing lateral articulation to said PDD; and vertical articulating mechanism for providing vertical articulation to said PDD.

It is another object of the present invention to provide a hernia kit for reversibly coupling a patch to a patch deployment device (PDD), comprising:
   a. at least one patch;
   b. at least one PDD; wherein said PDD is characterized by having a distal portion 101, adapted to be inserted into a body and a proximal portion 102, located adjacent to a user; said distal portion and said proximal portion are interconnected along a main longitudinal axis via a tube (103); said tube having a proximal end (TP) connected to said proximal portion, and a distal end (TD); said tube accommodates at least a portion of a central shaft (105); said central shaft (105) has a proximal end (CSP) accommodated within said tube (103) and a distal end (CSD) protruding from said TD end of said tube; said central shaft (105) is adapted to reciprocally move within said tube (103); said movement is parallel to said main longitudinal axis;
   said distal portion comprises:
   (i) at least two frame arms (FA) (104) adapted to be reversibly coupled to said patch;
   (ii) at least two proximal deployment arms (pDA) (108a, 108b) hinge-like connected to said TD and to the proximal end of said two FA;
   (iii) at least two distal deployment arms (dDA) (108c, 108d) hinge-like connected to said CSD and to the distal end of said two FA; each of said pDA and dDA (108a, 108b, 108c, 108d) is characterized by a plurality of configurations, at least one of said configurations is a parallel configuration in which each of said pDA and dDA is substantially parallel to said central shaft (105); and, at least one of said configurations is a substantially perpendicular configuration in which each of said pDA and dDA is substantially perpendicular to said central shaft (105); said FA (104) are characterized by a closed configuration; and, an open configuration at which said patch is deployed; said FA are adapted to reversibly transform from said closed configuration to said open configuration by (i) said reciprocal movement of said central shaft (105) towards and away from said proximal portion; and, (ii) said transformation of each of said DAs from said parallel configuration to said perpendicular configuration, such that said deployment of said patch is at least partially reversible;

said proximal portion comprising at least one handle (102) located outside said body; said handle is adapted to reversibly transform said FA from said closed configuration to said open configuration;

c. at least one clip in mechanical communication with said FA, adapted to provide said reversible coupling between said FA and said patch;

d. at least one clip stapler apparatus (CSA) comprising:
  i. a holding frame body is adapted to be reversibly coupled to each of said FAs; and,
  ii. at least one stapler comprising a top section and a bottom section; each of said staplers is coupled to one edge of said holding frame body such that said CC is located in between said top section and said bottom section; each of said staplers is characterized by at least two configurations: a closed configuration, in which said two section are approximated to one another such that said CC penetrates said patch and provides said reversible attachment; and an open configuration in which said two sections are apart from each other.

It is another object of the present invention to provide the hernia kit as defined above, wherein said PDD additionally comprising lateral articulating mechanism for providing lateral articulation to said PDD; and vertical articulating mechanism for providing vertical articulation to said PDD.

It is another object of the present invention to provide the hernia kit as defined above, wherein the shape of said holding frame body of said CSA is selected from a group consisting of H-shaped, O-shaped, X shaped, double cross shaped or any combination thereof.

It is another object of the present invention to provide the hernia kit as defined above, additionally comprising means adapted to verify a complete attachment between said patch and said PDD.

It is another object of the present invention to provide the hernia kit as defined above, additionally comprising a groove 407 located in said bottom section 405, adapted to prevent lateral motion of the CC 107 during insertion of said clip into said patch and said top section.

It is another object of the present invention to provide the hernia kit as defined above, wherein said top section 502 and said bottom section 503 are coupled together via a hinge.

It is another object of the present invention to provide the hernia kit as defined above, wherein said CC is characterized by a predetermined U-shaped body; said body is characterized by a main longitudinal axis, and comprising a distal end and a proximal end, said distal end comprising a pre-shaped protruding portion 201 in which said portion 201 is substantially parallel to said main longitudinal axis;

said proximal end comprising a securing portion 301 coupled to said body; said securing portion 301 is adapted to secure said clip to said PDD;

said protruding portion 201 comprising at least sharp end adapted to be penetrate said patch; said protruding portion 201 is characterized by at least two configurations: (i) said pre-shaped configuration in which said attachment between said patch and said PDD is provided; and, (ii) a deformed configuration in which said protruding portion 201 are deformed from said pre-shaped configuration such that detachment between said patch and said PDD is provided.

It is another object of the present invention to provide the hernia kit as defined above, wherein said CC is made of rigid deformable material selected from stainless steel T304, stainless steel T316.

It is another object of the present invention to provide the hernia kit as defined above, wherein each of said staplers additionally comprises a slide adapted to reciprocally slide towards and away said top section.

It is another object of the present invention to provide the hernia kit as defined above, wherein said top section comprises at least one shaping grooves 605 such that said top section is characterized by a predetermined shape.

It is another object of the present invention to provide the hernia kit as defined above, wherein said slide is adapted to apply pressure on said CC against said top section such that said CC is shaped into said predetermined shape of said top section.

It is another object of the present invention to provide the hernia kit as defined above, wherein said bottom section is adapted to prevent said CC from any unwanted displacement.

It is another object of the present invention to provide a method for reversibly coupling a patch to a patch deployment device PDD. The method comprises steps selected inter alia from:

a. obtaining least one clip for reversibly attaching a patch to a patch deployment device (PDD), said clip is characterized by a predetermined U-shaped body; said body is characterized by a main longitudinal axis, and comprising a distal end and a proximal end, said distal end comprising a pre-shaped protruding portion 201 in which said portion 201 is substantially parallel to said main longitudinal axis:

said proximal end comprising a securing portion 301 coupled to said body; said securing portion 301 is adapted to secure said clip to said PDD;

said protruding portion 201 comprising at least sharp end adapted to be penetrate said patch;

said protruding portion 201 is characterized by at least two configurations: (i) said pre-shaped configuration in which said attachment between said patch and said PDD is provided; and, (ii) a deformed configuration in which said protruding portion 201 are deformed from said pre-shaped configuration such that detachment between said patch and said PDD is provided.

b. obtaining a coupling adding mechanism (CM) comprising:
  i. a socket section adapted to at least partially encapsulate at least a portion of the proximal portion of said PDD;
  ii. a connection platform 308 upon which the distal portion of said PDD is placed, said connection platform 308 comprising at least one support section 305 into which said protruding portion 201 of said clip is inserted;

c. secure said securing portion 301 of said clip to said PDD;

d. maintaining said clip in said deformed configuration;

e. placing said patch 106 on said support section 305 of said connection platform 308;

f. applying vertical pushing forces on said protruding portion 201 of said clip;

g. inserting said sharp end of said protruding portion 210 through said patch into said support section 305 of said connection platform 308; and, h. removing said PDD from said connection platform 308 thereby reconfiguring said portion 201 from said deformed configuration to said pre-shaped configuration preformed state such that said reversible coupling is provided.

It is another object of the present invention to provide the method as defined above, additionally comprising step of applying vertical forces on said protruding portion 201 reconfigure said protruding portion 201 from said pre-shaped configuration to said deformed configuration.

It is another object of the present invention to provide the method as defined above, additionally comprising step of selecting the material from which said clip is made from supper elastic material, mainly Nitinol.

It is another object of the present invention to provide the method as defined above, additionally comprising step of selecting said support section 305 to be made of a soft material selected from a group consisting of polymeric foam, RTV silicon, rubber or any combination thereof.

It is another object of the present invention to provide the method as defined above, additionally comprising step of selecting said support section 305 to be made of a rigid material.

It is another object of the present invention to provide the method as defined above, additionally comprising step of penetrating said portion 201 of said clip into a groove within said support section 305.

It is another object of the present invention to provide a method for reversibly coupling a patch to a patch deployment device PDD. The method comprises steps selected inter alia from:

a. obtaining least one clip for reversibly attaching a patch to a patch deployment device (PDD), said clip is characterized by a predetermined U-shaped body; said body is characterized by a main longitudinal axis, and comprising a distal end and a proximal end, said distal end comprising a pre-shaped protruding portion 201 in which said portion 201 is substantially parallel to said main longitudinal axis:
said proximal end comprising a securing portion 301 coupled to said body; said securing portion 301 is adapted to secure said clip to said PDD;
said protruding portion 201 comprising at least sharp end adapted to be penetrate said patch;
said protruding portion 201 is characterized by at least two configurations: (i) said pre-shaped configuration in which said attachment between said patch and said PDD is provided; and, (ii) a deformed configuration in which said protruding portion 201 are deformed from said pre-shaped configuration such that detachment between said patch and said PDD is provided.

b. obtaining said PDD; said PDD comprising at least four of said (CC) coupled to the same;

c. obtaining a clip stapler apparatus (CSA) comprising:
 i. a holding frame body reversibly coupled to said PDD;
 ii. at least one stapler comprising a top section and a bottom section; each of said staplers is characterized by at least two configurations: a closed configuration, in which said two section are approximated to one another such that said clip penetrates said patch and provides said reversible attachment; and an open configuration in which said two sections are apart from each other;

d. reversibly coupling said holding frame body to said PDD;

e. secure said securing portion 301 of said clip to said PDD; thereby coupling said clip to said PDD;

f. coupling each of said staplers to said holding frame body such that said clip is located in between said top section and said bottom section;

g. maintaining said clip in said deformed configuration;

h. configuring each of said staplers to be in said open configuration;

i. placing said patch 106 in between said top section and said bottom section;

j. reconfiguring said stapler from said open configuration to said closed configuration by approximating said top section and said bottom section such that vertical forces are applied on said protruding portion 201 of said clip;

k. inserting said sharp end through said patch into said top section of said stapler; and, l. reconfiguring said stapler from said closed configuration to said open configuration, thereby reconfiguring said portion 201 of said clip from said deformed configuration to said pre-shaped configuration such that said reversible coupling is provided.

It is another object of the present invention to provide the method as defined above, additionally comprising step of selecting the shape of said holding frame body of said CSA from a group consisting of H-shaped, O-shaped double cross shaped or any combination thereof.

It is another object of the present invention to provide the method as defined above, additionally comprising step of verifying a complete attachment between said patch and said PDD.

It is another object of the present invention to provide the method as defined above, additionally comprising step of preventing lateral motion of said clip 107 during insertion of said clip into said patch and said top section.

It is another object of the present invention to provide the method as defined above, additionally comprising step of selecting said clip from rigid deformable material selected from stainless steel T304, stainless steel T316 or any combination thereof.

It is another object of the present invention to provide a method for detaching a patch coupled to a tissue from a patch deployment device PDD. The method comprises steps selected inter alia from:

a. obtaining least one crescent shaped connection clip (CC) comprising:
 ii. an elastic crescent shaped body 222 coupled to said PDD;
 iii. at least one protruding portion 201 coupled to said body, adapted to protrude out of said PDD; said protruding portion 201 comprising at least sharp end adapted to penetrate said patch; said protruding portion 201 is characterized by at least two configurations: (i) an attached configuration in which said protruding portion 201 penetrates said patch and positioned substantially parallel to said; and (ii) a detached configuration in which said protruding portion 201 emerges out of said patch and positioned substantially perpendicular to said patch detachment between said PDD and said patch is provided;

b. reconfigured said portion 201 from said attached configuration to said detached configuration thereby detaching said PDD from said patch.

It is another object of the present invention to provide the method as defined above, wherein said step of reconfiguring said attached configuration of said portion 201 to said detached configuration comprising step of applying vertical pulling force on said CC such that said protruding portion 201 is reconfigured.

It is another object of the present invention to provide the method as defined above, wherein said step of reconfiguring said attached configuration of said portion 201 to said detached configuration comprising step of applying vertical pulling force on at least a portion of said PDD such that said protruding portion 201 is reconfigured.

It is another object of the present invention to provide the method as defined above, wherein said step of reconfiguring said attached configuration of said portion 201 to said detached configuration comprising step of applying proximal pulling forces on said CC such that said CC are extracted.

It is another object of the present invention to provide a stapler adapted for reversibly attach a patch to a patch deployment device (PDD), said stapler comprising:

a. a top section, and,
b. a bottom section coupled to said PDD; said PDD comprising at least one connection clip (CC) for reversibly coupling said patch to said PDD;
c. said top section and said bottom section are configured such that said CC is located in between said top section and said bottom section;

each of said staplers is characterized by at least two configurations: a closed configuration, in which said two section are approximated to one another such that said CC penetrates said patch and provides said reversible attachment; and an open configuration in which said two sections are apart from each other.

It is another object of the present invention to provide the stapler as defined above, additionally comprising means adapted to verify a complete attachment between said patch and said PDD.

It is another object of the present invention to provide the stapler as defined above, additionally comprising a groove 407 located in said bottom section 405, adapted to prevent lateral motion of the CC 107 during insertion of said clip into said patch and said top section.

It is another object of the present invention to provide the stapler as defined above, wherein said top section 502 and said bottom section 503 are coupled together via a hinge.

It is another object of the present invention to provide the stapler as defined above, wherein said CC is characterized by a predetermined U-shaped body; said body is characterized by a main longitudinal axis, and comprising a distal end and a proximal end, said distal end comprising a pre-shaped protruding portion 201 in which said portion 201 is substantially parallel to said main longitudinal axis;

said proximal end comprising a securing portion 301 coupled to said body; said securing portion 301 is adapted to secure said clip to said PDD;

said protruding portion 201 comprising at least sharp end adapted to be penetrate said patch;

said protruding portion 201 is characterized by at least two configurations: (i) said pre-shaped configuration in which said attachment between said patch and said PDD is provided; and, (ii) a deformed configuration in which said protruding portion 201 are deformed from said pre-shaped configuration such that detachment between said patch and said PDD is provided.

It is another object of the present invention to provide the stapler as defined above, wherein said CC is made of rigid deformable material selected from stainless steel T304, stainless steel T316.

It is another object of the present invention to provide the stapler as defined above, wherein each of said staplers additionally comprises a slide adapted to reciprocally slide towards and away said top section.

It is another object of the present invention to provide the stapler as defined above, wherein said top section comprises at least one shaping grooves 605 such that said top section is characterized by a predetermined shape.

It is still an object of the present invention to provide the stapler as defined above, wherein said slide is adapted to apply pressure on said CC against said top section such that said CC is shaped into said predetermined shape of said top section.

It is lastly an object of the present invention to provide the stapler as defined above, wherein said bottom section is adapted to prevent said CC from any unwanted displacement.

BRIEF DESCRIPTION OF THE DRAWINGS

The invention is herein described, by way of example only, with reference to the accompanying drawings, wherein.

DETAIL DESCRIPTION OF THE SPECIFIC EMBODIMENTS

Figure 1A:
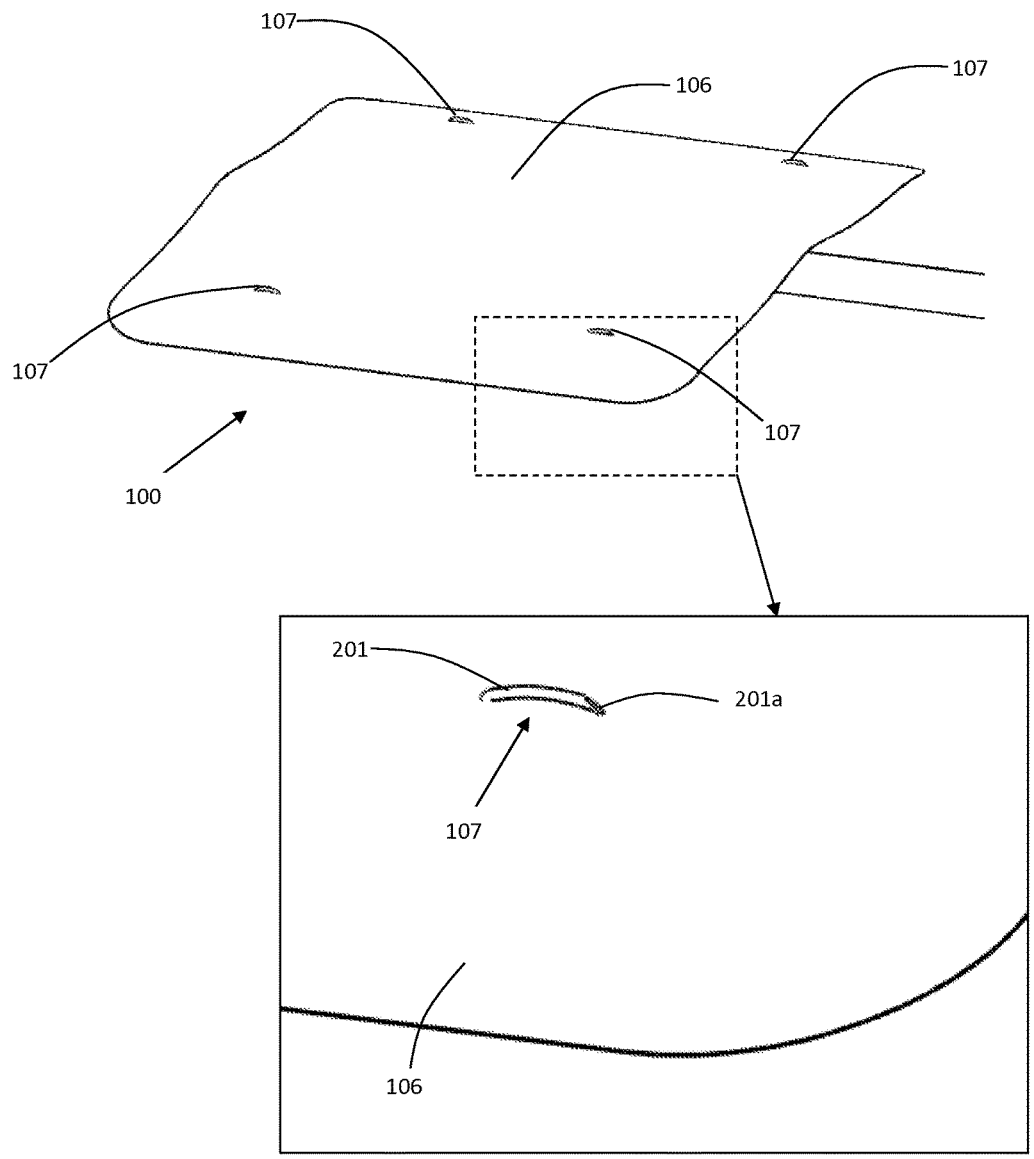
FIGS. 1A-1G illustrate an embodiment of the connection clips (CC) as provided by the present invention.

The following description is provided, alongside all chapters of the present invention, so as to enable any person skilled in the art to make use of the invention and sets forth the best modes contemplated by the inventor of carrying out this invention. Various modifications, however, is adapted to remain apparent to those skilled in the art, since the generic principles of the present invention have been defined specifically to provides means and method for creating a reversible connection between a patch and a patch deployment device.

The present invention provides means in order to provide reversible connection (i.e., attachment and detachment) between a prosthetic patch and a patch deployment device (PDD) wherein said connection can be performed during a surgery at a standard surgery room by the medical staff. Furthermore, the present invention provides means so as to enable the patch to be disconnected from the PDD once it is secured to the tissue.

Furthermore, the present invention provides means enabling a reversible attachment between the patch and the PDD.

The present invention also provides a method for providing said reversible connection between a patch and the patch deployment device (PDD) during a surgery utilizing said means.

It should be emphasized that some of the major advantages of the present invention, with respect to the prior art, is to provide a fast and intuitive method for creating a reliable connection between a patch and a PDD in the surgery room.

The term "Hernia" refers hereinafter for umbilical hernia, hiatal hernia, ventral hernia, postoperative hernia, epigastric hernia, spiegelian hernia, inguinal hernia and femoral hernia, generally any abdominal wall related hernia.

The term "hinge" or "hinge-like connection" refers hereinafter as to a type of bearing that connects two solid objects, typically allowing only a limited angle of rotation between them. Two objects connected by an ideal hinge rotate relative to each other about a fixed axis of rotation (the geometrical axis of the hinge). Hinges may be made of flexible material or of moving components.

The term "hinge like connection" can refer to a standard hinge or to a living hinge (i.e., a thin flexible hinge (flexure bearing) made from plastic that joins two rigid parts together while allowing them to bend along the line of the hinge).

The term 'controlled deployment' refers hereinafter to a patch deployment which is continuous; i.e., the deployment is not binary but analogous—there are several deployment levels. This is in contrast so conventional deployment system is now days (see for example U.S. Pat. No. 5,370,650), in which the deployment of the patch relies upon the elasticity of a loop member surrounding the patch such that the patch can be either fully folded or fully unfolded. No intermediate are enabled. In the present invention there can be several deployment stages.

The term 'bidirectional' or 'fully reversible deployment' refers hereinafter to the deployment of the patch, which according to the present invention, is fully reversible. In other words, the patch deployment is bidirectional, i.e., the patch can be fully folded (i.e., deployed within the body) and then, if the surgeon desires, the patch can be fully unfolded simply by the reconfiguration of the flexible arms from the initial stage to the final stage and vice versa.

The term "minimally invasive surgery" refers hereinafter to procedures that avoid open invasive surgery in favor of closed or local surgery with fewer traumas. Furthermore, the term refers to a procedure that is carried out by entering the body through the skin or through a body cavity or anatomical opening, but with the smallest damage possible.

The term "articulation" refers hereinafter to a joint or juncture between two segments of the device. The articulating means of the present invention provides the ability to better adjust the device to the curvature of the treated tissue.

The term "orientation" refers hereinafter to the rotation of the mesh within the abdominal cavity so as to fit to the hernia. Usually the mesh is not symmetric in shape (i.e., rectangular or i.e., ellipse)—therefore it has different directions. By rotating the mesh within the abdominal cavity—one can decide which direction is turned where.

The term "adjusting" refers hereinafter to rolling, folding and winding of the patch, thus preparing and enabling the insertion of said patch into the abdominal cavity.

The term "downward detachment" refers hereinafter to the detachment between the patch and the patch deployment device (PDD) obtained by pulling the PDD in the downward direction—i.e. away from the treated tissue—(as illustrated in FIGS. 1A-1G). In this embodiment each pair of CCs are facing each other.

The term "detachment mechanism A" refers herein after as a first mechanism adapted to provide the detachment between the patch and the PDD by deformation of the outer frames 104 of the PDD 100. The detachment mechanism A is described in FIGS. 1C-1D.

The term "detachment mechanism B" refers herein after as a second mechanism adapted to provide the detachment between the patch and the PDD by deformation of the connection clips 107. The detachment mechanism B is described in FIGS. 1E-1G.

Figure 1B:
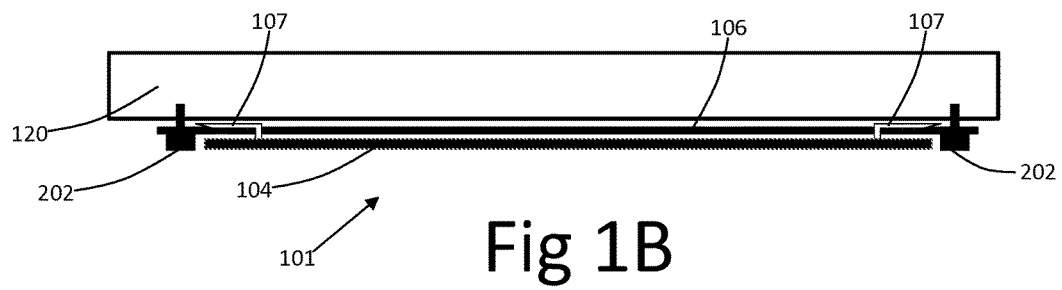
Figure 1C:
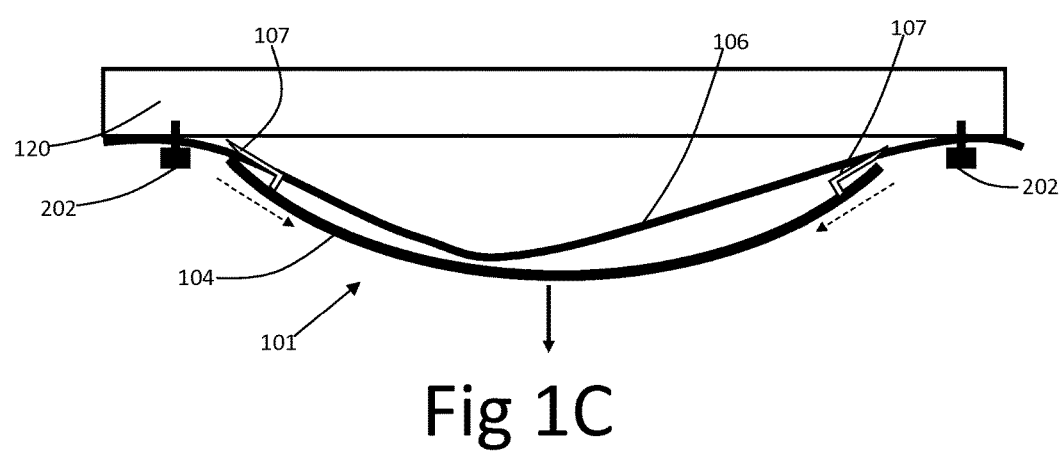
Figure 1D:
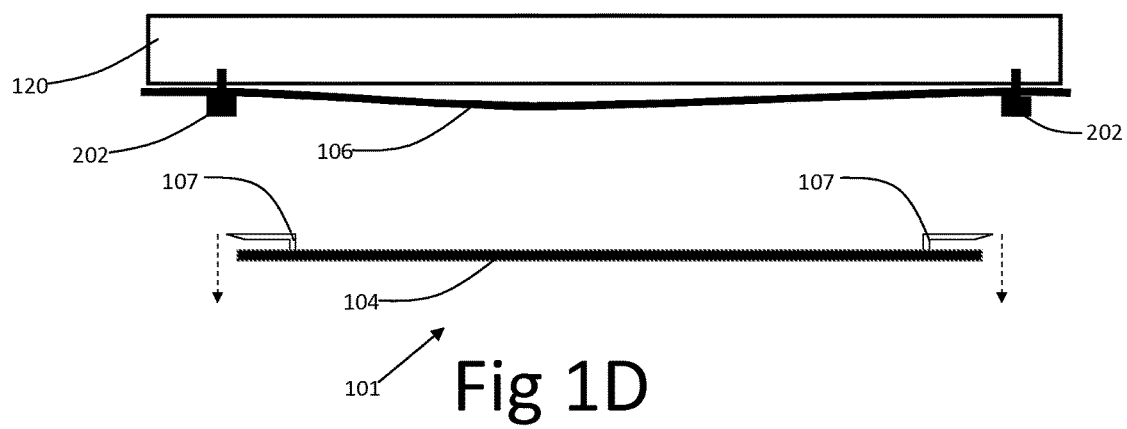
Figure 1E:
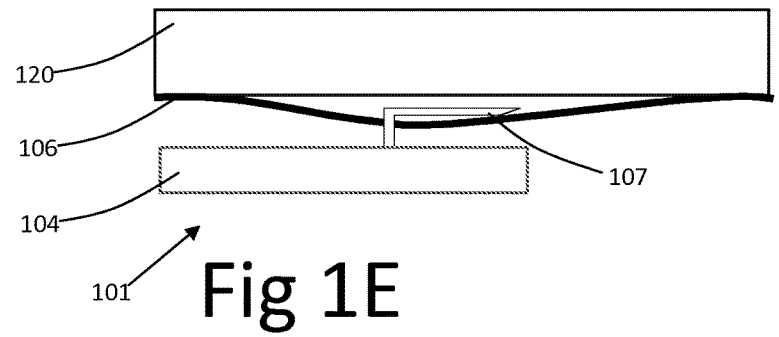
Figure 1F:
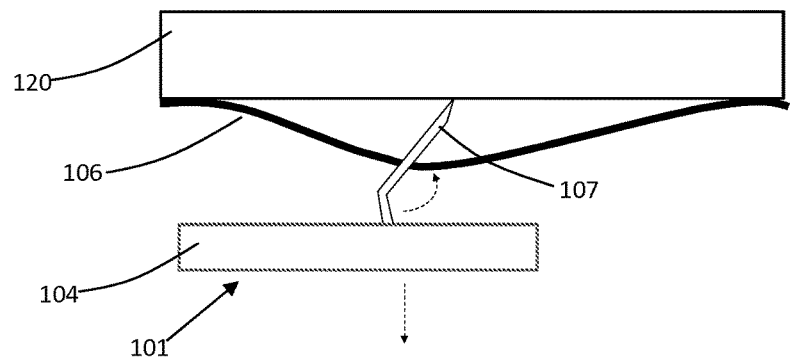
Figure 1G:
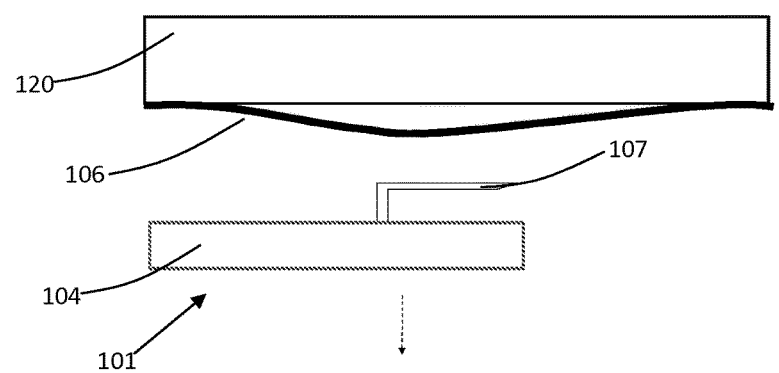
Figure 1H:
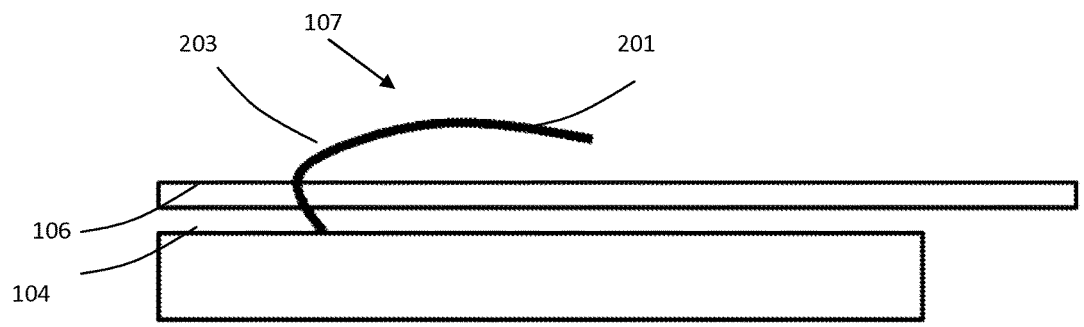
FIGS. 1H-1J illustrate an embodiment of said CC 107 which prevents early detachment.
Figure 1I:
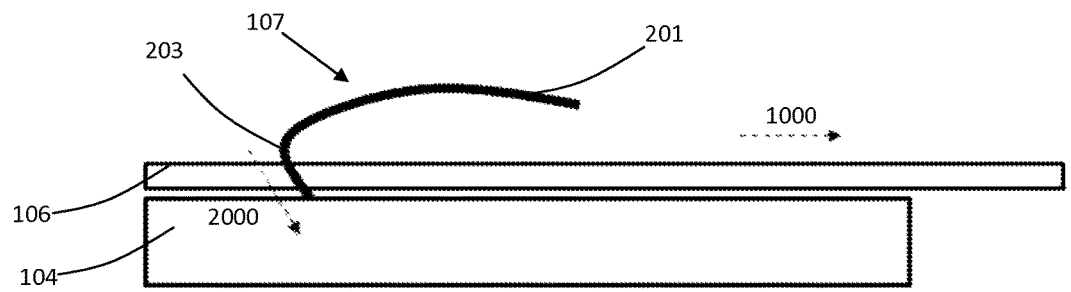
Figure 1J:
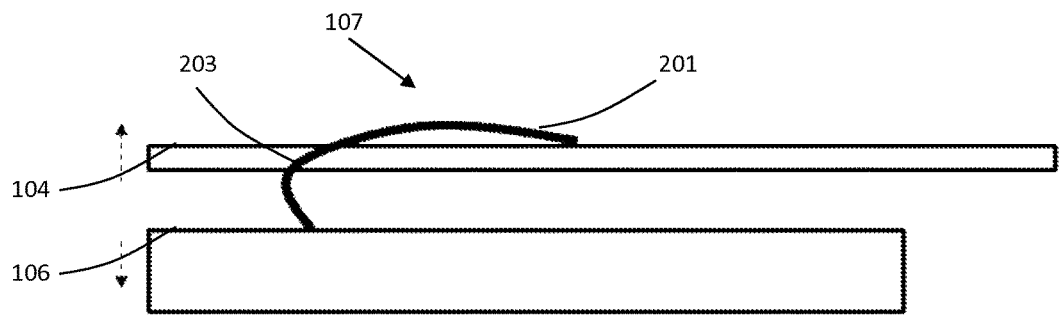
Figure 1K:
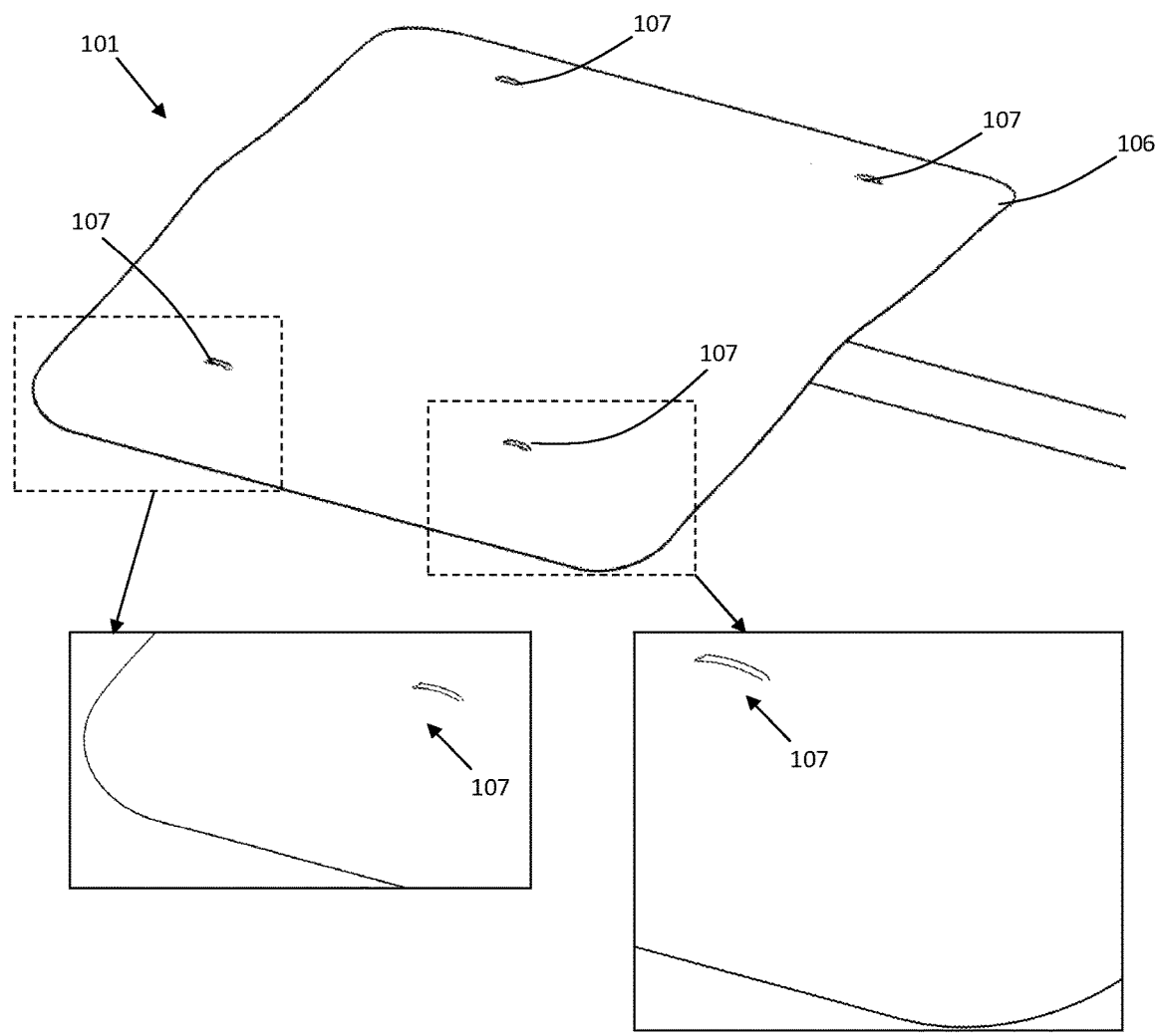
FIGS. 1K-1M illustrate a method for performing the detachment between the distal portion 101 of the PDD 100 and the patch 106 according to one embodiment of the present invention.
Figure 1L:
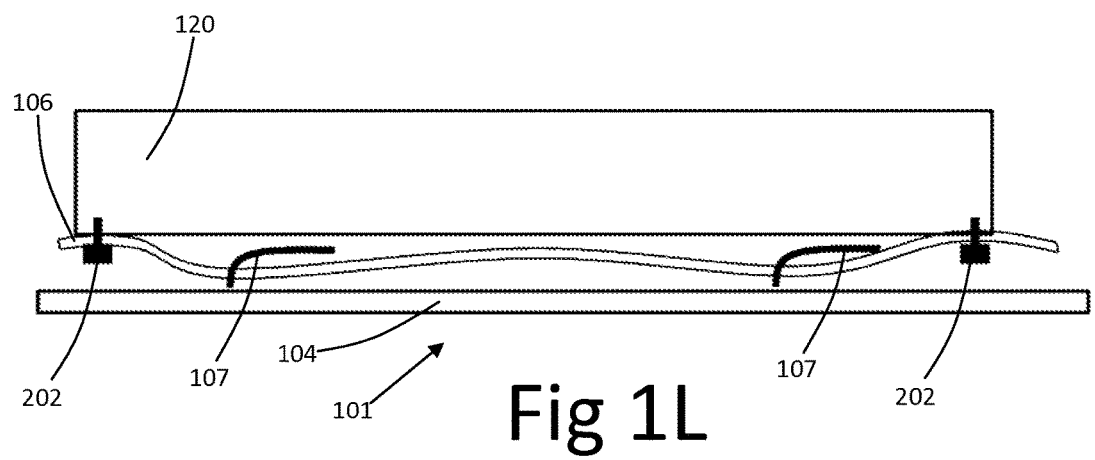
Figure 1M:
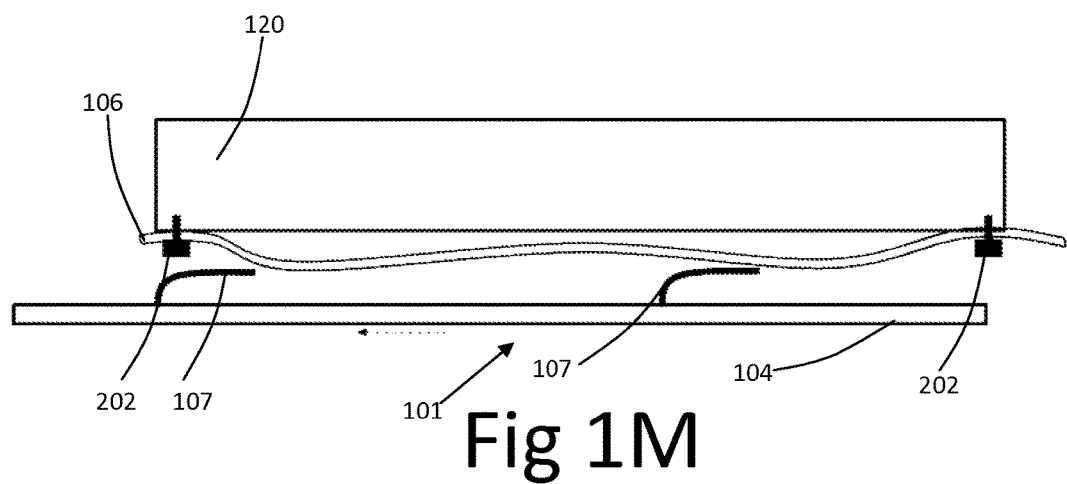

The term "backward detachment" refers hereinafter to the detachment between the patch and the patch deployment device (PDD) obtained by pulling the PDD in the backward/proximally direction—i.e. parallel to the treated tissue, and oppesite to the direction in which the connection clips are facing to (as illustrated in FIGS. 1K-1M). In this embodiment the CCs are aligned and face the same direction (namely forwards).

Before explaining the figures, it should be understood that the invention is not limited in its application to the details of construction and the arrangement of the components set forth in the following description or illustrated in the drawings. The invention can be carried out in various ways.

The reversible connection, as provided by the present invention, is performed using at least two and preferably four connection clips (CC), located at the PDD body. The reversible connection can be made either during the device's assembly (i.e. at the factory). In such a case, the device is supplied with an attached patch.

Alternatively, said reversible connection is performed by the medical staff in the surgery room during the surgery. the medical stuff can be aided by coupling adding mechanism (CM) in order to provide proper attachment. Once the patch is connected to the patient's tissue, said reversible connection is canceled and the PDD is disconnected from the patch.

The present invention discloses several embodiments of said CC and said CM in addition to several patch connection and disconnection mechanisms.

It is acknowledged that the coupling adding mechanism (CM) can be selected from a group consisting of staplers or any mechanism that is able to attach and detach the CC to and from the PDD.

Reference is now made to FIGS. 1A-1G which describe an embodiment of said connection clips (CC) 107 and the method of performing the detachment between the PDD 100 and the patch 106, once the patch is attached to the tissue 120.

According to this embodiment said detachment is obtained by pulling the distal portion 101 of the PDD (i.e., the portion which is adapted to be inserted into the patient's body) downward with regards to the patient's tissue 120 once the attachment between the patch 106 and the tissue 120 is obtained (said detachment will be referred hereinafter as the 'downward detachment').

FIG. 1A illustrates an example of a PDD 100, patch 106 and the protruding portion 201 of each of the CCs 107 which protrudes out from the patch 106. As can be seen from the figure, the CC 107 is crescent shaped.

In general each PDD 100 comprises at least two portions: a distal portion 101 and a proximal portion 102. The proximal portion is adapted to remain outside the body, adjacently to the user and the distal portion 101 is adapted to be inserted into the body. The distal portion comprises at least one outer frame 104 to which the patch is attached.

According to one embodiment each PDD is provided with at least one CC 107. Each of the CCs 107 comprises a body 222 coupled to the outer frames 104 of the PDD 100 and at least one protruding portion 201 protruding out from the outer frames 104 of the PDD 100.

The protruding portion 201 is characterized by a sharp end adapted to penetrate said patch.

The protruding portion 201 is characterized by at least two configurations:
  (i) An attached configuration in which said protruding portion 201 penetrates the patch 106 and eventually positioned substantially parallel to said patch. In this configuration an attachment between the PDD and the patch is provided;
  (ii) A detached configuration in which the protruding portion 201 emerges out of the patch. In this configuration a detachment between the PDD and the patch is provided.

As will be described hereinafter, application of forces, vertical or parallel to said patch, on said CC (and mainly on the protruding portion 201) reconfigure said protruding portion 201 from said attached configuration to said detached configuration.

As described, the protruding portion 201 of each CC 107 is inserted through the patch 106 such that said portion 201 is eventually positioned above the patch 106 (see FIG. 1A).

In order to prevent entanglement of each CC 107 with patch 106 during patch rolling and insertion, portion 201 of each CC 107 is bended such that its end 201a is pointing downward toward the outer frames 104 of the PDD 100.

Reference is now made to FIGS. 1B-1G illustrating the detachment between the patch and the PDD once the patch is attached to the tissue.

Once patch 106 is properly connected to the distal portion 101 of the PDD 100 (the distal portion of the PDD is the portion which is to be inserted into the patient's body containing the patch to be deployed therein) utilizing the CCs 107, it can be rolled and inserted into the patient's abdominal cavity via a trocar 114. In the abdominal cavity the patch 106 is deployed and attached to the patient's tissue 120 using a patch-tissue connection means 202 (PTC) (FIG. 1B).

Once said attached is obtained (i.e., attachment between the patch and the tissue), the distal portion 101 of the PDD 100 is detached from the patch 106 in order to enable its extraction outside from the patient's abdominal cavity.

As a result, the patch 106 is disconnected from the distal portion 101 according to any of the following mechanisms:

The first mechanism (refers hereinafter as detachment mechanism A) provides said detachment by bending or deforming the outer frames 104 of the PDD 100. The deformation is provided by applying pulling force. Such bending causes the CCs 107a and 107b to move toward each other, sliding out of the patch; thereby, the patch 106 is disconnected from the distal portion 101 of the PDD 100 (see FIGS. 1C-1D).

The second mechanism (refers hereinafter as detachment mechanism B) provides disconnection by bending the CCs 107 as a result of said pulling force, such that they deform in such a manner that portion 201 become substantially perpendicular to the tissue 120 and slide out of the patch; thereby, the patch 106 is disconnected from the distal portion 101 of the PDD 100 (see FIGS. 1E-1G).

The contribution of each mechanism to said detachment depends on the relative flexibility of the PDD (and in particularly the outer frames 104) and the CCs 107 in addition to their mechanical dimensions.

During the process of patch 106 insertion into the abdominal cavity, the patch 106 may be stretched either toward the proximal portion or toward the distal portion of the PDD 100. This is the result of friction forces between the patch 106 and the trocar 114.

As a result of such forces, the patch 106 may slide out from the CCs 107 prior to the deployment of said patch. Such patch detachment will be referred hereinafter as early detachment of the patch.

FIG. 1H-1J describe an embodiment of said CC 107 which prevents said early detachment. According to this embodiment, said CCs 107 comprises of a slide prevention section (SPS) 203. Said SPS is adapted to prevent said early detachment (see FIG. 1H). The SPS is coupled to the protruding section 201 and is constructed as a slope pointing downward toward the outer frames 104 of the PDD 100.

During patch insertion, the patch 106 is rolled around the distal portion 101 of the PDD and pressed toward the outer frames 104 of the same.

Once the patch is inserted into the trocar, said sliding/friction forces (illustrated as arrow 1000 in FIG. 1I) are applied. As a result, patch 106 is caught in section 203 (illustrated as arrow 2000 in FIG. 1I) instead of sliding out of CC 107 through portion 201 (see FIG. 1I). In such a manner said early detachment is prevented.

It should be pointed out that SPS 203 does not interfere with the desired detachment between patch 106 and the PDD once the patch is attached to the tissue. Once vertical pulling forces are applied during a desired detachment, the patch 106 slides above SPS 203. Once patch 106 slides above SPS 203 it can be extracted from portion 201 according to either one of said detachment mechanism A or detachment mechanism B (FIG. 1J).

Reference is now made to FIGS. 1K-1M which describe yet another method for performing said detachment between the distal portion 101 of the PDD 100 and the patch 106.

According to this embodiment said detachment is obtained by pulling or pushing the distal portion 101 to a direction opposite to the direction of said CC, preferably, backward (i.e., towards the proximal direction). The forces are applied once the attachment between the patch and the tissue 120 is obtained (such detachment embodiment refers hereinafter as backward detachment).

This embodiment utilizes a similar CCs 107 as described in FIG. 1A-1F; however, in this case both the CCs 107 are facing forward (see FIG. 1K).

This configuration ensures that the patch 106 will remain attached to the distal portion 101 while subjected to backward facing forces which are applied during insertion as a result of the friction between patch 106 and the trocar 104.

Once the patch is secured to the patient's tissue 120 using PTC 202 (see FIG. 1L), the distal portion can be detached from the patch by backward pulling of the PDD 100 (see FIG. 1M).

Figure 1N:
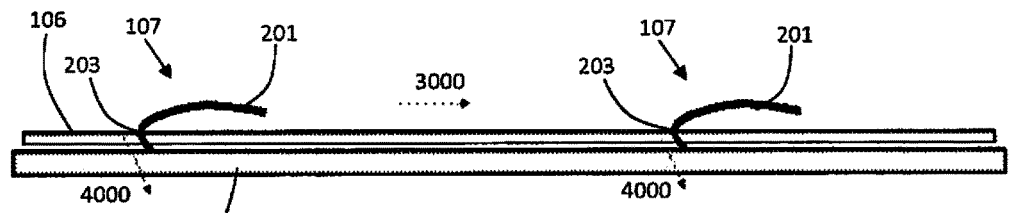
FIGS. 1N-1P illustrate a variation of the backward detachment in which early detachment is prevented.
Figure 1O:
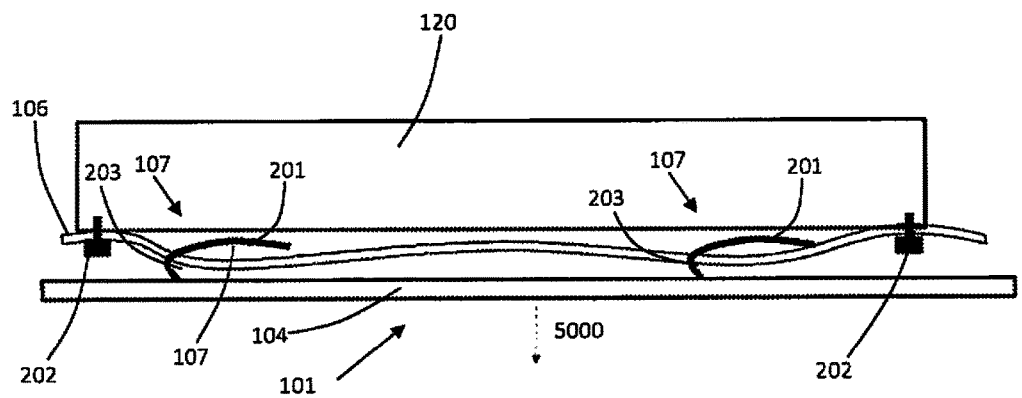
Figure 1P:
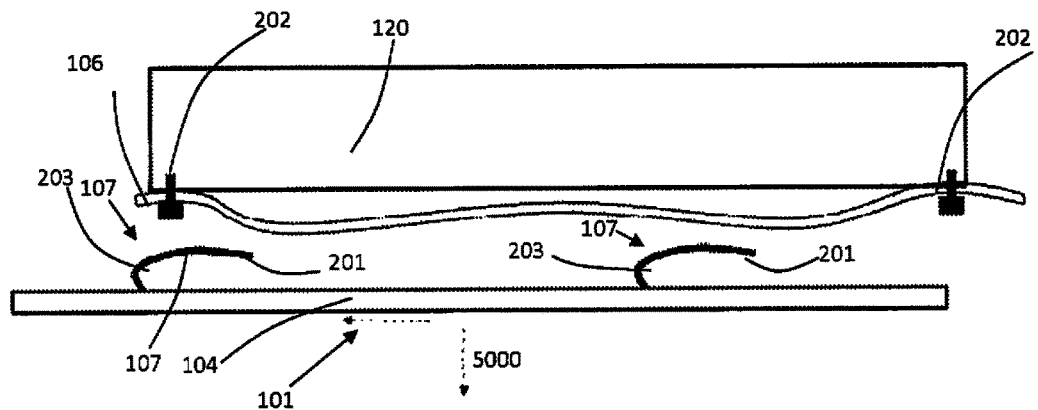

FIGS. 1N-1P describe a variation of said backward detachment in which early detachment is prevented.

If during patch insertion the movement is reversed (i.e. the patch is pulled out instead of inserted inside the abdominal cavity) the patch may be detached from the distal portion (i.e. early detachment).

Prevention of said early detachment can be obtained by configuring the CC 107 to be shaped as described in FIGS. 1N-1O. As can be seen in FIG. 1N, once patch 106 is subjected to said reverse forces (illustrated in FIG. 1N as arrow 3000), it is held by SPS 203 (illustrated in FIG. 1N as arrow 4000), such that early detachment is prevented.

Once patch 106 is secured to the patient's tissue 120 by PTC 202, a detachment can be obtained by backward pulling of the outer frames 104 while applying downward force (illustrated in FIG. 1O as arrow 5000), see FIGS. 1O-1P.

The above disclosure describes an attachment/detachment mechanisms between the patch and the PDD 100. The following disclosure describes an example of a PDD 100.

Figure 2A:
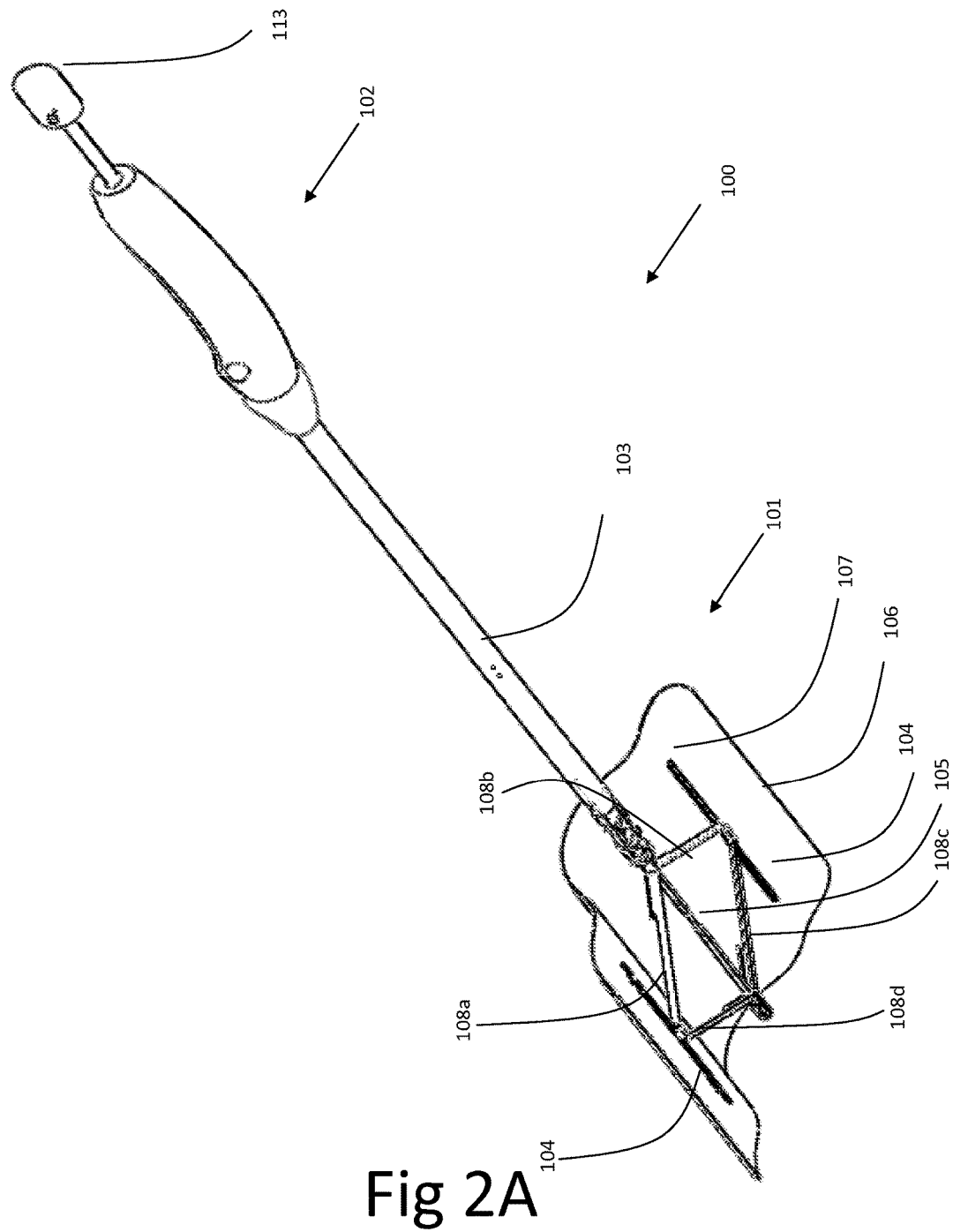
FIG. 2A illustrates an example of the PDD according to one embodiment of the present invention.

Reference is now made to FIG. 2A illustrating an embodiment of the present invention. According to that embodiment a patch deployment device (PDD), 100 is provided along with the connection clips located at the PDD's body.

The PDD 100 comprises two main portions: distal portion 101, and a proximal portion 102. The two portions are connected via a tube 103. The distal portion is adapted to be inserted into a body during the surgery via a trocar. The distal portion is also adapted to deploy and place a prosthetic hernia repair patch 106 onto the patient's tissue 120 surface.

The distal portion comprises of at least two frame arms (FA) 104, at least 4 deployment arms (DA) 108 and a central shaft 105 adapted to reciprocally move within tube 103.

The DAs 108 can be divided into two groups: 2 DAs (108a and 108b) which are proximally located and 2 DAs (108d and 108c) which are distally located.

The proximal DAs 108a and 108b are connected to the tube 103's distal end and to the FA 104. The distal DAs 108c and 108d are connected to the central shaft 105 and to the FAs 104. All said connections are hinge connections.

Each of said DAs (108) is characterized by a plurality of configurations. One of said configuration is a parallel configuration in which the DA is substantially parallel to said central shaft (105). Another one of said configuration is an angled configuration in which said DA are located at an angle A with respect to said central shaft (105). Angle A can be at a range of about 0 degrees to about 180 degrees.

Figure 2B:
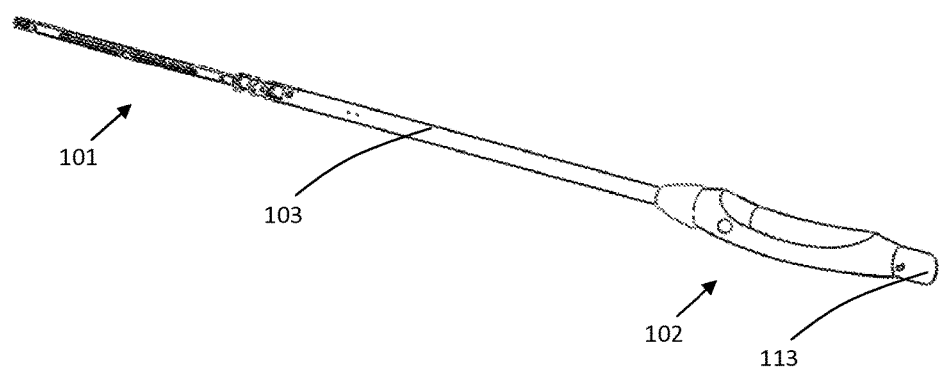
FIGS. 2B-2C illustrate the PDD 100 in its deployhed configuration and in its close configuration. The close configuration is described in FIG. 2B while the deployed configuration is describe in FIG. 2C.
Figure 2C:
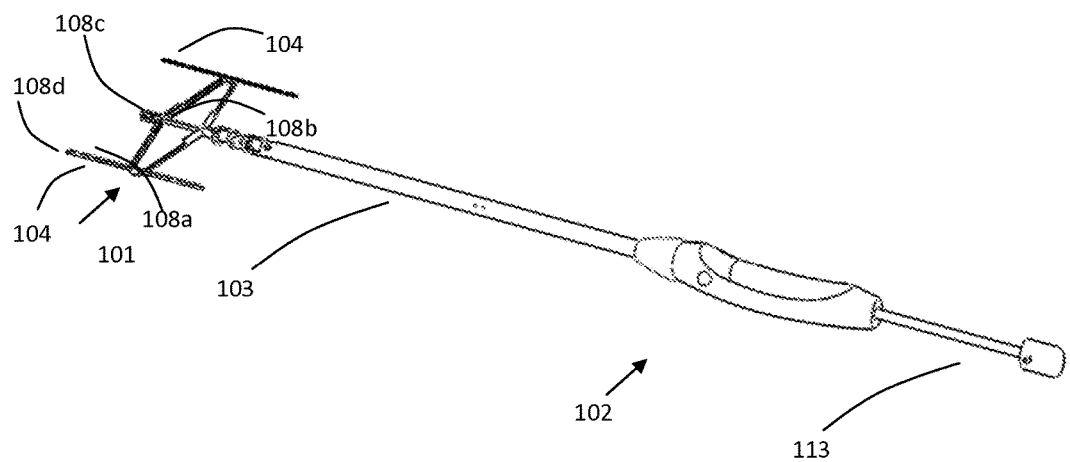

Reference is now made to FIGS. 2B-2C which illustrate the PDD 100 in its deployed configuration and in its close configuration. The close configuration is described in FIG. 2B while the deployed configuration is describe in FIG. 2C.

In the parallel configuration the PDD 100 is in its close configuration and in the perpendicular configuration, the PDD 100 is in its deployed configuration.

The patch/mesh/net 106 is reversibly attached to the FAs 104 by a reversible CC 107 as described above.

According to one embodiment, the distal portion 101 can be rotated laterally (i.e. left and right with regards to tube 103) and vertically (i.e. up and down in relation to the tube 103), such that the patch could be properly aligned and oriented within the abdominal cavity with regards to the hernia. Such rotation is enabled via the articulating means as will be described hereinafter.

The proximal portion 102 comprises (a) a deployment lever 113 which provides the surgeon the ability to control the deployment process; (b) an articulation lever (not shown) which provides the surgeon the ability to control lateral articulation angle of the distal portion; and, (c) a release button (not shown) which provides the surgeon the ability to roll the distal portion to its close configuration prior to its extraction for the patient's body.

As described above, the patch/mesh/net 106 is reversibly attached to the outer frames 104 (and in this example—to the FAs 104) by a connection clips (CC) 107. The CCs can be an integral part of the FAs 104 or a separate part which is combined and secured to the PDD 100 during the product assembly.

Reference is now made to FIGS. 3A-3F which describe another embodiment of the CC 107 and a method for providing said reversible connection between patch 106 and the distal portion 101 of the PDD 100.

According to this embodiment CC 107 is composed of a single elastic wire, preferably superelastic Nitinol (i.e. NiTi alloy).

The wire is preformed (i.e., was thermally) into its final shape.

Figure 3A:
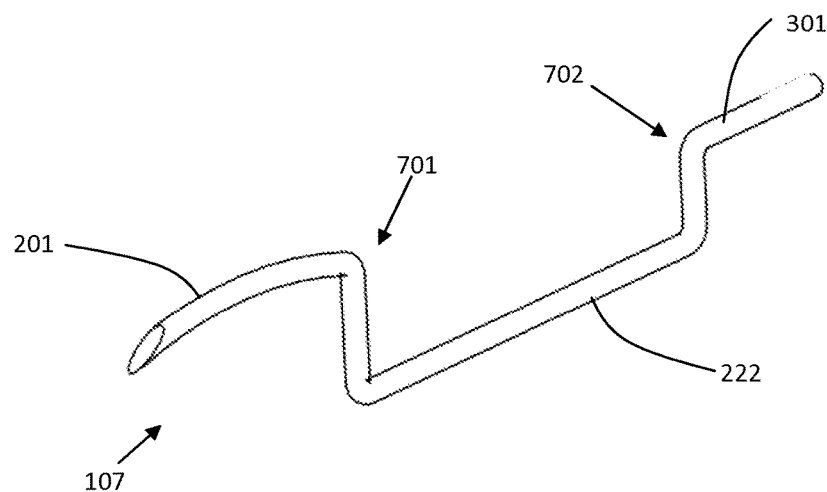
FIGS. 3A-3F illustrate another embodiment of the CC 107.

The final shape is characterized by a predetermined U-shaped body 222. said body 222 is characterized by a main longitudinal axis, and comprising a distal end 701 and a proximal end 702, said distal end 701 comprising a pre-shaped protruding portion 201 in which said portion 201 is substantially parallel to said main longitudinal axis The proximal end 702 comprising a securing portion 301 coupled to the U-shaped body 222; said securing portion 301 is adapted to secure said clip to said PDD (see FIG. 3A).

Said protruding portion 201 comprises at least sharp end adapted to be penetrate the patch. Furthermore, said protruding portion 201 is characterized by at least two configurations: (i) said pre-shaped configuration in which said attachment between said patch and said PDD is provided; and, (ii) a detached configuration in which detachment between said patch and said PDD is provided. It should be emphasized that in the deformed configuration the protruding portion 201 are deformed from said pre-shaped configuration such that detachment between said patch and said PDD is provided. Alternatively, in the deformed configuration, the PDD can be deformed such that the detachment between said patch and said PDD will be provided.

Figure 3B:
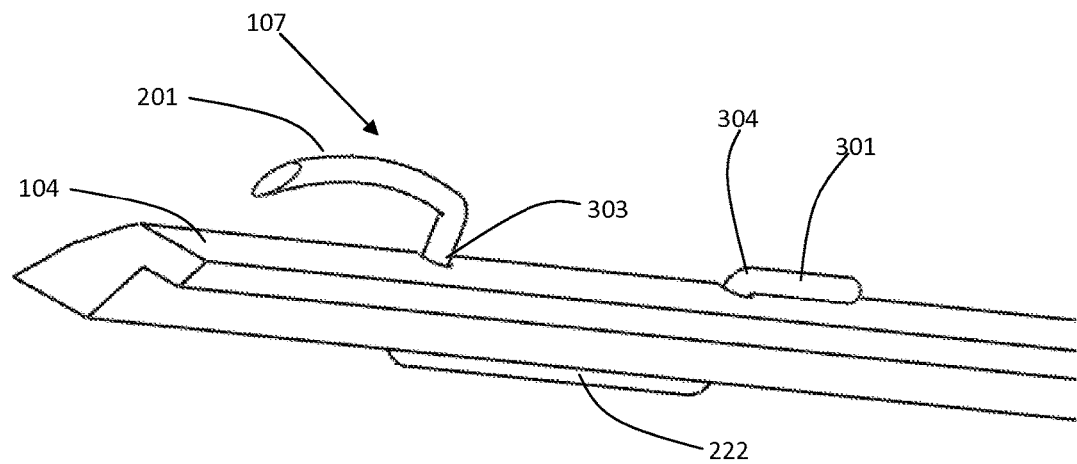

Reference is now made to FIGS. 3A-3F which illustrate said U-shape clip and its use:

According to this embodiment the CC 107 is adapted to be inserted into two holes 303, 304 at the FA 104 (FIG. 3B).

Alternatively, as mentioned above, the CC can be partially inserted into said CM (e.g., stapler) which is provided along with the PDD 100.

FIGS. 3C-3F describes a process in which CC 107 is inserted into the FA 104 and patch 106 in order to provide said reversible attachment.

Figure 3C:
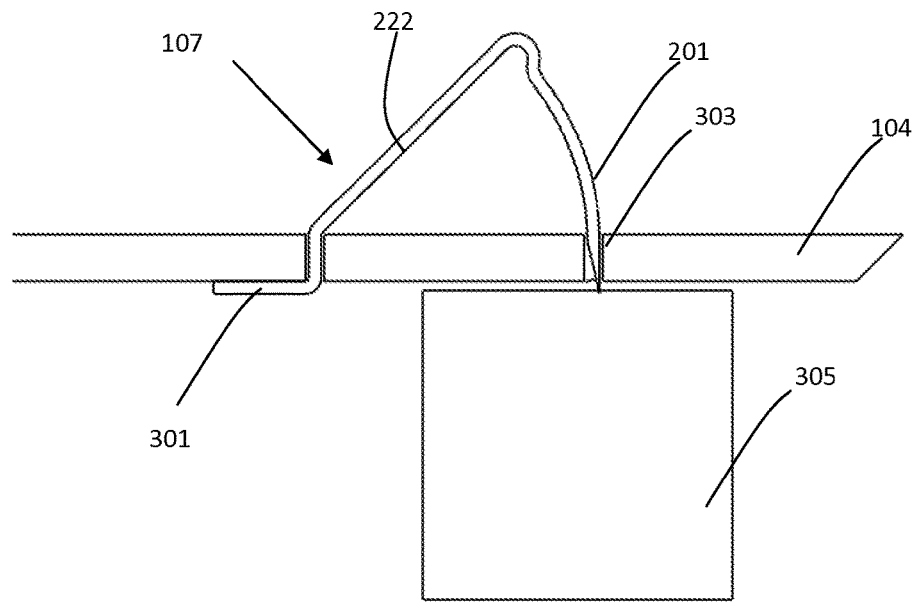
Figure 3D:
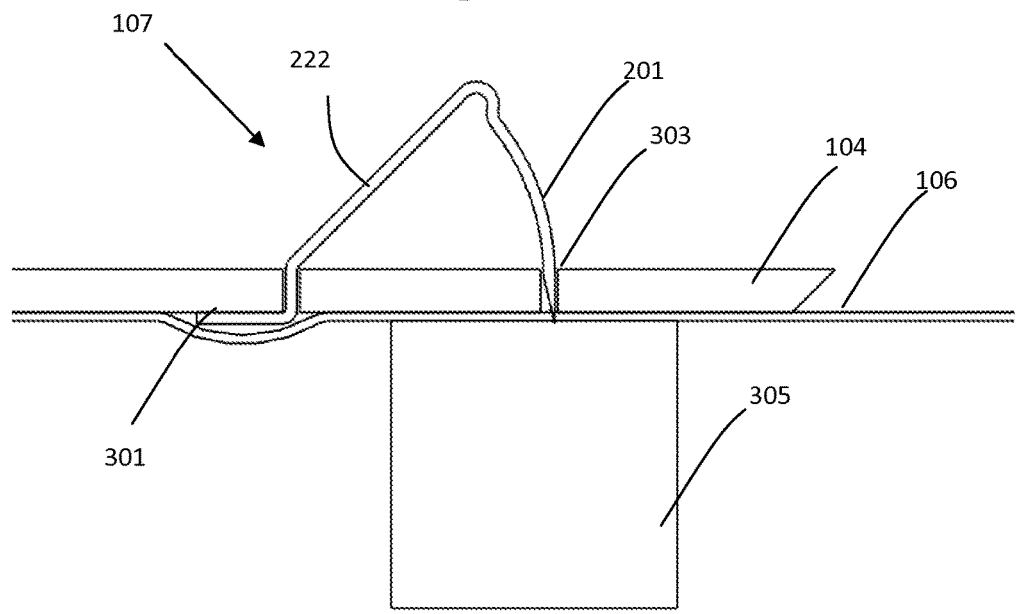

The CC 107 is initially secured to the FA 104 by said securing portion 301, while portion 201 is partially inserted into FA 104 via hole 303 (see FIG. 3C).

Next, patch 106 is placed between FA 104 and a support section 305 (see FIG. 3D), wherein application of vertical forces upon said CC 107 (namely said U-shaped body) towards said patch and said support section 305 enables portion 201 to penetrate through the patch.

Support section 305 is composed of a soft material (e.g. polymeric foam, RTV silicon, rubber), alternatively it can be composed of a rigid material containing a groove into which portion 201 can penetrate.

Figure 3E:
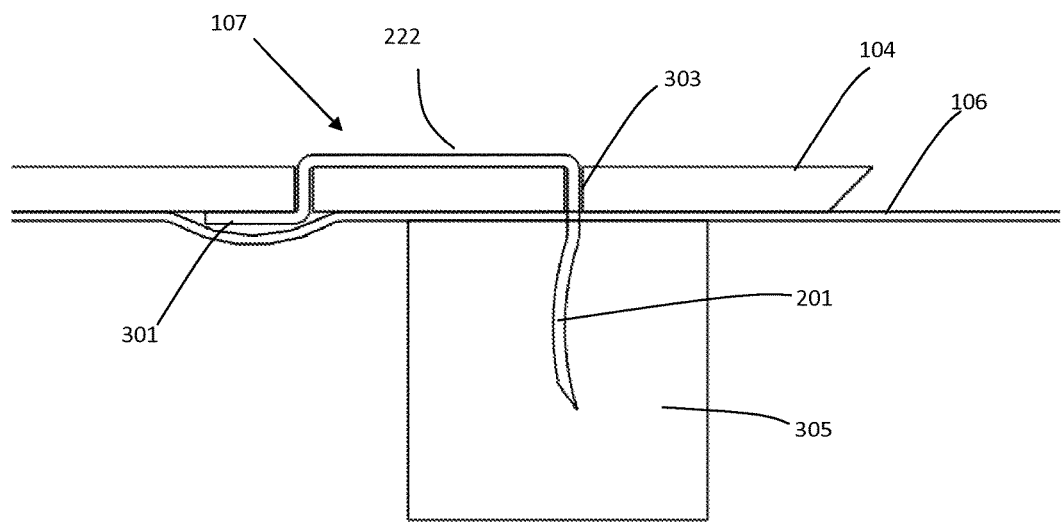

Once patch 106 is properly placed, CC 107 is pressed into said support section 305 through hole 304 and patch 106 (see FIG. 3E).

Figure 3F:
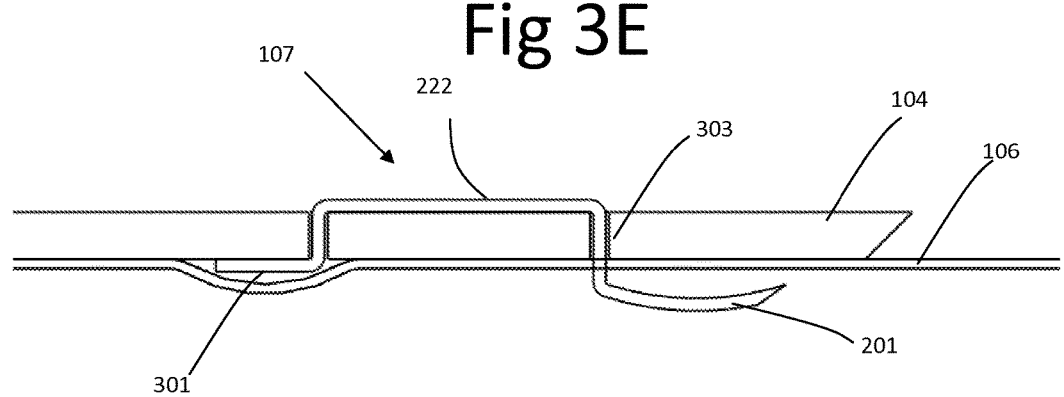

Once the support section 305 is removed, portion 201 springs back into its preformed state, therefore providing said reversible connection between said PDD and the patch (see FIG. 3F).

Portion 201 springs back into its preformed state since it is of supper elastic material (e.g. Nitinol).

Reference is now made to FIGS. 3H-3K which illustrate one embodiment of a coupling adding mechanism (CM) 306 adapted to enable said reversible attachment.

In a preferred embodiment, the CM 306 is also a part of the product packaging.

Figure 3H:
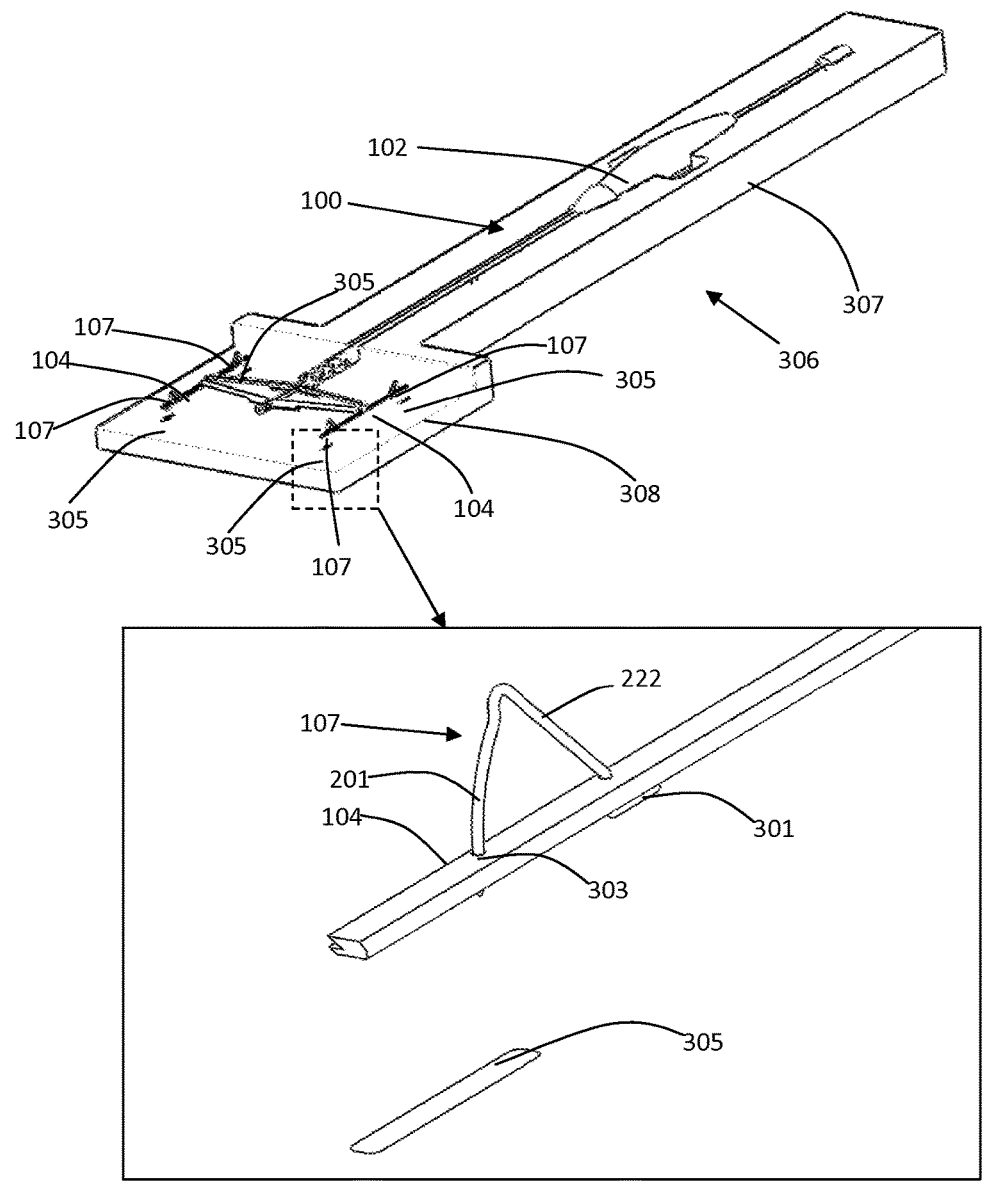
FIGS. 3H-3K illustrate one embodiment of a coupling adding mechanism (CM) 306 which is adapted to enable said reversible attachment.

CM 306, composed of a socket section 307, and a connection platform 308 (see FIG. 3H). Said socket section 307 is designed to fit and at least partially encapsulate at least a portion of the proximal portion 102 while holding the PDD 100 in its upside down orientation (i.e., the protruding section of CC 107 is facing towards the connection platform 308).

Said connection platform 308 comprises at least one support section 305, preferably four support sections 305, each of which is located below each CC 107.

Figure 3I:
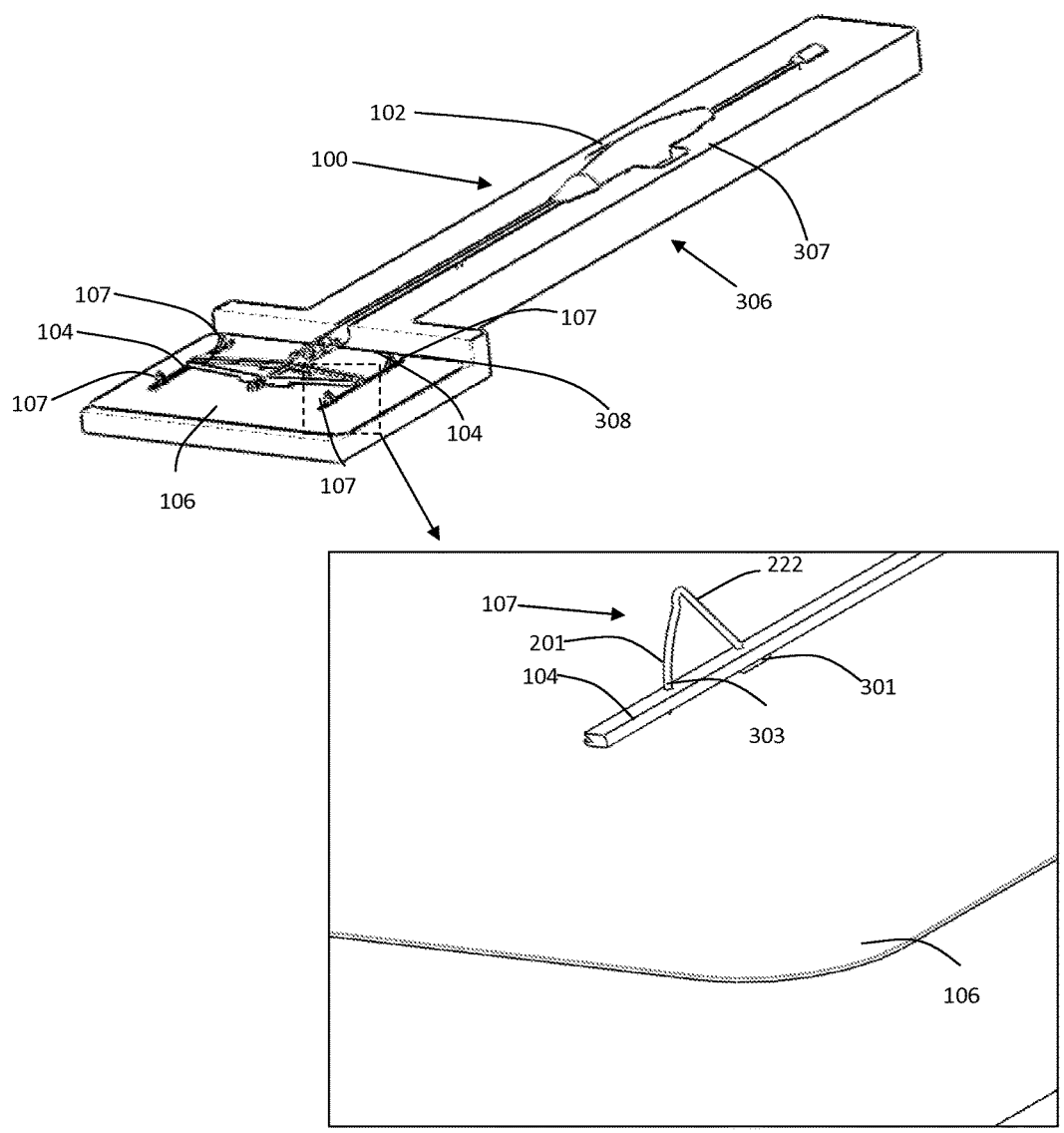
Figure 3J:
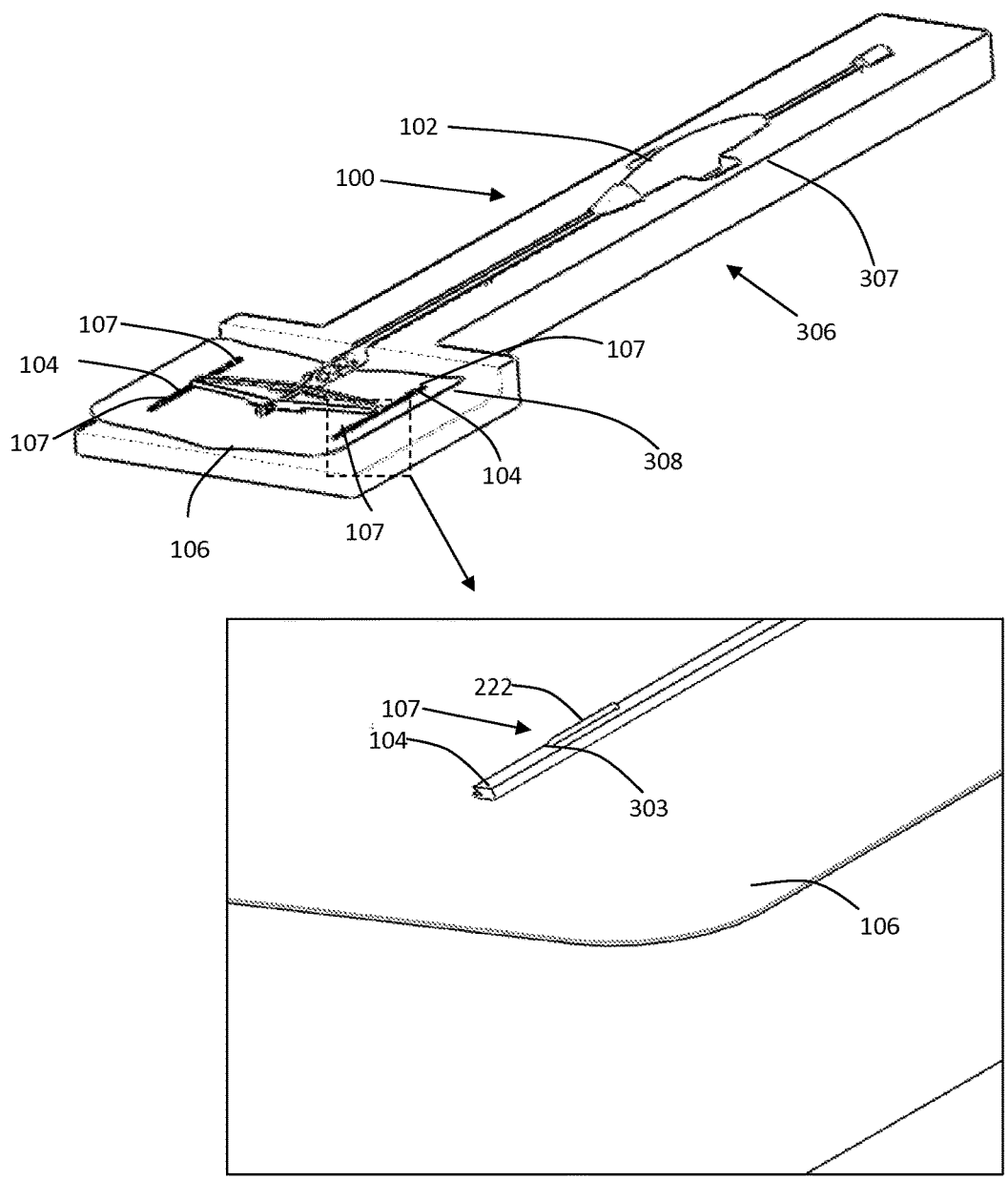
Figure 3K:
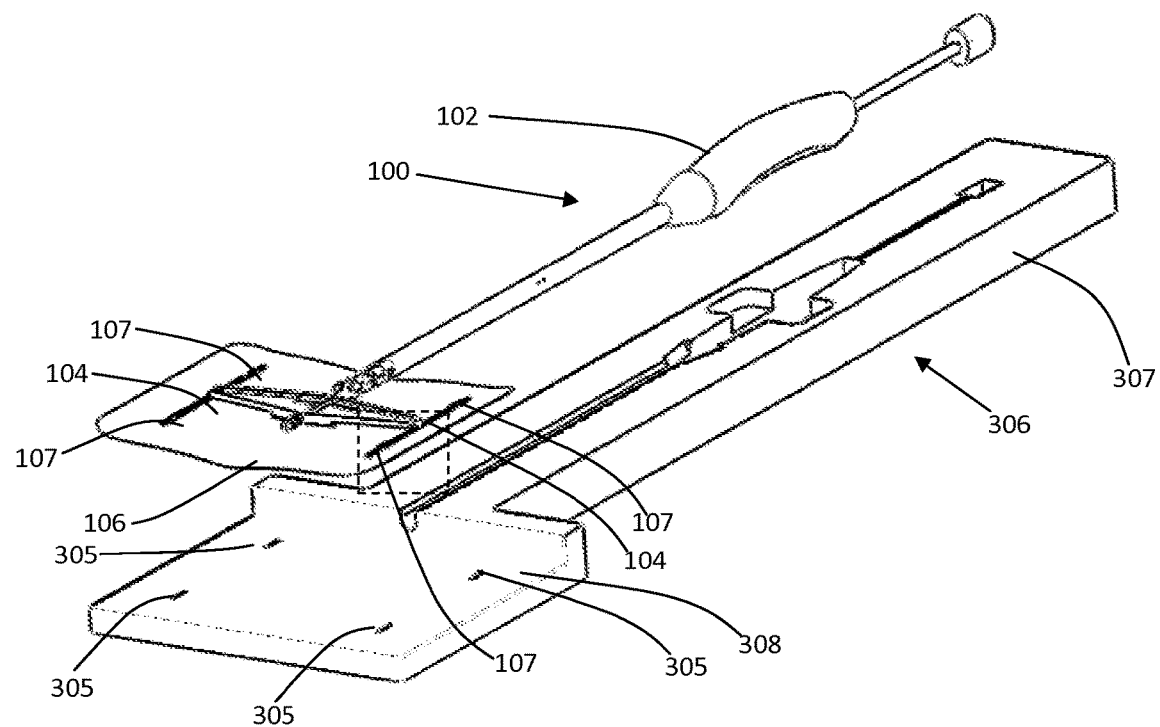

According to a preferred embodiment the PDD 100 is preferably supplied within said CM 306. Reference is now made to FIGS. 3I-3K describing the method in which said CM 306 is utilized for providing said reversible attachment.

First, PDD 100 is at least partially lifted and patch 106 is placed onto said connection platform 308, alternatively patch 106 is inserted below distal portion 101 without lifting PDD 100 (see FIG. 3I).

Next, each one of CC 107 (namely the protruding portion 201) is pushed into the dedicated support section 305 through FA 104 and patch 106 (see FIG. 3J).

Once all of the CCs 107 are inserted into the supporting section 305, the PDD 100 and patch 106 are lifted from the CM 306 (FIG. 3K). Hence, a reversible connection between the patch and the PDD is obtained.

Reference is now made to FIGS. 4A-4I which describe clip stapler apparatus (CSA) 401 adapted to assist in creating said reversible attachment.

Said CSA 401 comprises a holding frame body 402. The holding body 402 comprises at least one stapler 403 coupled to said holding body 402 at each of its four ends (see FIG. 4A). In the figure four staplers are shown; however, at least one is needed.

Said holding body 402, is adapted to hold and support the FA 104 in an open state, while aligning it to its proper position.

Each of the staplers, as will be described hereinafter, is characterized by at least two configurations: a closed configuration, in which said two sections are approximated to one another such that said CC penetrates said patch and provides said reversible attachment; and an open configuration in which said two sections are apart from each other.

Each stapler 403 is adapted to insert one CC 107 through patch 106 and FA 104 in order to obtain said reversible attachment.

Each stapler composed a top section 404 and a bottom section 405.

It should be emphasized that the shape of the holding frame body can be selected from a group consisting of H-shaped, O-shaped X shaped, double cross shape or any combination thereof.

Figure 4A:
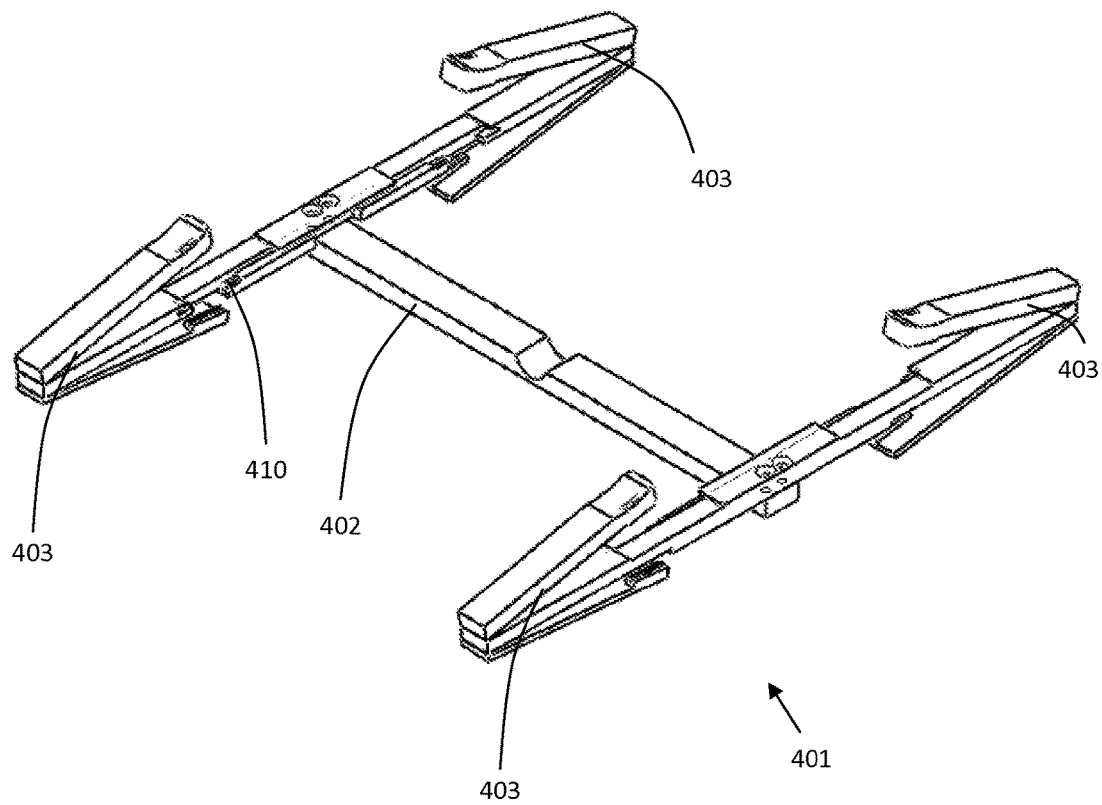
FIGS. 4A-4H illustrate a clip stapler apparatus (CSA) 401 adapted to assist in creating the reversible attachment.
Figure 4B:
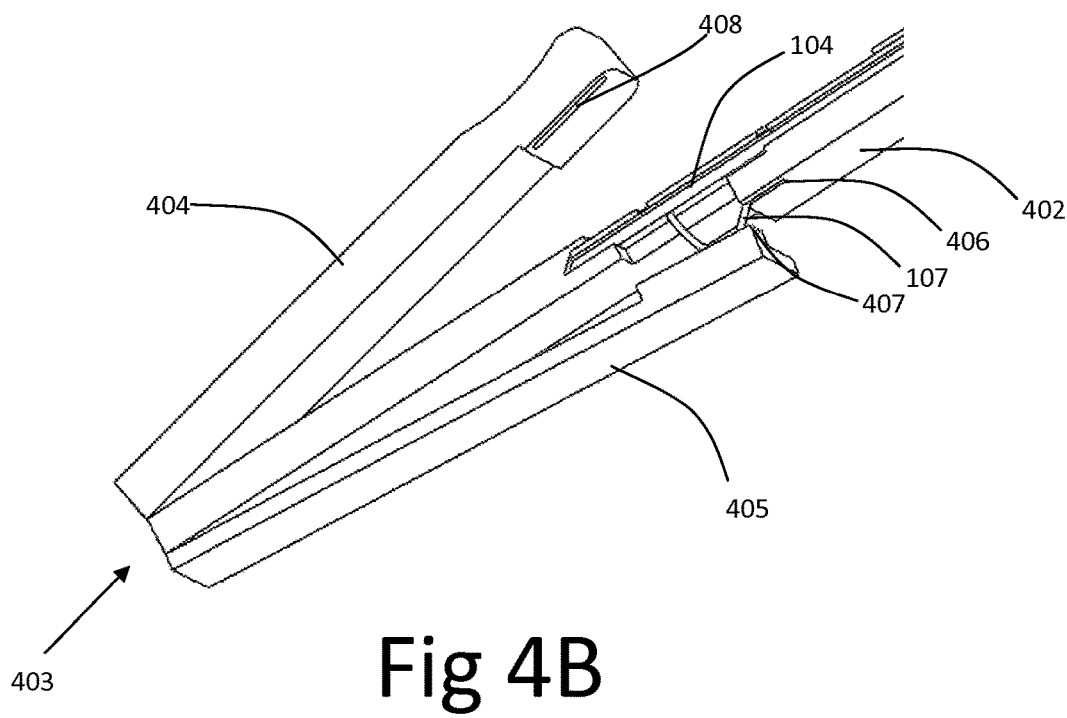

Reference is now made to FIG. 4B which describes the initial stage of each CC 107 and its dedicated stapler 403, (i.e. CC initial stage) in which at least a portion of the u-shaped body 222 of the CC 107 is partially located inside a groove 406 in said holding body 402, thereby providing attachment between the FA 104 and the holding body 402.

Furthermore, in such a manner a detachment of distal portion 101 from the holding body before all CC 107 are inserted to FA 104 is prevented.

The bottom section 405 is adapted to apply force on said CC 107 and to push the same through the FA 104.

Figure 4C:
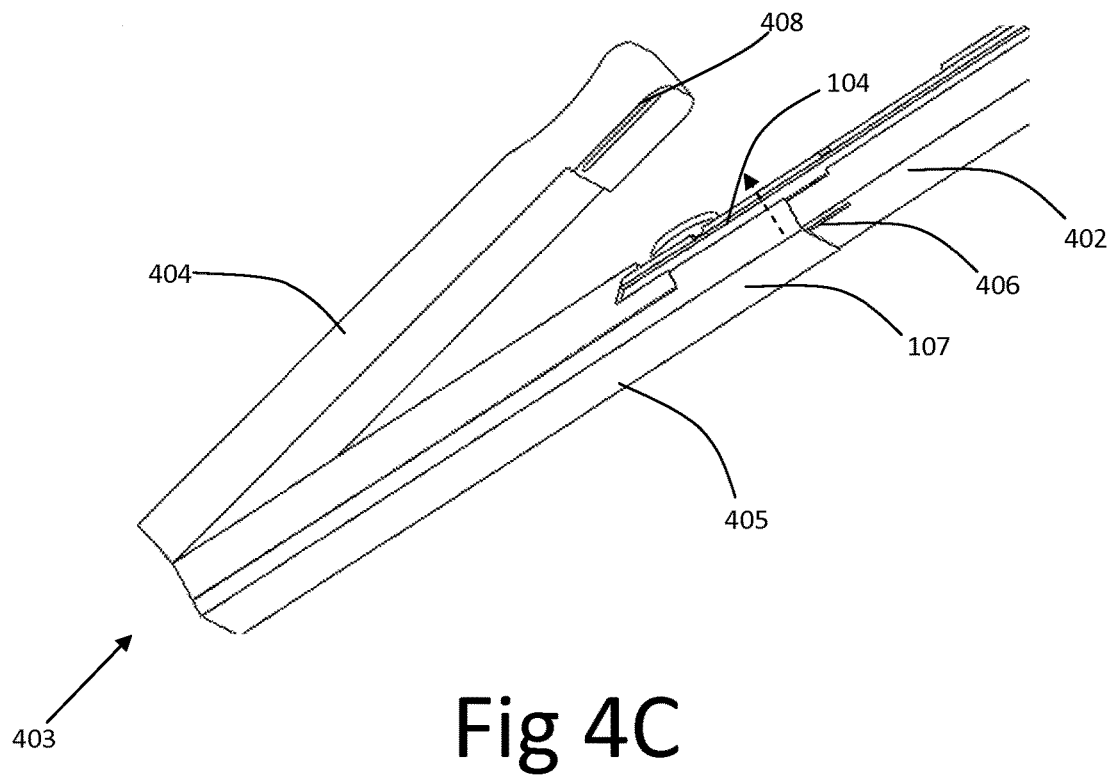

A groove 407 located at the top surface of the bottom section 405 is adapted to prevent lateral motion of the CC 107 during said clip insertion (FIG. 4C).

Said top section 404 is adapted to press patch 106 against FA 104 during said clip insertion, while enabling portion 201 of CC 107 to enter groove 408 located at its bottom surface.

Figure 4D:
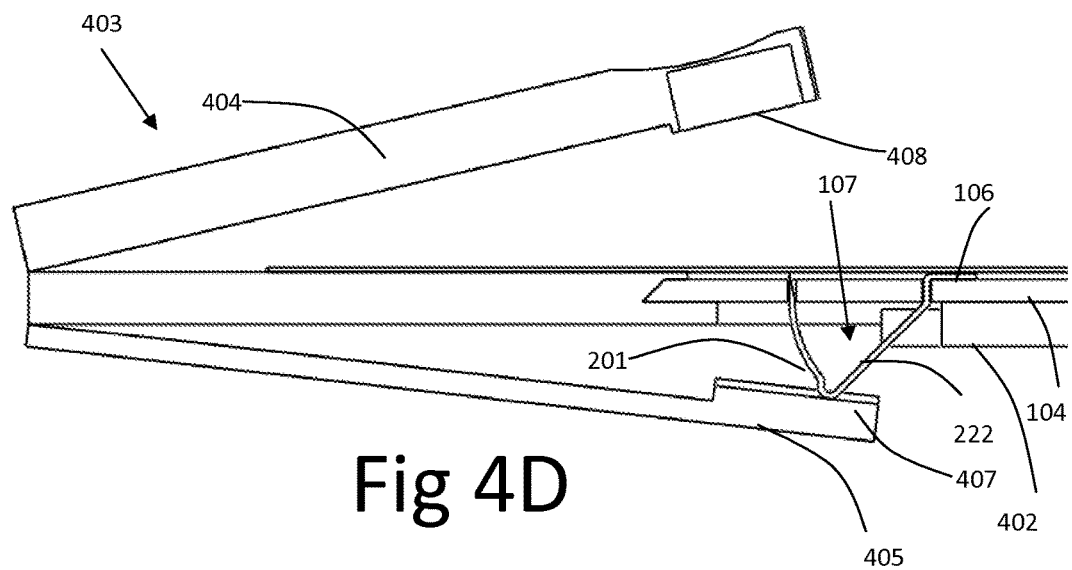
Figure 4E:
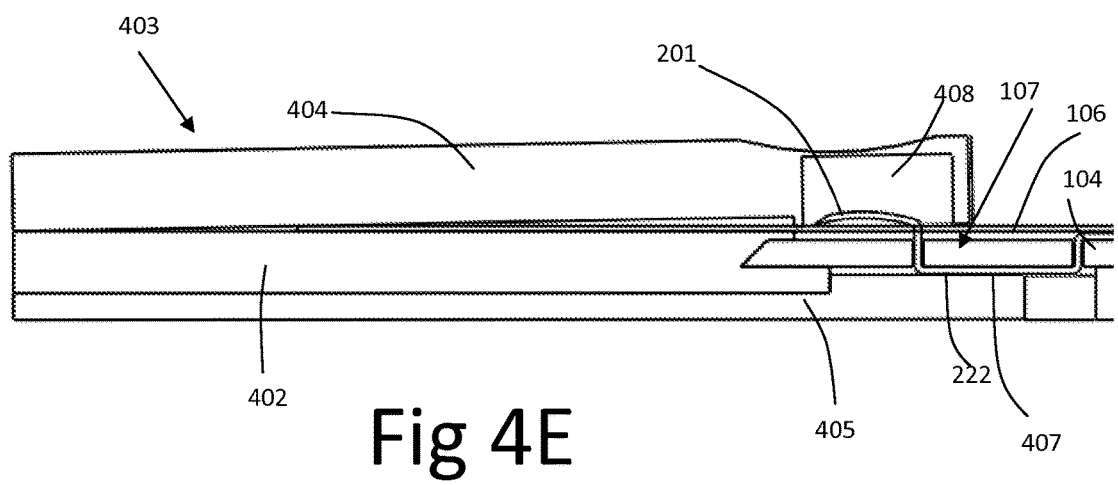

Reference is now made to FIGS. 4D-4E which describe the process of inserting a single CC 107 through FA 104 and patch 106 utilizing said CSA 401.

First, a patch 106 is places on the FA 104 (see. FIG. 4D).

Next, the bottom section 405 and the top section 404 are presses toward each other, hence, inserting the CC 107 through FA 104 and patch 106 into groove 408 at the top section 404 (see FIG. 4E).

It should be pointed out that once the CC 107 is inserted into groove 408 a portion 222 of said CC 107 is removed from groove 406.

Figure 4F:
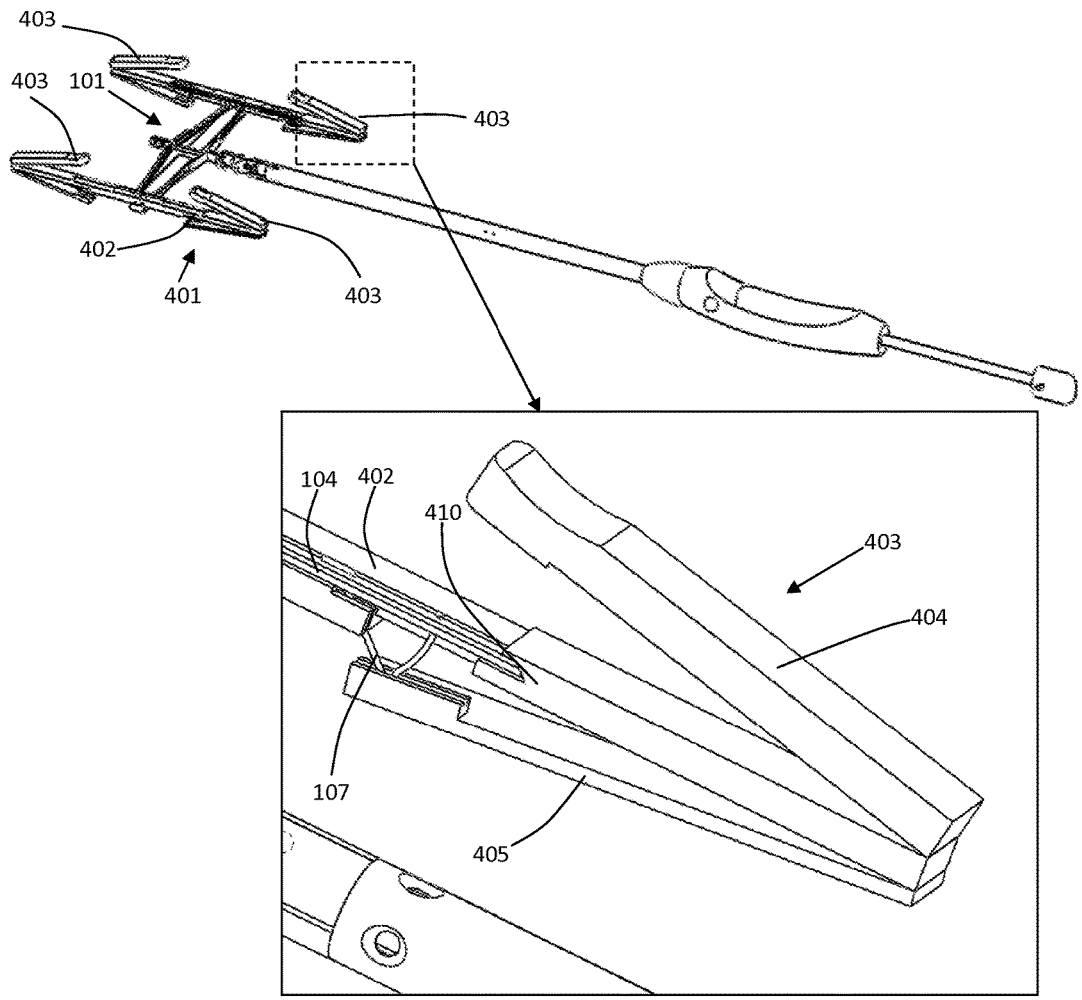
Figure 4G:
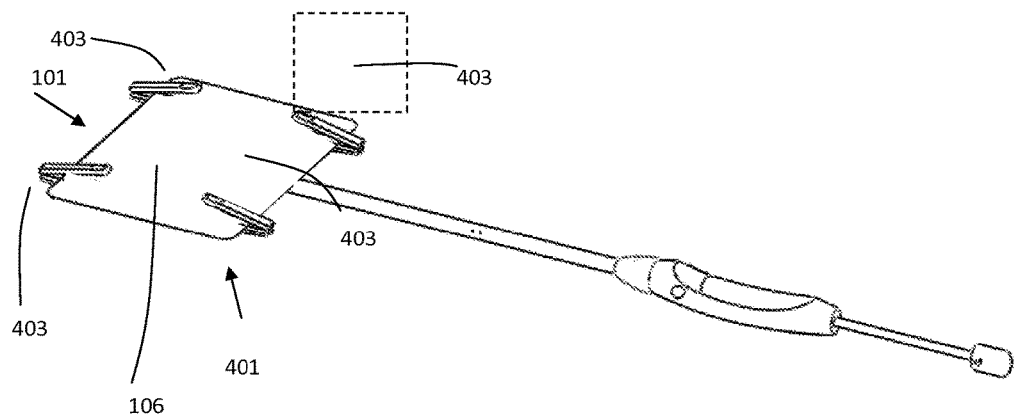
Figure 4H:
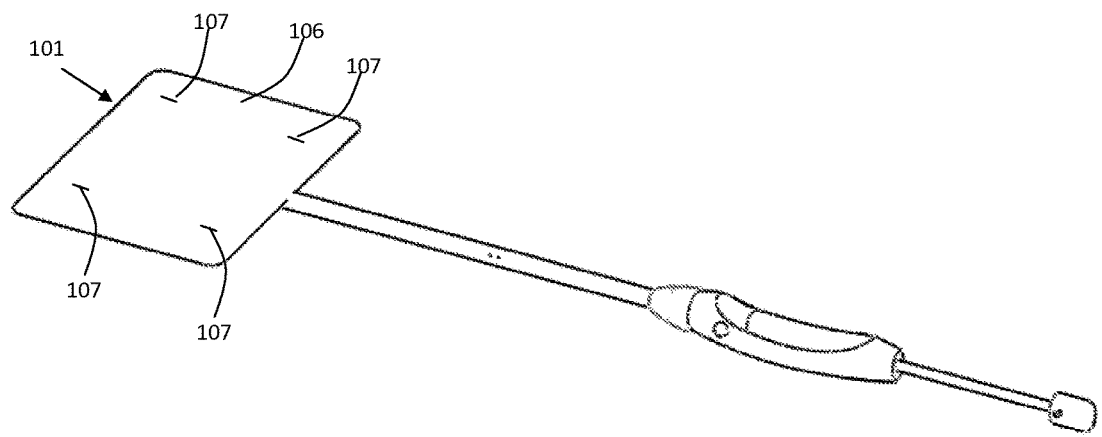

Reference is now made to FIGS. 4F-4H illustrating the process of reversible attaching the patch and the PDD utilizing the CSA 401.

Initially, the FAs 104 of PDD 100 are reversibly coupled to the CSA 401 by inserting them into grooves 410 in the CSA 401; hence, staplers 403 and CC 107 are positioned in said CC initial stage (FIG. 4F). Said coupling operation is preformed prior to the surgery during device assembly.

Next, patch 106 is placed on the FA 104 and below the staplers top sections 404 (see FIG. 4G). Then, patch 106 is reversibly attached to the PDD 100 by inserting all the CCs 107 using their adjacent and dedicated staplers 402.

Once the CCs are fully inserted into the patch and the FAs 104, said reversibly attachment (between the patch and the PDD 100) is obtained and the FAs 104 can be extracted from grooves 410. Next PDD 100, coupled to patch 106, is separated from the CSA 401 (see FIG. 4H).

Staplers 403 can also be used individually, without said holding body 402. According to this embodiment, the staplers are connected directly to the FAs 104, and therefore can be individually removed once clip insertion is performed.

Reference is now being made to FIGS. 5A-5F which describe an alternative method for reversibly connecting said patch to said PDD.

According to this embodiment each CC 107 is fully inserted into the FA 104 and a stapler 501 is utilized for inserting the CC 107 into patch 106.

Stapler 501 comprising a top section 502 and a bottom section 503 connected by a hinge.

Said bottom section is adapted to be coupled with FA 104 by inserting said FA 104 into said bottom section of the stapler 501 through a tubular bore 504 running along the length of the bottom section 503.

A groove 505, located at the top surface of the bottom section, is adapted to house portion 201 of CC 107 while holding it in an upright position (i.e., portion 201 of CC 107 is facing bore 506 of the stapler's top section 502).

Figure 5A:
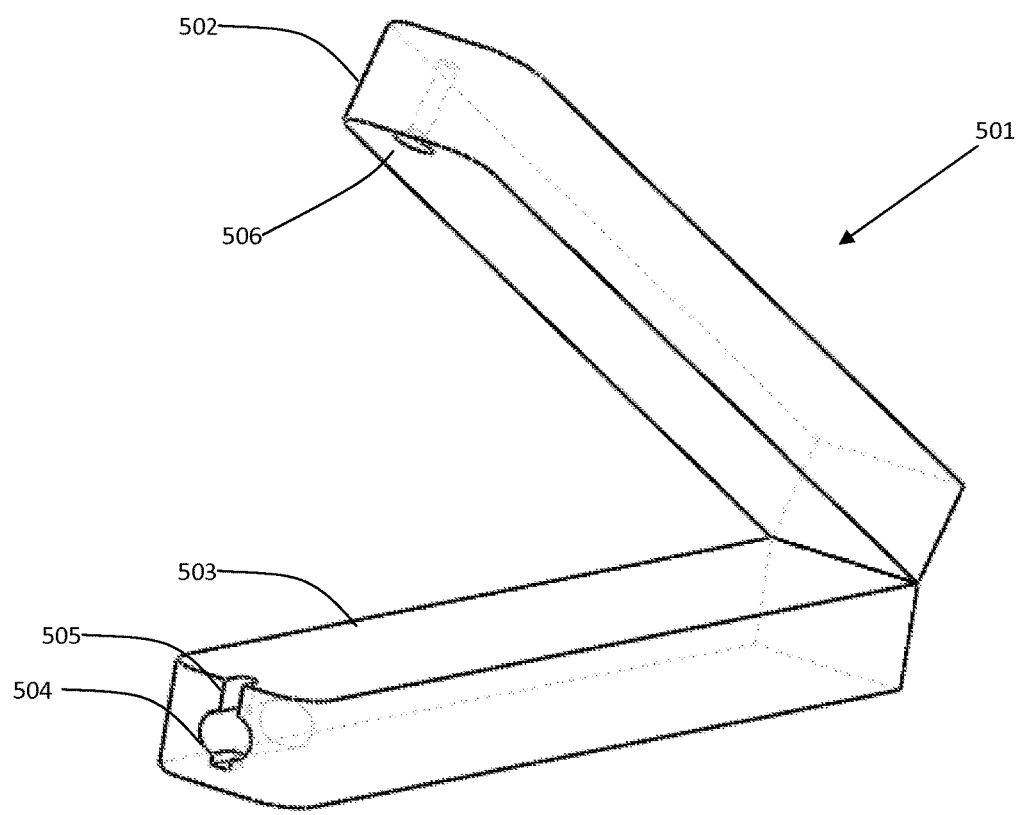
FIGS. 5A-5F illustrate an alternative method for reversibly connecting the patch to said PDD.
Figure 5B:
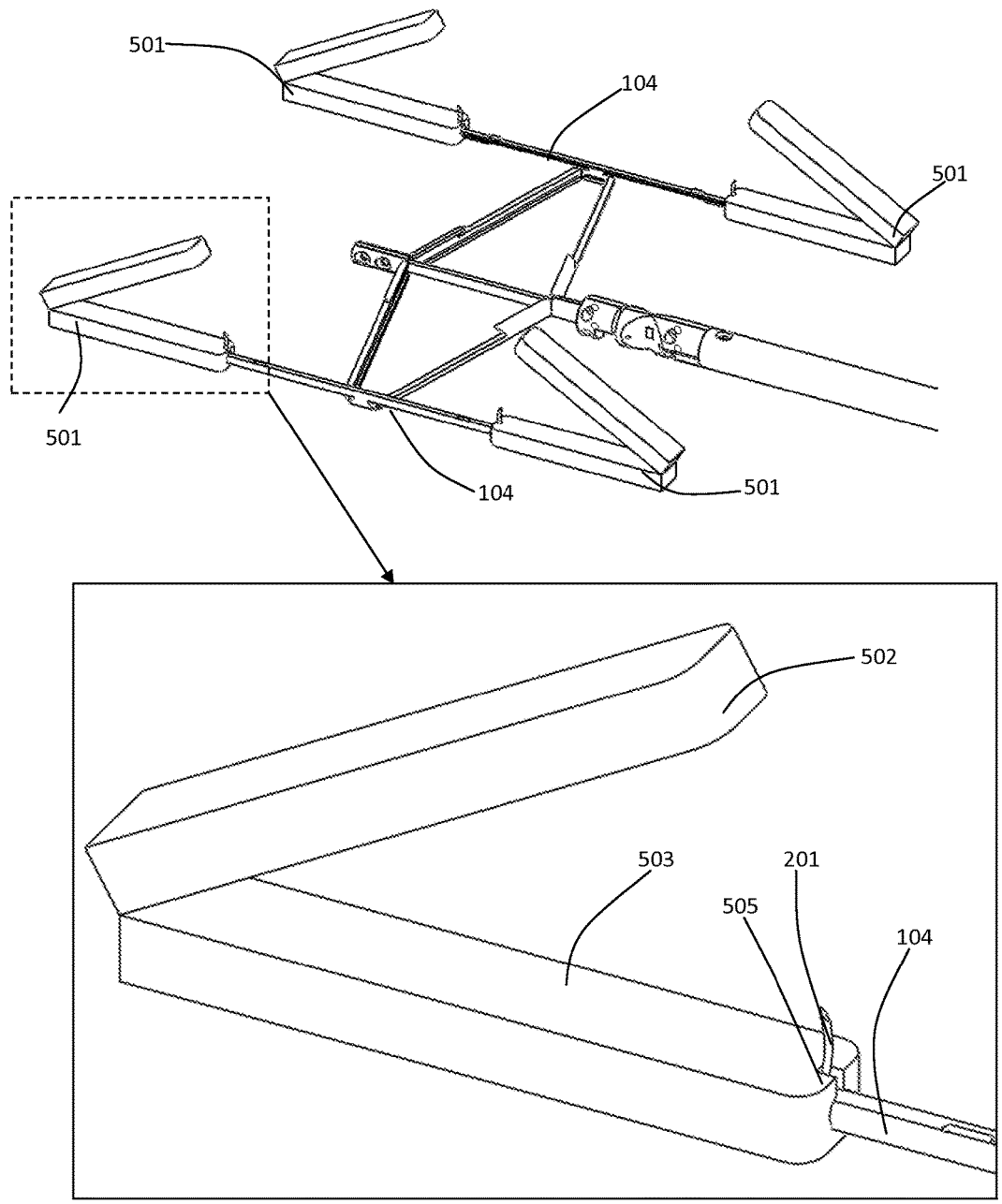
Figure 5C:
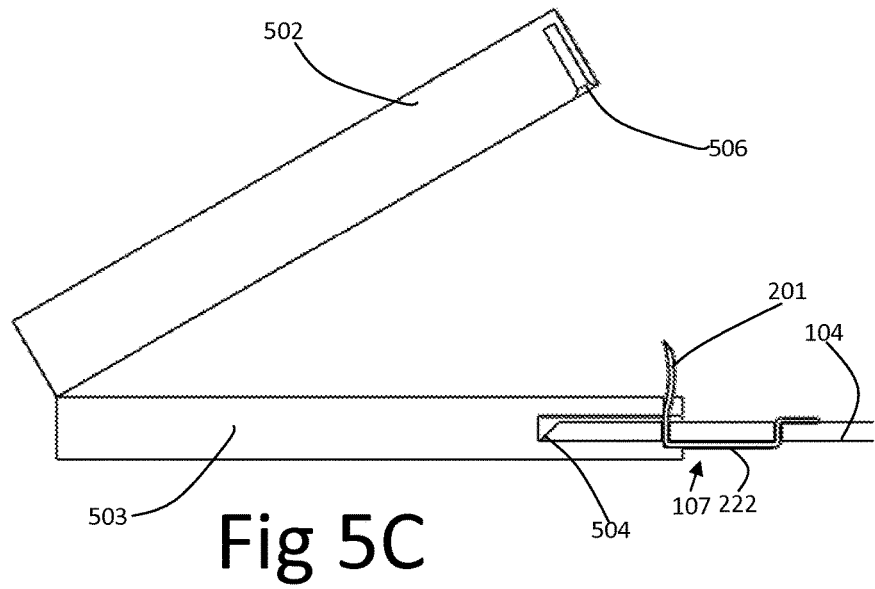

The stapler's top section 502 is adapted to press patch 106 against FA 104 while inserting portion 201 into bore 506 at its bottom surface (see FIG. 5A).

Four staplers 50, are connected to each end of FAs 104. Each stapler 501 is adapted to be in communication with merely one CC 107 while maintaining the same in an upright position (see FIG. 5B).

FIGS. 5C-5F describe a method in which each CC 107 is inserted into patch 106 for reversibly attaching said patch to said PDD.

First the FA 104 is inserted into tubular bore 504 of stapler 501. The CC is initially held in an upright position by stapler 501 (see FIG. 5C).

Figure 5D:
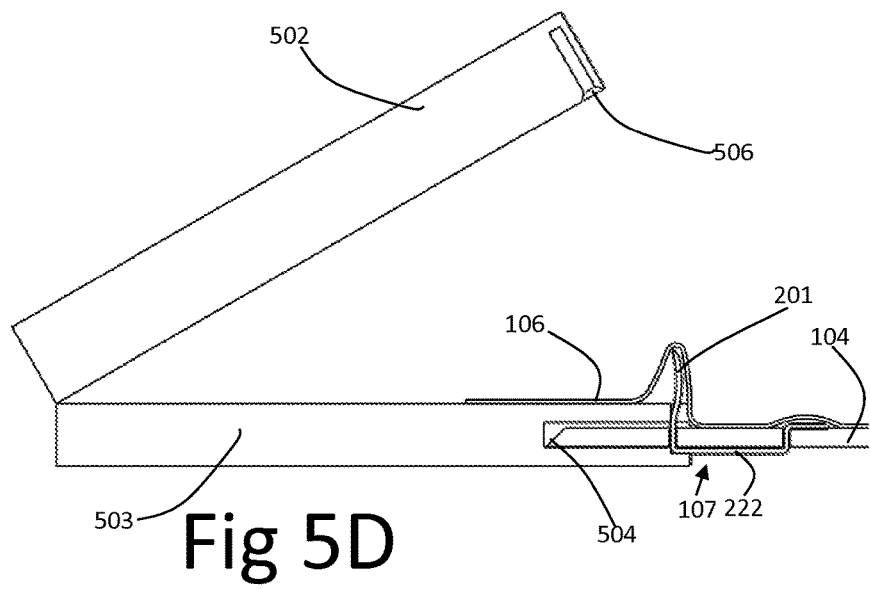

Next, Patch 106 is placed above the FAs 104 and the protruding portion 201 of the CCs 107 (see FIG. 5D).

Figure 5E:
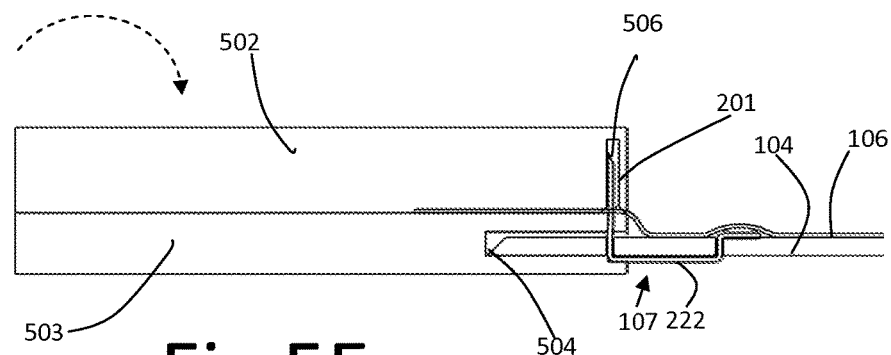

Next, the stapler's top section 502 is lowered toward the FA 104 while inserting portion 201 into bore 506 through patch 106 (see FIG. 5E).

Figure 5F:
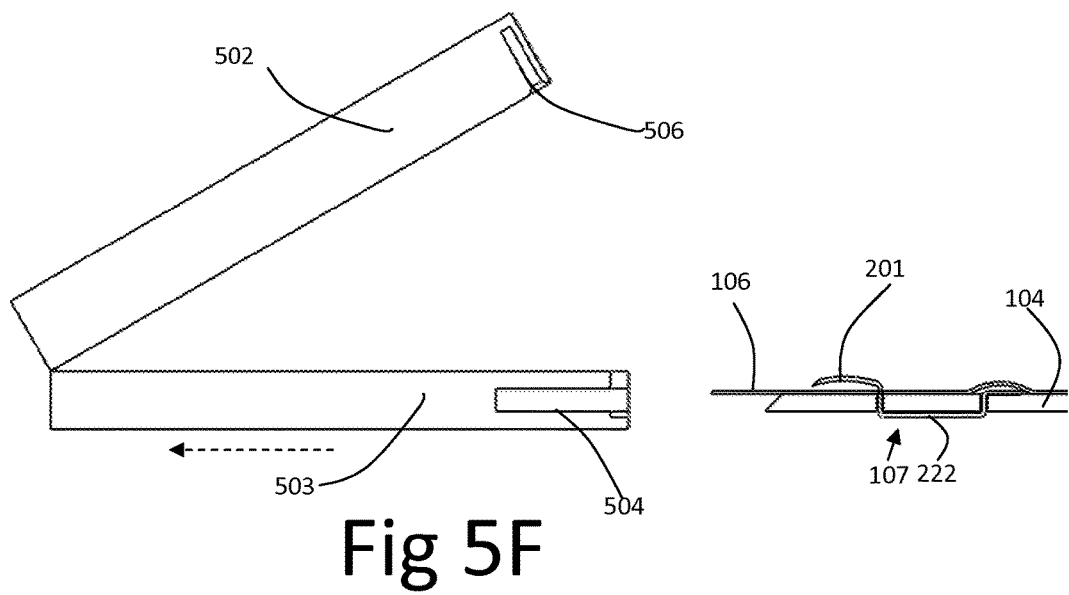

Once CC 107 is fully inserted into bore 506, the top section 502 is elevated back to its initial position, and stapler 501 is removed from FA 104; as a result CC 107 springs back into its pre-shaped form thereby providing said reversible attachment (see FIG. 5F).

Reference is now made to FIGS. 6A-6E which describe yet another alternative approach to provide said reversible connection.

According to this embodiment, the CCs 107 are made of a rigid deformable material (e.g. stainless steel T304, stainless steel T316).

The CCs 107 are inserted through FAs 104 and patch 106 utilizing several staplers 601. Each stapler is mounted on each edge of the FAs 104.

Stapler 601 comprises a top section 602 a bottom section 603 both connected via a hinge. Stapler 601 also comprises a slide 604 sliding towards and away from said top section.

Each CC 107 is pre-mounted within its dedicated stapler 601 and inserted into dedication holes at FAs 104.

The bottom section comprises a groove into which CC 107 is inserted. Said bottom section is adapted to prevent said CC from any unwanted displacement (mainly lateral displacement of the CC).

Slide 604 is adapted to apply forces on the CC 107 and to press the same through FA 104 and patch 106.

The stapler's top section 602 is characterized by a predetermined shape. Said shape will be the CC's shape. Top section 602 comprises two shaping grooves 605.

The stapler's top section is adapted to apply force and press patch 106 against FA 104 whilst shaping CC 107 into its final shape during the process of clip insertion, Reference is now made to FIGS. 6B-6E describing a method for utilizing stapler 601.

Figure 6A:
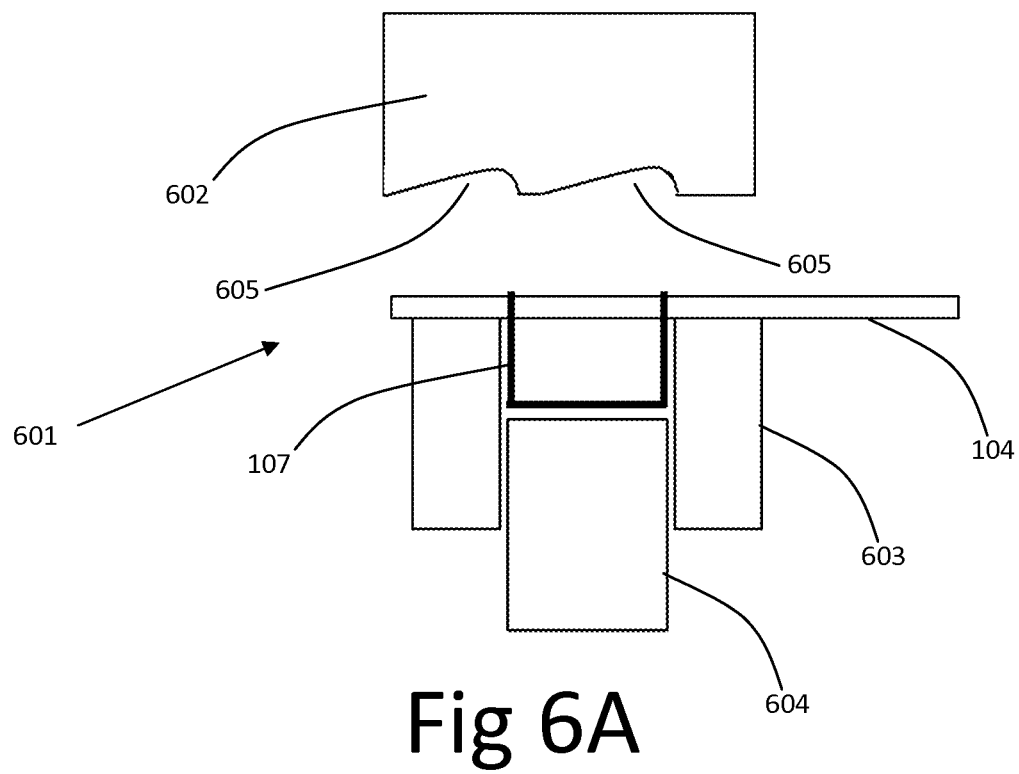
FIGS. 6A-6E illustrate yet another alternative approach to provide said reversible connection.
Figure 6B:
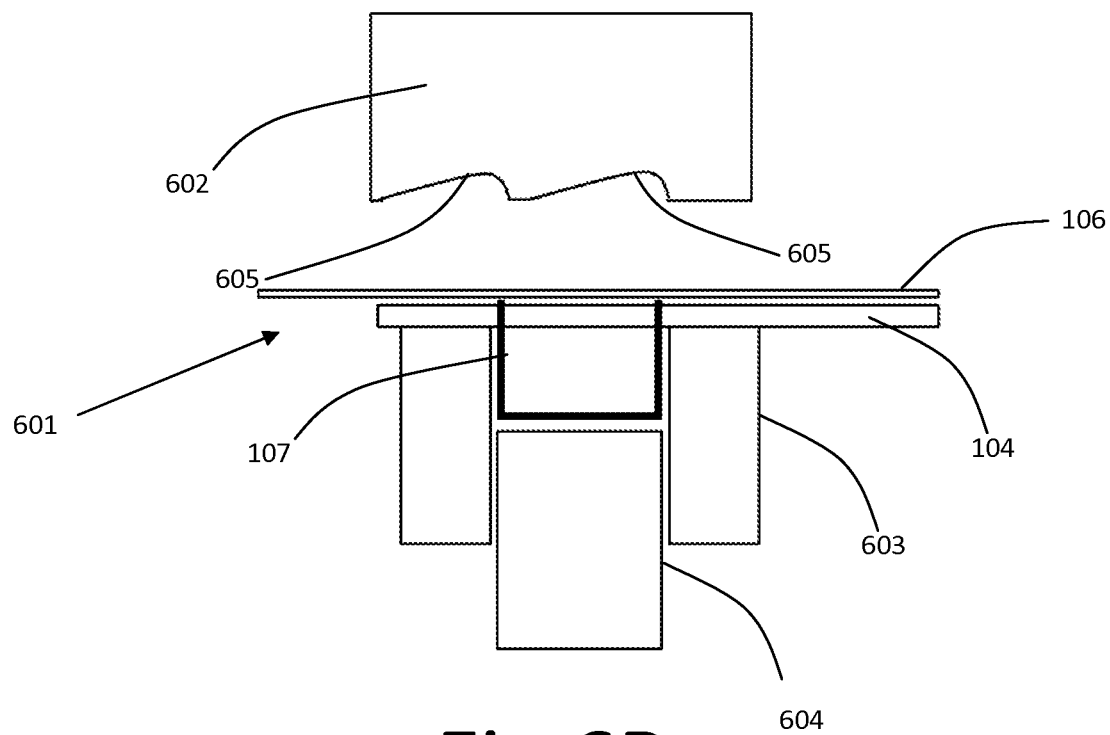

First, patch 106 is positioned above the FA 104 (FIG. 6B).

Figure 6C:
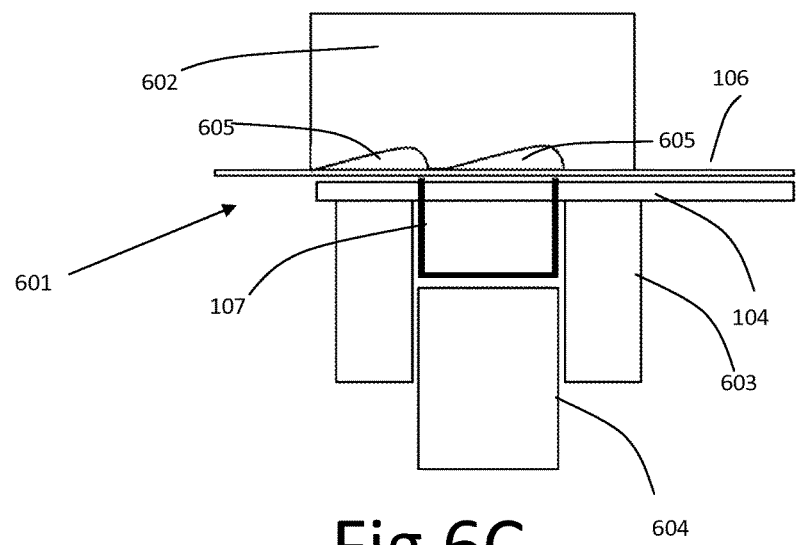
Figure 6D:
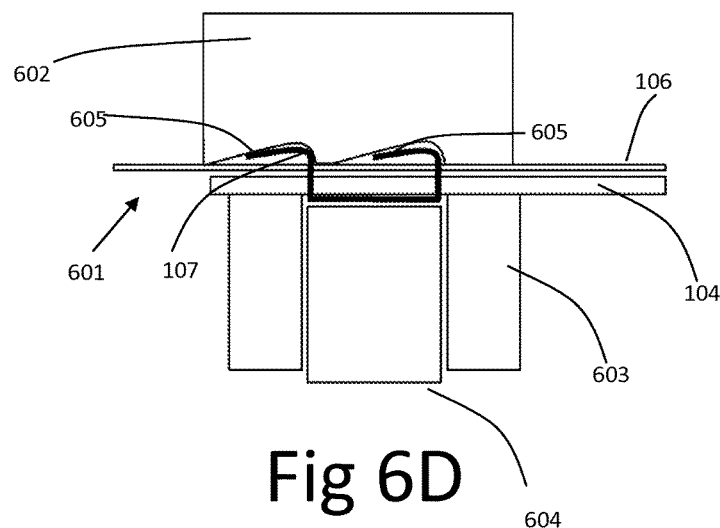
Figure 6E:
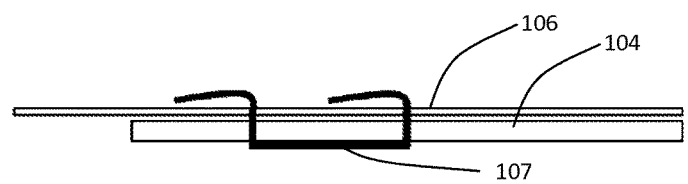

Next, the top section 602 is lowered toward FA 104 whilst pressing patch 106 against it (FIG. 6C).

Next, the slide 604 is pushed upward towards the top section 602. Said movement of the slide 604 causes the CC 107 to penetrate the FA 104 and the patch 106. Furthermore, said movement of said slide 604 presses the CC 107 onto the shaping grooves 605; thereby shaping it into said shaping groove's shape.

As a result the edges of CC 107 are bended (and taking the shape of the shaping grooves 605). Said bending provides said reversible attachment (see FIG. 6D). Once said reversible attachment is obtained, stapler 601 is removed from FA 104 (see FIG. 6E).

Figure 7A:
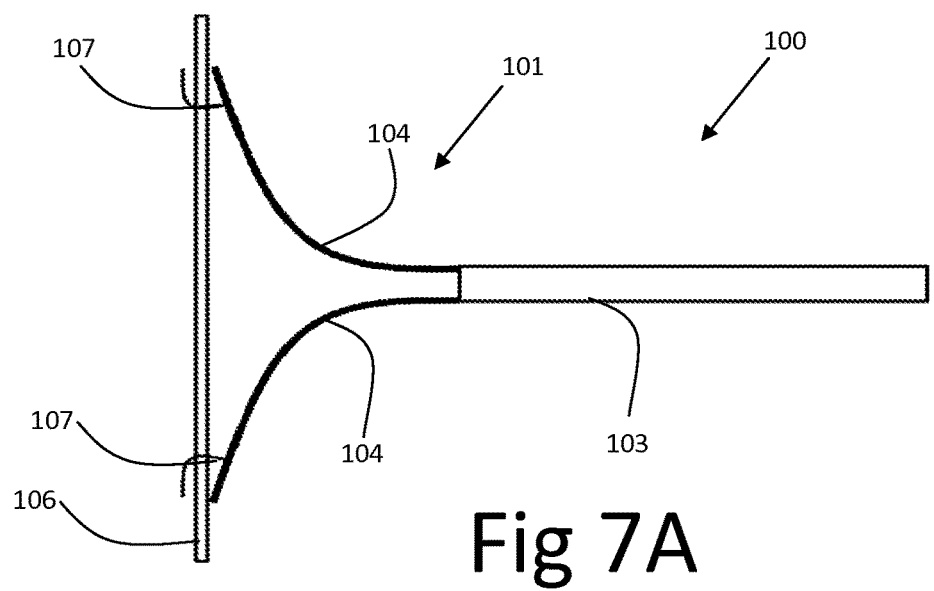
FIGS. 7A-7C illustrate still yet another alternative approach to provide said reversible connection.
Figure 7B:
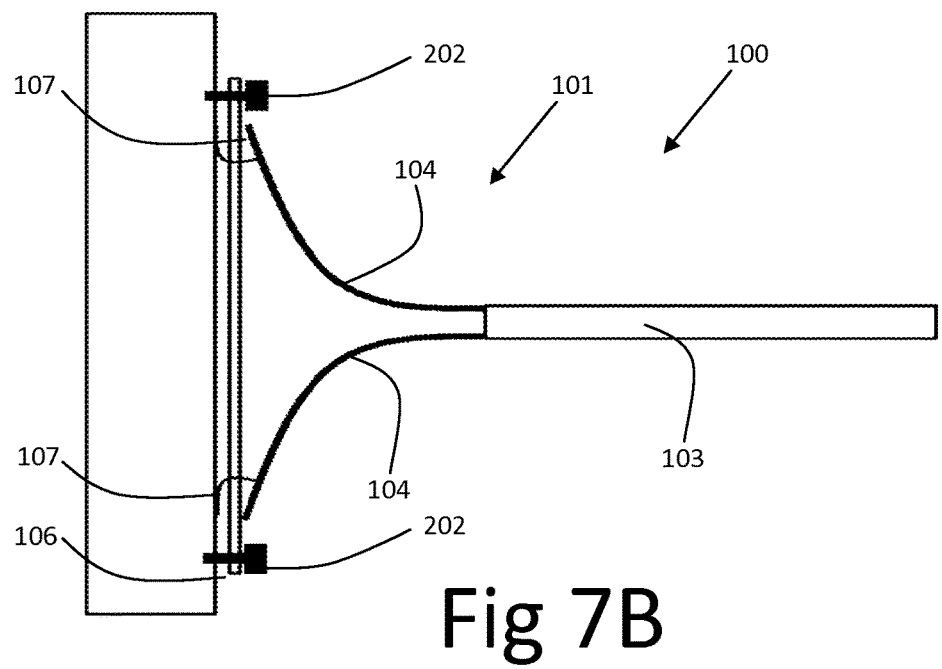
Figure 7C:
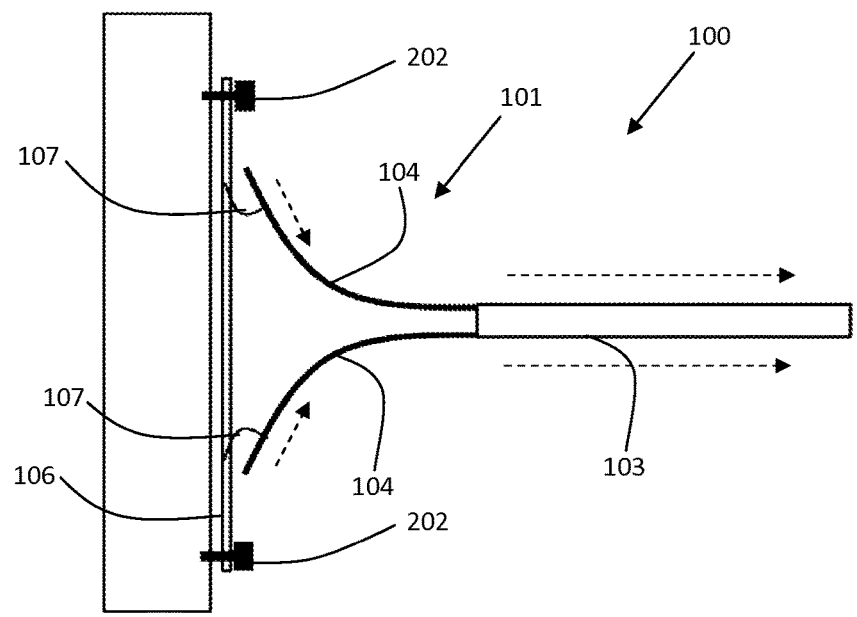

Reference is now made to FIGS. 7A-7C which illustrate an alternative embodiment of PDD 100, utilizing said reversible attachment. According to this embodiment patch 106 is deployed by a least 2 flexible frame arms (FA) 104.

In the closes configuration of PDD 100, FA 104 are substantially straight and aligned with tube 103, hence enabling insertion of patch 106 through trocar 114 (not shown in the figure). Once the distal portion 101 in fully inserted into the patient's abdominal cavity and outside trocar 114, FA 104 are transformed into their open configuration in which they radiate from tube 103 (into a cone-like configuration), hence deploying patch 106 (see FIG. 7A).

According to this embodiment patch 106 is connected to FA 104 via CC 107 located at the end of each FA 104. Each section 201 of each CC 107 is facing outward with regards to tube 103 (see FIG. 7A).

Once the distal portion 101 along with patch 106 is inserted into the patient's abdominal cavity, patch 106 is attached to the patient's tissue 120 by PTC 202 (see FIG. 7B).

At this point PDD 100 is disconnected from patch 106 by applying pulling forces and distancing the distal portion 101 from the tissue; as a result the FAs 104 are deformed such that each CC 107 is pulled toward tube 103 and hence sliding out of patch 106 to provide said detachment according to said mechanism A.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A system for closing an aperture in a biological tissue comprising:
   a first portion of a clip fixedly attached to an arm of a surgical instrument that deploys a surgical implant inside a patient's body, the surgical instrument includes an elongate shaft, wherein the arm and the elongate shaft are parallel in a deployed position and an undeployed position; and
   a second portion of the clip adapted to releasably receive the surgical implant, wherein the second portion has a first configuration relative to the arm of the surgical instrument that retains the surgical implant and a second configuration relative to the arm of the surgical instrument that releases the surgical implant, the second portion being parallel to the arm of the surgical instrument when in the first configuration and a longitudinal axis of the second portion intersects the arm of the surgical instrument when the second portion is in the second configuration,
   wherein the clip deforms from the first configuration to the second configuration to release the surgical implant.

2. The system according to claim 1, wherein the clip is made from a resilient material.

3. The system according to claim 1, wherein the clip is made from a deformable material.

4. The system according to claim 1, wherein transformation of the clip from the first configuration to the second configuration is accomplished by an action selected from the group consisting of: downward pulling, backward pulling, and a combination thereof.

5. The system according to claim 1, wherein the first or second portion comprises a shape that prevents early detachment of the surgical implant from the surgical instrument.

6. The system according to claim 1, wherein the clip is composed of a single elastic wire.

7. The system according to claim 6, wherein the single elastic wire is made from a shape memory alloy.

8. The system according to claim 1, wherein the first portion is configured to have a U shape having a protruding portion extending from an end of the U shape.

9. The system according to claim 1, wherein the clip comprises an elastic material, and the second portion of the clip is pre-shaped into the first configuration, wherein the clip is held in a third configuration until contacted with the surgical implant, at which point the second portion of the clip is transformed from the third configuration to the first configuration.

10. A system for closing an aperture in a biological tissue, the system comprising:
   a handle;
   an elongate shaft connected to the handle;
   a deployment scaffold connected to the elongate shaft, the deployment scaffold transitionable between deployed and undeployed configurations, wherein an arm of the deployment scaffold is parallel to the elongate shaft in the deployed and undeployed configurations; and
   at least one clip connected to the deployment scaffold, the clip including a first portion fixedly coupled to a portion of the deployment scaffold and a second portion extending from the first portion, the second portion transitioning between a first configuration relative to the deployment scaffold and a second configuration relative to the deployment scaffold, the second portion parallel to the deployment scaffold in the first configuration and the second portion defining a longitudinal axis that intersects the deployment scaffold in the second configuration,
   wherein the system is configured to releasably retain a surgical implant when the second portion of the clip is in the first configuration and the system releases the surgical implant when the second portion of the clip is deformed into the second configuration.

11. The system according to claim 10, wherein the at least one clip has a forward facing orientation.

12. The system according to claim 10, wherein the system deploys and attaches the surgical implant to the biological tissue.

13. The system according to claim 10, wherein the scaffold further comprises:
   a frame;
   a plurality of deployment arms hingedly connected to the frame, wherein the plurality of deployment arms are configured to move from a retained position to at least one deployed position;
   wherein the at least one clip is fixedly attached to the frame.

14. The system according to claim 10, wherein the deployment scaffold is configured to allow for deployment of the surgical implant and retraction of the surgical implant while the scaffold is within a patient's body.

15. The system according to claim 10, wherein the deployment scaffold is configured to allow for a plurality of deployment positions.

16. The system according to claim 10, wherein the deployment scaffold comprises an articulating member that allows for adjustment of a position and an orientation of the surgical implant relative to the aperture in the biological tissue.

17. The system according to claim 10, wherein the surgical implant is a patch.

18. The system according to claim 17, wherein the patch is comprised of surgical mesh.

19. The system according to claim 10, wherein the aperture in the biological tissue is an aperture in an abdominal wall.

20. The system according to claim 10, wherein at least a portion of the elongate shaft is flexible.

21. The system according to claim 10, wherein the elongate shaft is rigid.

22. The system according to claim 10, further comprising at least one stapler adapted to interact with the deployment scaffold.

23. The system according to claim 22, wherein the stapler connects the clip to the deployment scaffold.

24. A system for closing an aperture in a biological tissue comprising:
   a handle;
   an elongate shaft connected to the handle;
   an arm movably coupled to the elongate shaft; and
   a clip connected to the arm, the clip including a first portion fixedly coupled to a portion of the arm and a second portion extending from the first portion, the second portion transitioning between a first configuration relative to the arm and a second configuration relative to the arm, the second portion parallel to the arm in the first configuration and the second portion defining a longitudinal axis that intersects the arm in the second configuration, wherein the system is configured to releasably retain a surgical implant when the second portion of the clip is in the first configuration and the system releases the surgical implant when the second portion of the clip is deformed into the second configuration, wherein movement of the arm relative to the elongate shaft is parallel movement.

25. The system of claim 24, wherein the surgical implant is released when the second portion of the clip is in the second configuration and the elongate shaft is moved relative to the aperture.

26. The system of claim 24, wherein the surgical implant is released when the second portion of the clip is in the second configuration and the arm is moved relative to the aperture.

* * * * *